United States Patent
Kitano et al.

(10) Patent No.: US 6,271,251 B1
(45) Date of Patent: Aug. 7, 2001

(54) SUBSTITUTED GUANIDINE DERIVATIVES, PROCESS FOR PRODUCTION THEREOF, AND PHARMACEUTICAL USES THEREOF

(75) Inventors: Masahumi Kitano; Naohito Ohashi, both of Takatsuki (JP)

(73) Assignee: Sumitomo Pharmaceuticals Company Limited, Osaka (JP)

( * ) Notice: Subject to any disclaimer, the term of this patent is extended or adjusted under 35 U.S.C. 154(b) by 0 days.

(21) Appl. No.: 09/342,101

(22) Filed: Jun. 29, 1999

Related U.S. Application Data

(62) Division of application No. 09/074,462, filed on May 8, 1998, now Pat. No. 5,977,100, which is a division of application No. 08/790,024, filed on Jan. 28, 1997, now Pat. No. 5,834,454.

(30) Foreign Application Priority Data

| Feb. 2, 1996 | (JP) | 8-040611 |
| Apr. 25, 1996 | (JP) | 8-131370 |
| Jul. 31, 1996 | (JP) | 8-219322 |
| Dec. 24, 1996 | (JP) | 8-356301 |

(51) Int. Cl.⁷ .................. A61K 31/40; C07D 245/00; C07D 487/00
(52) U.S. Cl. .................................... 514/411; 540/471
(58) Field of Search .................. 540/471; 514/411

(56) References Cited

U.S. PATENT DOCUMENTS

| 4,567,177 | 1/1986 | Bigg et al. | 514/214 |
| 5,100,884 | * 3/1992 | Hamminga et al. | 514/183 |
| 5,814,654 | 9/1998 | Kitano et al. | 514/411 |

FOREIGN PATENT DOCUMENTS

| 33014/93 | 8/1993 | (AU) . |
| 33015/93 | 8/1993 | (AU) . |
| 68844/94 | 2/1995 | (AU) . |
| 81700/94 | 6/1995 | (AU) . |
| 16354/94 | 10/1995 | (AU) . |
| 17861/95 | 11/1995 | (AU) . |
| 30251/95 | 2/1996 | (AU) . |
| 30144/95 | 3/1996 | (AU) . |
| 30250/95 | 3/1996 | (AU) . |
| 21720/95 | 4/1996 | (AU) . |
| 0322016 | 6/1989 | (EP) . |
| 0386628 | 9/1990 | (EP) . |
| 0387618 | 9/1990 | (EP) . |
| 0620221 | 10/1994 | (EP) . |
| 0622356 | 11/1994 | (EP) . |
| 0639573 | 2/1995 | (EP) . |
| 0708091 | 4/1996 | (EP) . |
| 0719766 | 7/1996 | (EP) . |
| 0726254 | 8/1996 | (EP) . |
| 94/26709 | 11/1994 | (WO) . |

OTHER PUBLICATIONS

Naruto S., Tetrahedron Leters No. 39, pp 3399–3402, 1975.*
Journal of the American Chemical Society, vol. 80, No. 20, Oct. 20, 1958, pp. 5574–5575.
Khim. Geterotsikl. Soedin., No. 6, 1979, pp. 839–841.
Khim. Geterotsikl. Soedin., No. 7, 1981, pp. 938–986.

* cited by examiner

*Primary Examiner*—Bruck Kifle
(74) *Attorney, Agent, or Firm*—Sughrue, Mion, Zinn, Macpeak & Seas, PLLC

(57) ABSTRACT

A substituted guanidine derivative represented by the general formula:

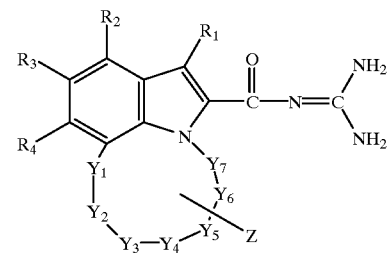

or a pharmaceutically acceptable acid addition salt thereof, is useful as a therapeutic or prophylactic agent for diseases caused by the acceleration of the sodium/proton ($Na^+/H^+$) exchange transport system, for example, hyperpiesia, arrhythmia, angina pectoris, hypercardia, diabetes, organopathies due to ischemia or ischemia re-perfusion, troubles due to cerebral ischemia, diseases caused by cell overproliferations, and diseases caused by trouble with endothelial cells.

13 Claims, No Drawings

SUBSTITUTED GUANIDINE DERIVATIVES, PROCESS FOR PRODUCTION THEREOF, AND PHARMACEUTICAL USES THEREOF

This application is a division of Ser. No. 09/074,462 filed May 8, 1998 now U.S. Pat. No. 5,977,100 which is a division of Ser. No. 08/790,024 filed Jan. 28, 1997 now U.S. Pat. No. 5,834,454.

BACKGROUND OF THE INVENTION

1. Field of the Invention

The present invention relates to novel guanidine derivatives or salts thereof, a process for production thereof, and pharmaceutical uses thereof. The compounds of the present invention have inhibitory effect on the sodium/proton ($Na^+$/$H^+$) exchange transport system and hence are useful as a therapeutic or prophylactic agent for diseases caused by the acceleration of the sodium/proton ($Na^+$/$H^+$) exchange transport system, for example, hyperpiesia, arrhythmia, angina pectoris, hypercardia, diabetes, organopathies due to ischemia or ischemia re-perfusion [for instance, troubles caused by myocardial ischemia re-perfusion, acute renal failute, and surgical treatments (e.g. organ transplantation and PTCA (percutaneous transluminal coronary angioplasty))], troubles due to cerebral ischemia (e.g. troubles accompanying cerebral infarction, troubles brought about as after-effects of cerebral apoplexy, and cerebral edema), diseases caused by cell over-proliferations (e.g. fibroblast proliferation, smooth muscle cell proliferation and mesangial cell proliferation) (e.g. atherosclerosis, fibroid lung, fibroid liver, fibroid kidney, renal glomerulosclerosis, organ hypertrophy, prostatomegaly, complications of diabetes, and re-constriction after PTCA), and diseases caused by trouble with endothelial cells.

2. Related Art Statement

As substituted guanidine derivatives having inhibitory effect on the sodium/proton ($Na^+$/$H^+$) exchange transport system, there are known, for example, pyrazinoylguanidine derivatives represented by amiloride (for instance, J. Membrane Biol., Vol. 105, 1 (1988); Circulation, Vol. 79, 1257 (1989)). It has been reported that benzoylguanidine derivatives have inhibitory effect on the sodium/proton ($Na^+$/$H^+$) exchange transport system and hence antiarrhythmic effect (for instance, J. Mol. Cell. Cardiol., Vol. 24, Suppl. I, S. 92 (1992); J. Mol. Cell. Cardiol., Vol. 24, Suppl. I, S. 117 (1992), Japanese Patent Unexamined Publication Nos. 5-339228, 6-9545, 6-345715 and 7-109251). It has also been reported that polycyclic aroylguanidine derivatives have inhibitory effect on the sodium/proton (Na+/H+) exchange transport system (for instance, Japanese Patent Unexamined Publication Nos. 7-10839, 7-145149 and 7-206823).

SUMMARY OF THE INVENTION

The present invention is intended to provide novel guanidine derivatives or salts thereof, which have inhibitory effect on the sodium/proton ($Na^+$/$H^+$) exchange transport system and hence are useful as a therapeutic or prophylactic agent for diseases caused by the acceleration of the sodium/proton ($Na^+$/$H^+$) exchange transport system, for example, hyperpiesia, arrhythmia, angina pectoris, hypercardia, diabetes, organopathies due to ischemia or ischemia re-perfusion [for instance, troubles caused by myocardial ischemia re-perfusion, acute renal failute, and surgical treatments (e.g. organ transplantation and PTCA (percutaneous transluminal coronary angioplasty))], troubles due to cerebral ischemia (e.g. troubles accompanying cerebral infarction, troubles brought about as after-effects of cerebral apoplexy, and cerebral edema), diseases caused by cell over-proliferations (e.g. fibroblast proliferation, smooth muscle cell proliferation and mesangial cell proliferation) (e.g. atherosclerosis, fibroid lung, fibroid liver, fibroid kidney, renal glomerulosclerosis, organ hypertrophy, prostatomegaly, complications of diabetes, and re-constriction after PTCA), and diseases caused by trouble with endothelial cells;

a process for production of said derivatives or salts thereof; and pharmaceutical uses of the derivatives or salts.

The first aspect of the present invention is directed to a novel substituted guanidine derivative represented by the general formula (1):

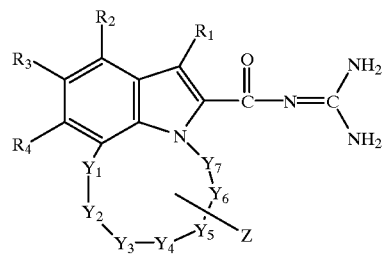

(1)

wherein $R_1$, $R_2$, $R_3$ and $R_4$ are independently a hydrogen atom, an unsubstituted alkyl group, a substituted alkyl group, a cycloalkyl group, a cycloalkenyl group, a saturated heterocyclic group, a halogen atom, a nitro group, a carboxyl group, an alkoxycarbonyl group, an aromatic group, an acyl group, $—OR_5$, $—N(R_6)R_7$, $—CON(R_6)R_7$, $—SO_2N(R_6)R_7$, $—S(O)_nR_8$ wherein $R_8$ is an unsubstituted alkyl group, a substituted alkyl group or an aromatic group, and n is an integer of 0, 1 or 2, $—Q—Ra$, or

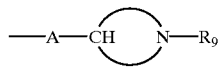

wherein A is an oxygen atom, $—S(O)_n—$ wherein n is as defined above or $—N(R_{10})—$, $R_9$ is a hydrogen atom, an unsubstituted alkyl group, a substituted alkyl group, an acyl group or $—Q—Ra$, and the ring is a 3- to 8-membered saturated heterocyclic group composed of a nitrogen atom and carbon atoms;

$Y_1$, $Y_2$, $Y_3$, $Y_4$, $Y_5$, $Y_6$ and $Y_7$, which may be the same or different, are independently a single bond, $—CH_2—$, $—O—$, $—CO—$, $—C(=C(R_{11})R_{12})—$, $—S(O)_n—$ or $—N(R_{10})—$, adjacent members of a group consisting of $Y_1$ through $Y_7$ being able to be taken together to represent $—CH=CH—$, and at least two of $Y_1$ through $Y_7$ being independently a group other than a single bond;

Z may be absent, or one or more Zs may be present and are, the same or different, independently the following substituent for a hydrogen atom bonded to any of the carbon atoms constituting the ring formed by $Y_1$ through $Y_7$: an unsubstituted alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, an acyl group, $—OR_5$, $—N(R_6)R_7$, $—S(O)_nR_8$, $—C(O)N(R_6)$ $R_7$, or —Q—Ra, provided that when Z is a substituent for the hydrogen atom of —CH=CH—, Z is not —N($R_6$)$R_7$ or —S(O)$_n$$R_8$;

Q is a substituted or unsubstituted lower alkylene group;

Ra is a substituted or unsubstituted vinyl group, or a substituted or unsubstituted ethynyl group;

$R_5$ is a hydrogen atom, an unsubstituted alkyl group, a substituted alkyl group, a cycloalkyl group, a cycloalkenyl group, a saturated heterocyclic group or an aromatic group;

$R_6$ and $R_7$ are independently a hydrogen atom, an unsubstituted alkyl group, a substituted alkyl group, a cycloalkyl group, a cycloalkenyl group, a saturated heterocyclic group, an aromatic group, an acyl group or —Q—Ra, or $R_6$ and $R_7$, when taken together with the nitrogen atom to which they are bonded, form a saturated 5- to 7-membered cyclic amino group which may contain an oxygen atom or a sulfur atom in the ring and may be substituted by one or more unsubstituted alkyl groups, substituted alkyl groups, hydroxyl groups or —O$R_5$ groups;

$R_8$ is an unsubstituted alkyl group, a substituted alkyl group or an aromatic group;

$R_{10}$ is a hydrogen atom, an unsubstituted alkyl group, a substituted alkyl group, a cycloalkyl group, a saturated heterocyclic group, an aromatic group, an acyl group or —Q—Ra; and $R_{11}$ and $R_{12}$ are independently a hydrogen atom, an unsubstituted alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, an acyl group, —O$R_5$, —N($R_6$)$R_7$, —CON($R_6$)$R_7$, —S(O)$_n$$R_8$ or —Q—Ra or a pharmaceutically acceptable acid addition salt thereof.

The second aspect of the present invention is directed to a process for producing a compound of the formula (1) or a pharmaceutically acceptable acid addition salt thereof which comprises reacting a compound represented by the formula (2):

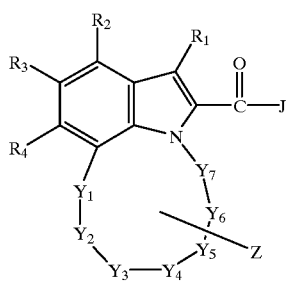

(2)

wherein $R_1$, $R_2$, $R_3$, $R_4$, $Y_1$, $Y_2$, $Y_3$, $Y_4$, $Y_5$, $Y_6$, $Y_7$ and Z are as defined above, and J is a leaving group replaceable by a nucleophilic reagent, with guanidine.

The third aspect of the present invention is directed to a pharmaceutical composition comprising a substituted guanidine derivative of the formula (1) or a pharmaceutically acceptable acid addition salt thereof as an active ingredient.

The fourth aspect of the present invention is directed to a pharmaceutical composition for inhibiting sodium/proton exchange transport system, comprising a substituted guanidine derivative of the formula (1) or a pharmaceutically acceptable acid addition salt thereof as an active ingredient.

The fifth aspect of the present invention is directed to a pharmaceutical composition for the treatment or prophylaxis of hyperpiesia, arrhythmia, angina pectoris, hypercardia, diabetes, organopathies due to ischemia or ischemia re-perfusion, troubles due to cerebral ischemia, diseases caused by cell over-proliferations, and diseases caused by trouble with endothelial cells, which comprises a substituted guanidine derivative of the formula (1) or a pharmaceutically acceptable acid addition salt thereof as an active ingredient.

The sixth aspect of the present invention is directed to a substituted guanidine derivative of the formula (1) or a pharmaceutically acceptable acid addition salt thereof for use as an active ingredient of a pharmaceutical composition.

The seventh aspect of the present invention is directed to use of a substituted guanidine derivative of the formula (1) or a pharmaceutically acceptable acid addition salt thereof for the preparation of a pharmaceutical composition for inhibiting a sodium/proton exchange transport system.

The eighth aspect of the present invention is directed to a method for treating or preventing diseases caused by accelerated sodium/proton exchange transport system, which comprises administering an effective amount of a substituted guanidine derivative of the formula (1) or a pharmaceutically acceptable acid addition salt thereof to an animal including a human being.

The ninth aspect of the present invention is directed to a method for treating or preventing hyperpiesia, arrhythmia, angina pectoris, hypercardia, diabetes, organopathies due to ischemia or ischemia re-perfusion, troubles due to cerebral ischemia, diseases caused by cell over-proliferations, and diseases caused by trouble with endothelial cells, which comprises administering an effective amount of a substituted guanidine derivative of the formula (1) or a pharmaceutically acceptable acid addition salt thereof to an animal including a human being.

DETAILED DESCRIPTION OF THE INVENTION

The various groups in the present invention are explained below.

The alkyl group includes, for example, linear or branched alkyl groups of 8 or less carbon atoms, such as methyl, ethyl, propyl, 2-propyl, butyl, 2-butyl, 2-methylpropyl, 1,1-dimethylethyl, pentyl, hexyl, heptyl, octyl, etc.

The cycloalkyl group may be unsubstituted or may be substituted by 1 to 4 unsubstituted alkyl groups, substituted alkyl groups, hydroxyl groups or groups of the formula —O$R_5$, and includes, for example, 3- to 8-membered cycloalkyl groups such as cyclopropyl, cyclobutyl, cyclopentyl, cyclohexyl, cycloheptyl, 2-methylcyclopentyl, 3-methylcyclopentyl, 2-methylcyclohexyl, 3-methylcyclohexyl, 4-methylcyclohexyl, 2-hydroxycyclopentyl, 3-hydroxycyclopentyl, 2-hydroxycyclohexyl, 3-hydroxycyclohexyl, 4-hydroxycyclohexyl, 2-(hydroxymethyl)cyclopentyl, 3-(hydroxymethyl)cyclopentyl, 2-(hydroxymethyl)cyclohexyl, 3-(hydroxymethyl)cyclohexyl, 4-(hydroxymethyl)cyclohexyl, 2-(aminomethyl)cyclopentyl, 3-(aminomethyl)cyclopentyl, 2-(aminomethyl)cyclohexyl, 3-(aminomethyl)cyclohexyl, 4-(aminomethyl)cyclohexyl, 2-(methoxymethyl)cyclopentyl, 3-(methoxymethyl)cyclopentyl, 2-(methoxymethyl)cyclohexyl, 3-(methoxymethyl)cyclohexyl, 4-(methoxymethyl)cyclohexyl, etc.

The cycloalkenyl group may be unsubstituted or may be substituted by 1 to 4 unsubstituted alkyl groups, substituted alkyl groups, hydroxyl groups or groups of the formula —OR$_5$, and includes, for example, 3- to 8-membered cycloalkenyl groups having a double bond, such as 1-cyclopentenyl, 2-cyclopentenyl, 3-cyclopentenyl, 1-cyclohexenyl, 2-cyclohexenyl, 3-cyclohexenyl, etc.

The saturated heterocyclic group may be unsubstituted or may be substituted by 1 to 4 unsubstituted alkyl groups, substituted alkyl groups, hydroxyl groups or groups of the formula —OR$_5$, and includes, for example, 3- to 8-membered saturated heterocyclic groups having an oxygen atom or a sulfur atom, such as 2-tetrahydrofuranyl, 3-tetrahydrofuranyl, 2-tetrahydro-2H-pyranyl, 4-tetrahydro-4H-pyranyl, etc.

The halogen atom includes, for example, fluorine, chlorine and bromine.

The alkoxycarbonyl group includes, for example, linear or branched alkoxycarbonyl group of 6 or less carbon atoms, such as methoxycarbonyl, ethoxycarbonyl, propoxycarbonyl, 2-propoxycarbonyl, etc.

The aromatic group includes substituted or unsubstituted aryl groups and substituted or unsubstituted heteroaryl groups. As the aryl groups, there may be exemplified aryl groups of 10 or less carbon atoms, such as phenyl, naphthyl, etc. As the heteroaryl groups, there may be exemplified 5- or 6-membered heteroaryl groups containing 1 to 4 nitrogen atoms, and 5- or 6-membered heteroaryl groups containing 0 to 2 nitrogen atoms and an oxygen atom or a sulfur atom, such as 2-, 3- or 4-pyridyl, pyrrolyl, imidazolyl, triazolyl, tetrazolyl, 2- or 3-furyl, 2- or 3-thienyl, 1-, 3- or 4-oxazolyl, 3-, 4- or 5-isooxazolyl, etc.

The substituent on each of the substituted aryl group and the substituted heteroaryl group includes unsubstituted alkyl groups, substituted alkyl groups, halogen atoms, nitro group, alkoxycarbonyl groups, carboxyl group, and groups represented by the formula —OR$_5$, —N(R$_6$)R$_7$, —CON(R$_6$)R$_7$, —SO$_2$N(R$_6$)R$_7$ or —S(O)$_n$R$_8$.

When R$_1$, R$_2$, R$_3$ and R$_4$ are independently a group represented by the formula —OR$_5$ wherein R$_5$ is an aromatic group, typical examples of —OR$_5$ are unsubstituted phenoxy group and substituted phenoxy groups. Examples of the substituted phenoxy groups are those having as the substituent, for example, a nitro group, a —N(R$_6$)R$_7$ group (wherein R$_6$ and R$_7$ are independently, for instance, a hydrogen atom or an unsubstituted alkyl group), or a substituted alkyl group having as the substituent, for example, a hydroxyl group or a —N(R$_6$)R$_7$ group. More specific examples of the substituted phenoxy groups are o-, m- or p-nitrophenoxy, o-, m- or p-aminophenoxy, o-, m- or p-(dimethylamino)phenoxy, o-, m- or p-(aminomethyl) phenoxy, and o-, m- or p-(dimethylaminomethyl)phenoxy.

The alkoxy group includes, for example, linear or branched alkoxy groups of 6 or less carbon atoms such as, methoxy, ethoxy, isopropoxy, tert-butoxy, etc.

As the cyclic amino group which R$_6$ and R$_7$ form when taken together with the nitrogen atom to which they are bonded, i.e., the saturated 5- to 7-membered cyclic amino group which may contain another heteroatom in the ring, there may be exemplified 5- to 7-membered cyclic groups containing 1 to 3 nitrogen atoms and 5- to 7-membered cyclic groups containing a nitrogen atom and an oxygen atom. More specific examples of the saturated 5- to 7-membered cyclic amino group are 1-pyrrolidinyl, 1-piperidino, 1-piperazinyl, morpholino and 1-(4-methyl) piperazinyl.

The substituent on the substituted alkyl group includes halogen atoms, hydroxyl group, alkoxy groups, cycloalkyl groups, cyano group, carboxyl group, alkoxycarbonyl groups, acyl groups, aromatic groups, and groups represented by the formula —CONRpRq (wherein Rp and Rq are independently a hydrogen atom or an unsubstituted alkyl group, Rp and Rq being able to be taken together to represent a saturated 5- to 7-membered cyclic amino group which may contain another heteroatom in the ring), —N(R$_6$) R$_7$, or

wherein R" is a hydrogen atom, an unsubstituted alkyl group or a substituted alkyl group, and the ring is a 3- to 8-membered saturated heterocyclic group containing a nitrogen atom. Particularly when R$_1$, R$_2$, R$_3$, R$_4$, R$_5$, R$_8$, R$_{11}$, R$_{12}$, or Z is a substituted alkyl group, the substituent includes, for example, cycloalkyl groups, halogen atoms, hydroxyl group, alkoxy groups, carboxyl group, alkoxycarbonyl groups, acyl groups, aromatic groups and groups represented by the formula —CONRpRq or —N(R$_6$)R$_7$. When R$_6$, R$_7$, R$_9$ or R$_{10}$ is a substituted alkyl group, the substituent includes, for example, cycloalkyl groups, hydroxyl group, alkoxy groups, carboxyl group, alkoxycarbonyl groups, acyl groups, aryl groups, and groups represented by the formula —CONRpRq or —NRpRq. As the alkyl portion of the substituted alkyl group, there may be exemplified the same groups as those exemplified above as the alkyl group.

As such substituted alkyl groups, there may be exemplified substituted alkyl groups of 1 to 5 carbon atoms having as the substituent a cycloalkyl group of 3 to 6 carbon atoms, polyhaloalkyl groups of 1 to 5 carbon atoms, hydroxyalkyl groups of 1 to 6 carbon atoms, alkoxyalkyl groups of 2 to 6 carbon atoms, cyanoalkyl groups of 2 to 6 carbon atoms, carboxyalkyl groups of 2 to 6 carbon atoms, alkoxycarbonylalkyl groups of 3 to 8 carbon atoms, alkanoylalkyl groups of 3 to 8 carbon atoms, aroylalkyl groups of 16 or less carbon atoms, substituted or unsubstituted phenyl- or naphythyl-C1~C5 alkyl groups, carbamoyl-C1~C3 alkyl groups which may have one or two C1~C3 alkyl groups as a substituent(s) on the nitrogen atom, amino-C1~C5 alkyl groups which may have one or two C1~C3 alkyl or C7~C11 aralkyl groups as a substituent(s) on the nitrogen atom, and saturated 5- to 7-membered cyclic amino-C1~C3 alkyl groups.

Typical examples of the substituted alkyl group are polyhaloalkyl groups of 1 to 3 carbon atoms, such as trifluoromethyl, trifluoroethyl, trichloromethyl, etc.; hydroxyalkyl groups of 1 to 6 carbon atoms, such as hydroxymethyl, hydroxyethyl, 1-hydroxyethyl, etc.; aminoalkyl groups of 1 to 5 carbon atoms, such as aminomethyl, aminoethyl, 1-aminoethyl, etc.; alkoxyalkyl groups of 1 to 6 carbon atoms, such as methoxyethyl, ethoxyethyl, methoxypropyl, etc.; carboxyalkyl groups of 2 to 6 carbon atoms, such as carboxyethyl, carboxypropyl, etc.; alkoxycarbonylalkyl groups of 3 to 7 carbon atoms, such as methoxycarbonylmethyl, ethoxycarbonylmethyl, methoxycarbonylethyl, etc.; phenyl- or naphthyl-C1~C5 alkyl groups (which may have in the phenyl or naphthyl portion a substituent such as a C1~C3 alkyl group, halogen atom, nitro group, amino group, hydroxyl group, C1~C3 alkoxy group or the like) such as benzyl, phenylethyl, phenylpropyl, phenylbutyl, 1- or 2-naphthylmethyl, etc.; carbamoyl-C1~C3 alkyl groups which may have one or two C1~C3 alkyl groups as a substituent(s) on the nitrogen atom, for example, carbamoylmethyl, carbamoylethyl, dimethylcarbamoylmethyl, etc.; amino-C1~C5 alkyl groups which may have one or two C1~C3 alkyl or C7~C11 aralkyl groups as a substituent(s) on the nitrogen atom, for example, aminoethyl, aminopropyl, dimethylaminoethyl, dimethylaminopropyl, diethylaminoethyl, N-methyl-N-benzylaminoethyl, etc.; and saturated 5- to 7-membered cyclic amino-C1 C3 alkyl groups such as 1-pyrrolidinylethyl, piperidinoethyl, etc. In the case of $R_6$ and $R_7$, typical examples of the substituted alkyl group are phenyl-C1 C5 alkyl groups such as phenylethyl, etc.

As the substituent on the lower alkylene group for Q and the substituent on the vinyl or ethynyl group for Ra, there may be exemplified unsubstituted alkyl groups, substituted alkyl groups, cycloalkyl groups, cycloalkenyl groups, saturated heterocyclic groups, carboxyl group, alkoxycarbonyl groups, aromatic groups, and groups represented by the formula —$CON(R_6)R_7$.

The lower alkylene group includes, for example, alkylene groups of 6 or less carbon atoms, such as methylene, ethylene, trimethylene, tetramethylene, pentamethylene, hexamethylene, etc.

The acyl group includes, for example, formyl group; alkanoyl groups of 2 to 6 carbon atoms, such as acetyl, propanoyl, etc.; cycloalkanecarbonyl groups of 3 to 6 carbon atoms, such as cyclopropanecarbonyl, cyclobutanecarbonyl, cyclopentanecarbonyl, cyclohexanecarbonyl, etc.; cycloalkenecarbonyl groups of 3 to 6 carbon atoms, such as cyclopentenecarbonyl, cyclohexenecarbonyl, etc.; aroyl groups of 6 to 10 carbon atoms, such as benzoyl, toluoyl, naphthoyl, etc.; saturated heterocyclic ring-carbonyl groups having a 5- or 6-membered saturated heterocyclic group containing one or two heteroatoms selected from the group consisting of nitrogen atom, oxygen atom and sulfur atom, for example, 2-piperidinecarbonyl, 3-morpholinecarbonyl, etc.; and heteroaromatic acyl groups having a 5- or 6-membered heteroaromatic ring containing one or two heteroatoms selected from the group consisting of nitrogen atom, oxygen atom and sulfur atom, for example, furoyl, thenoyl, nicotinoyl, isonicotinoyl, etc.

As the cyclic amino group which Rp and Rq forms when taken together, i.e., the saturated 5- to 7-membered cyclic amino group which may contain another hetero atom in the ring, there may be exemplified the same groups as those exemplified above as the cyclic amino group formed by $R_6$ and $R_7$.

The group represented by the formula —$S(O)_nR_8$ includes, for example, alkylsulfonyl groups of 8 or less carbon atoms, such as methylsulfonyl, ethylsulfonyl, propylsulfonyl, isopropylsulfonyl, etc., and corresponding alkylsulfinyl groups and alkylthio groups.

As the group represented by the formula:

there may be exemplified groups represented by the following formulas:

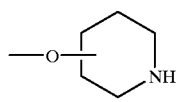 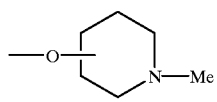

-continued

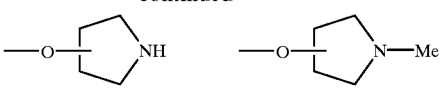

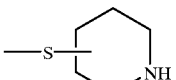 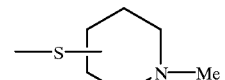

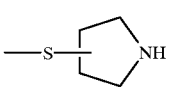 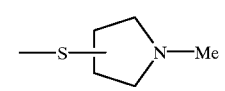

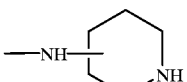 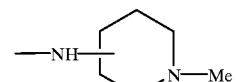

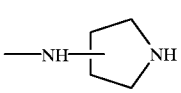 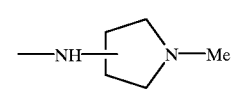

Preferable examples of said group are (piperidin-3-yl)oxy, (piperidin-4-yl)oxy, (1-methylpiperidin-3-yl)oxy, (1-methylpiperidin-4-yl)oxy, (pyrrolidin-3-yl)oxy, (1-methylpyrrolidin-3-yl)oxy, (piperidin-3-yl)thio, (piperidin-4-yl)thio, (1-methylpiperidin-3-yl)thio, (1-methylpiperidin-4-yl)thio, (pyrrolidin-3-yl)thio, (1-methylpyrrolidin-2-yl)thio, (piperidin-3-yl)amino, (piperidin-4-yl)amino, (1-methylpiperidin-3-yl)amino, (1-methylpiperidin-4-yl)amino, (pyrrolidin-3-yl)amino and (1-methylpyrrolidin-3-yl)amino.

The alkenyl group includes, for example, alkenyl groups of 6 or less carbon atoms, such as vinyl, allyl, propenyl, 2-propenyl, butenyl, pentenyl, hexenyl, etc.

The alkynyl group includes, for example, alkynyl groups of 6 or less carbon atoms, such as ethynyl, propargyl, butynyl, pentynyl, etc.

As $Y_1$, $Y_2$, $Y_3$, $Y_4$, $Y_5$, $Y_6$ and $Y_7$, the following may be exemplified.

1. One of $Y_1$ through $Y_7$ is —$CH_2$—, —O—, —CO—, —C(=C($R_{11}$)$R_{12}$)—, —S(O)$_n$— or —N($R_{10}$)—, another is —$CH_2$—, and the five others, which may be the same or different, are independently a single bond or —$CH_2$—. More specific examples of $Y_1$ through $Y_7$ are as follows.

1-1. $Y_1$ is —$CH_2$—, —O—, —CO—, —C(=C($R_{11}$)$R_{12}$)—, —S(O)$_n$— or —N($R_{10}$)—, $Y_2$ is —$CH_2$—, and $Y_3$ through $Y_7$, which may be the same or different, are independently a single bond or —$CH_2$—.

1-2. $Y_7$ is —O—, —CO— or —C(=C($R_{11}$)$R_{12}$)—, $Y_6$ is —$CH_2$—, and $Y_1$ through $Y_5$, which may be the same or different, are independently a single bond or —$CH_2$—.

1-3. $Y_1$ and $Y_7$ are independently —$CH_2$—, one of $Y_2$, $Y_3$, $Y_4$, $Y_5$ and $Y_6$ is —$CH_2$—, —O—, —C(=C($R_{11}$)$R_{12}$)—, —S(O)$_n$— or —N($R_{10}$)—, and the four others, which may be the same or different, are independently a single bond or —$CH_2$—.

1-4. $Y_1$ is —$CH_2$—, —O—, —CO—, —C(=C($R_{11}$)$R_{12}$)—, —S(O)$_n$— or —N($R_{10}$)—, $Y_2$ through $Y_4$ are independently —$CH_2$—, and $Y_5$ and $Y_6$ are independently a single bond.

2. Any adjacent two members of a group consisting of $Y_1$ through $Y_6$ are taken together to represent —CH=CH—, the four others, which may be the same or different, are independently a single bond or —$CH_2$—, and $Y_7$ is a single bond, —O—, —CO—, —C(=C($R_{11}$)$R_{12}$)— or —$CH_2$—.

More specific examples of $Y_1$ through $Y_7$ are as follows.

2-1. —$Y_1$—$Y_2$— is —CH=CH—.

2-2. $Y_1$ is —$CH_2$—, and —$Y_2$—$Y_3$— is —CH=CH—.

2-3. $Y_1$ and $Y_2$ are independently —$CH_2$—, and —$Y_3$—$Y_4$— is —CH=CH—.

2-4. $Y_1$, $Y_2$ and $Y_3$ are independently —$CH_2$—, and —$Y_4$—$Y_5$— is —CH=CH—.

3. $Y_1$ is —O— or —N($R_{10}$)—, one of $Y_2$ through $Y_7$ is —CO—, and the five others, which may be the same or different, are independently a single bond or —$CH_2$—.

More specific examples of $Y_1$ through $Y_7$ are as follows.

3-1. $Y_2$ is —CO—.

3-2. $Y_2$ is —$CH_2$—, and $Y_3$ is —CO—.

3-3. $Y_2$ and $Y_3$ are independently —$CH_2$—, and $Y_4$ is —CO—.

3-4. $Y_2$, $Y_3$ and $Y_4$ are independently —$CH_2$—, and $Y_5$ is —CO—.

3-5. $Y_2$, $Y_3$, $Y_4$ and $Y_5$ are independently —$CH_2$—, and $Y_6$ is —CO—.

Preferable examples of $Y_1$ through $Y_7$ are such that two to five, in particular, two to four, of $Y_1$ through $Y_7$ are independently a single bond and the others independently a group other than a single bond. More preferably, two or three of $Y_1$ through $Y_7$ are independently a single bond, and the other are groups other than a single bond.

In addition, the present invention relates to a process for producing the compound (1). The process comprises reacting a carboxylic acid reactive derivative of the formula (2):

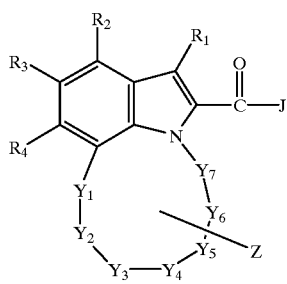

(2)

wherein $R_1$, $R_2$, $R_3$, $R_4$, $Y_1$, $Y_2$, $Y_3$, $Y_4$, $Y_5$, $Y_6$, $Y_7$ and Z are as defined above, and J is a leaving group easily replaceable by a nucleophilic reagent, with guanidine to form the guanidinocarbonyl group (—C(=O)N=C($NH_2$)$_2$ group shown in the formula (1) and, if necessary, converting the reaction product to a pharmaceutically acceptable acid addition salt.

In the above reaction, when the acid derivative of the formula (2) has a reactive group such as hydroxyl group or amino group, the reactive group is previously protected with a suitable protective group, and the protective group is removed after carrying out the reaction, whereby a desired acylguanidine derivative (1) may be produced.

As the carboxylic acid reactive derivative of the formula (2), there may be exemplified acid halides, acid anhydrides (including mixed acid anhydrides) and ester derivatives. Specific examples of the carboxylic acid reactive derivative are acid halides such as acid chlorides and acid bromides; mixed acid anhydrides of an alkyloxychloride type compound (e.g. ethyloxy-carbonyl chloride or isobutyloxycarbonyl chloride) and an α-polyalkyl-substituted carboxylic acid chloride type compound (e.g. diethylacetyl chloride or trimethylacetyl chloride); and ester derivatives such as active esters (e.g. p-nitrophenyl esters, N-hydroxysuccinimide esters and pentafluorophenyl esters) and common esters (e.g. methyl esters and ethyl esters). Such a carboxylic acid reactive derivative can easily be obtained from a corresponding carboxylic acid according to a conventional method.

When guanidine is reacted with an acid halide or an acid anhydride (including a mixed acid anhydride), the reaction may be carried out in a solvent in the presence of a base or excess guanidine with cooling or at room temperature. As the base, there may be exemplified inorganic bases such as sodium hydroxide, potassium hydroxide, sodium carbonate, potassium carbonate, sodium hydrogencarbonate, etc.; and organic bases such as triethylamine, pyridine, etc. As the solvent, there may be exemplified aromatic hydrocarbon solvents such as benzene, toluene, xylene, etc.; ether solvents such as tetrahydrofuran, 1,4-dioxane, etc.; halogenated hydrocarbon solvents such as dichloromethane, chloroform, 1,2-dichloroethane, etc.; amide solvents such as dimethylformamide, dimethylacetamide, etc.; basic solvents such as pyridine, etc.; and mixed solvents thereof.

When guanidine is reacted with an ester derivative, the reaction is carried out in a solvent in the presence of an equimolar or excess amount of guanidine with heating or cooling. When the ester derivative is an active ester, the reaction is preferably carried out, for example, in an ether solvent (e.g. tetrahydrofuran, 1,2-dimethoxyethane or dioxane), an ester solvent (e.g. ethyl acetate), dimethylformamide, or a mixed solvent thereof. When the ester derivative is other than active esters, the reaction is preferably carried out, for example, in an alcohol solvent (e.g. methanol, ethanol or isopropanol), an ether solvent (e.g. tetrahydrofuran, 1,2-dimethoxyethane or dioxane), dimethylformamide, or a mixed solvent thereof. After the solvent is distilled off, the residue may be heated for a short time at about 130° C. if necessary.

The compound (1) of the present invention may be obtained by reacting a carboxylic acid of the general formula (3):

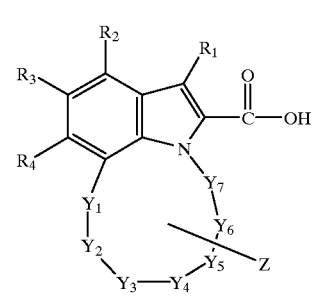

(3)

wherein $R_1$, $R_2$, $R_3$, $R_4$, $Y_1$, $Y_2$, $Y_3$, $Y_4$, $Y_5$, $Y_6$, $Y_7$ and Z are as defined above, with guanidine preferably in the presence of a condensing agent in an inert solvent at room temperature or with heating.

In this reaction, when the compound of the formula (3) has a reactive group such as carboxyl group, hydroxyl group or amino group, the reactive group is previously protected with a suitable protective group, and the protective group is removed after carrying out the reaction, whereby a desired acylguanidine derivative (1) may be produced.

The reaction is preferably carried out in the presence of a condensing agent [e.g. dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphoniume.hexafluorophosphate (BOP), diphenylphosphonylazide (DPPA), N,N-carbonyldiimidazole (Angew. Chem. Int. Ed. Engl., Vol. 1, 351(1962)] and optionally an additive [N-hydroxysuccinimide (HONSu), 1-hydroxybenzotriazole (HOBt) or 3-hydroxy-4-oxo-3,4-dihydro-1,2,3-benzotriazine (HOObt)] in an aromatic hydrocarbon solvent (e.g benzene, toluene or xylene), an ether solvent (e.g. tetrahydrofuran or 1,4-dioxane), a halogenated hydrocarbon solvent (dichloromethane, chloroform or 1,2-dichloroethane), an amide solvent (dimethylformamide) or dimethylacetamide), a basic solvent (e.g. pyridine) or a mixed solvent thereof.

In the above-mentioned production, as the protective group for protecting the reactive group such as hydroxyl group, amino group or carboxyl group, an ordinary protective group used in the field of organic synthetic chemistry may be used. The introduction and removal of such a protective group may be carried out by a usual method (for example, Protective Groups in Organic Synthesis, JOHN WILLEY & SONS, 1991).

For example, as a protective group for the hydroxyl group, methoxymethyl group, tetrahydropyranyl group and the like may be exemplified. As a protective group for the amino group, tert-butoxycarbonyl group and the like may be exemplified. The protective group for the hydroxyl group may be removed by reaction in a solvent such as aqueous methanol, aqueous ethanol or aqueous tetrahydrofuran in the presence of an acid such as hydrochloric acid, sulfuric acid or acetic acid. The protective group for the amino group may be removed by reaction in a solvent such as aqueous tetrahydrofuran, methylene chloride, chloroform or aqueous methanol in the presence of an acid such as hydrochloric acid or trifluoroacetic acid.

As a protective form for protecting the carboxyl group, there may be exemplified tert-butyl esters, orthoesters and acid amides. Such a protective group is removed as follows. In the case of the tert-butyl ester, the removal is carried out, for example, by reaction in an aqueous solvent in the presence of hydrochloric acid. In the case of the orthoester, the removal is carried out by treatment with an acid and then an alkali such as sodium hydroxide in a solvent such as aqueous methanol, aqueous tetrahydrofuran or aqueous 1,2-dimethoxyethane. In the case of the acid amide, the removal is carried out by reaction in a solvent such as water, aqueous methanol or aqueous tetrahydrofuran in the presence of an acid such as hydrochloric acid or sulfuric acid.

The tricyclic indole-2-carboxylic acids of the general formula (2) and the general formula (3), i.e., the starting compounds in the above-mentioned production processes, respectively, are well known in literature (e.g. J. Chem. Soc., Perkin Trans. 1(1992), (6)679–683; Japanese Patent Unexamined Publication Nos. 2-273678 and 3-41068; J. Chem. Soc., Perkin Trans. 1(1987), (9)2079–2090; and J. Am. Chem. Soc. (1958), 80, 5574–5575) or may be produced by a process similar to a process for producing a well-known compound. The carboxylic acid of the general formula (3) can easily be derived from an ester of the general formula (1d) by a conventional hydrolysis reaction. The carboxylic acid reactive derivative of the general formula (2) may be synthesized from the carboxylic acid of the general formula (3) according to a conventional method. A process for synthesizing the ester of the general formula (1d) is described below.

Synthesis Process-1

The compound of the general formula (1d) may be synthesized according to the following reaction formula:

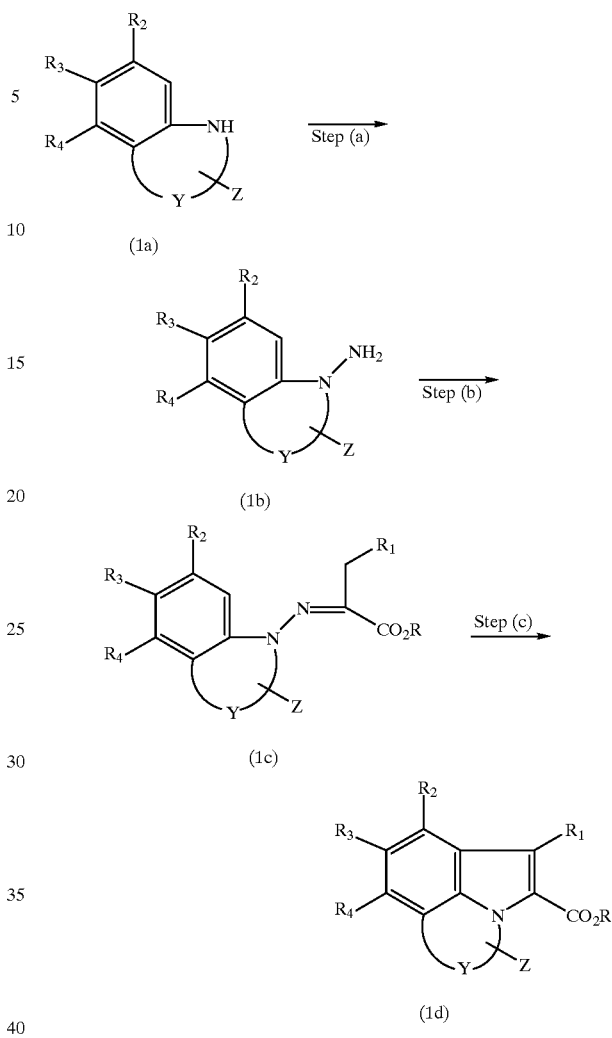

wherein $R_1$, $R_2$, $R_3$, $R_4$ and Z are as defined above, —Y— is —$Y_1$—$Y_2$—$Y_3$—$Y_4$—$Y_5$—$Y_6$—$Y_7$—, and R is a lower alkyl group.

The step (a) consists of N-nitrosation of a compound (1a) and reduction of the resulting nitroso compound. First, the N-nitrosation of the compound (1a) may be carried out by reacting the compound (1a) with sodium nitrite in an organic acid (e.g. acetic acid), a mineral acid or an aqueous medium containing either of these acids. The subsequent reduction of the N-nitroso compound may be carried out using lithium aluminum hydride as a reducing agent in a solvent inert to the reaction (e.g. diethyl ether or tetrahydrofuran). Alternatively, the reduction may be carried out by the use of metallic zinc in the presence of an acid, or the reduction may be carried out by catalytic hydrogenation.

Usually, the step (b) and the step (c) may be carried out by adopting the well-known indole synthesis process of Fischer. In this case, a hydrazone (1c) is produced as an intermediate by the condensation of a compound (1b) with a pyruvic acid ester derivative (1e):

wherein $R_1$ and R are as defined above. The hydrazone (1c) is further condensed to give a compound of the general formula (1d).

Synthesis Process-2

A compound of the general formula (2d) may be synthesized according to the following reaction formula:

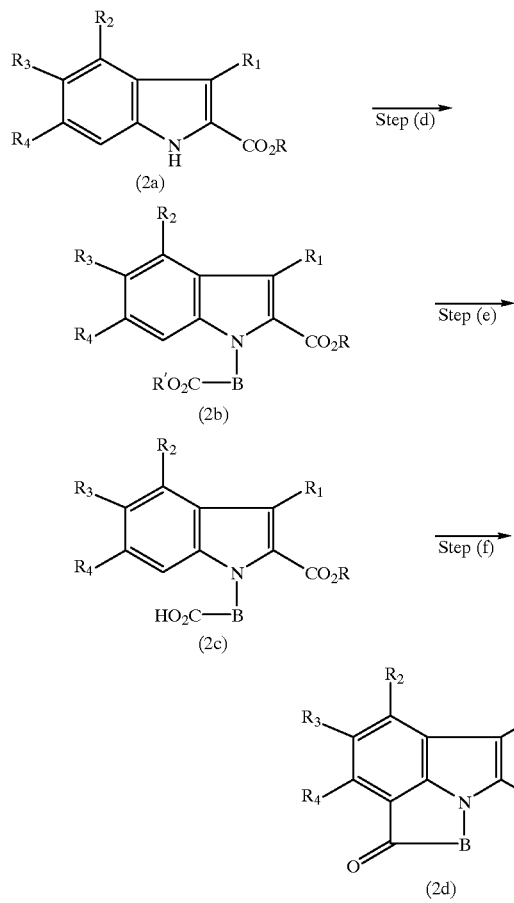

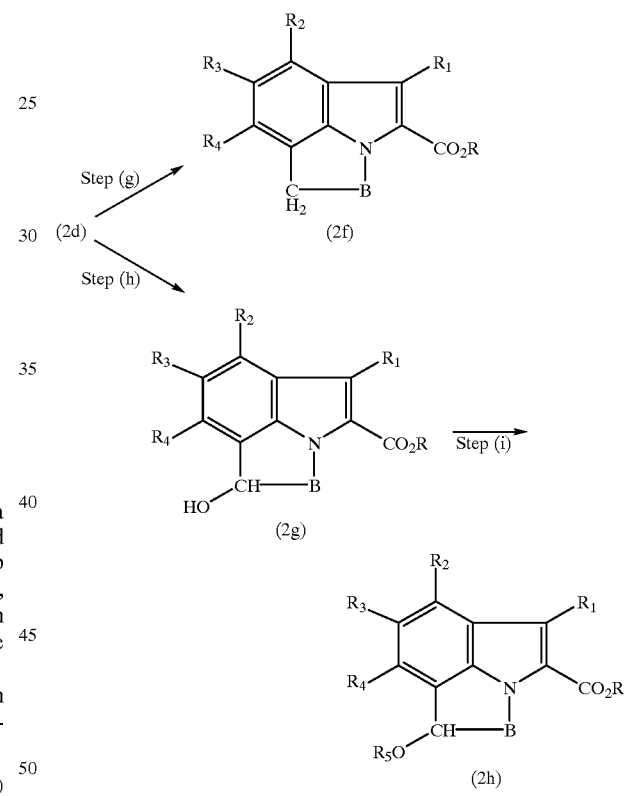

wherein $R_1$, $R_2$, $R_3$, $R_4$ and R are as defined above, R' is a lower alkyl group, and B is an unsubstituted or substituted alkylene chain of 2 to 6 carbon atoms (one methylene group in the alkylene chain may be replaced by an oxygen atom, a sulfur atom or a nitrogen atom, provided that the oxygen atom, sulfur atom or nitrogen atom is not adjacent to the ester group ($CO_2R'$ group)).

The step (d) may be carried out by reacting a well-known indole-2-carboxylic acid derivative (2a) or that conventionally prepared by known methods with a compound (2e):

wherein R' and B are as defined above, and X is a leaving group such as fluorine, chlorine, bromine, iodine, methanesulfonyloxy, p-toluenesulfonyloxy, trifluromethanesulfonyloxy or the like, in the presence of a base in an inert solvent (e.g. N,N-dimethylformamide, dimethyl sulfoxide or tetrahydrofuran). As the base used in this step, there may be exemplified inorganic bases (e.g. potassium carbonate and sodium carbonate), organic bases (e.g. triethylamine and pyridine) and alkali metal hydrides (e.g. potassium hydride and sodium hydride). Particularly when B has two carbon atoms in the compound (2b), the step (d) may be carried out also by reacting the indole-2-carboxylic acid derivative (2a) with an acrylic acid ester derivative in the presence of a catalytic amount of benzyltrimethylammonium hydroxide (Triton B) in an inert solvent (e.g. N,N-dimethylformamide, dioxane or tetrahydrofuran).

The hydrolysis in the step (e) may be carried out under acidic conditions (for example, acetic acid-sulfuric acid).

The ring-closing reaction in the step (f) may be carried out by employing the generally known Friedel-Crafts reaction. A method for carrying out this step is, for example, as follow: a carboxylic acid (2c) is converted to an acid halide with thionyl chloride, phosphorus pentachloride or the like, after which the acid halide may be subjected to ring-closing reaction by using a Lewis acid such as aluminum chloride, antimony pentachloride, iron trichloride, tin tetrachloride, titanium tetrachloride, zinc chloride, boron trifluoride or the like. As a solvent used in the step (f), there may be used nitrobenzene, 1,2-dichloroethane, chloroform, acetone, tetrahydrofuran, ethyl acetate, etc. As an alternate method, it is possible to carry out the ring-closing reaction by reacting the carboxylic acid (2c) in PPA (a poly-phosphoric phosphoric acid) or PPE (a polyphosphate ester).

Further, the compound (2d) may be converted to any of the compounds (2f), (2g) and (2h) shown in the following scheme:

wherein $R_1$, $R_2$, $R_3$, $R_4$, $R_5$, R and B are as defined above. The reduction in the step (g) can be carried out, for example, by the use of triethylsilane in trifluoroacetic acid.

The reduction in the step (h) may be carried out using, for example, sodium borohydride.

The step (i) may be carried out in the same manner as for the above-mentioned step (d). Alternatively, said step may be also carried out with a dehydration reaction of an acid catalyst such as sulfuric, hydrochloric, aromatic sulfonic acids and alkyl sulfonic acids with the corresponding alcohol ($R_5OH$).

The compound (2d) may be synthesized from the indole-2-carboxylic acid derivative also by the same process as known in literature which is other than the above-mentioned synthesis process. As such a process, there may be exemplified the process described in literature (e.g. Khim, Geterosikl, Soedin, (1979), (6)839–841) and the processes described in the reference examples described hereinafter.

In each of the above-mentioned synthesis processes, when the intermediate compound used in any of the steps has a reactive group such as carboxyl group, hydroxyl group or amino group, the reactive group is previously protected with a suitable protective group, and the protective group is removed if necessary after carrying out the step, whereby a desired compound of the general formula (2) or (3) may be produced.

As the compound of the general formula (1) produced in the manner described above, the following compounds may be exemplified.

TABLE 1

| $R_1$ | $R_2$ | $R_3$ | $R_4$ | -v- | -w- | -x- |
|---|---|---|---|---|---|---|
| H | Cl | H | H | —CH$_2$— | —CH$_2$— | —CH$_2$— |
| H | H | Cl | H | —CH$_2$— | —CH$_2$— | —CH$_2$— |
| H | H | H | Cl | —CH$_2$— | —CH$_2$— | —CH$_2$— |
| H | CF$_3$ | H | H | —CH$_2$— | —CH$_2$— | —CH$_2$— |
| H | H | CF$_3$ | H | —CH$_2$— | —CH$_2$— | —CH$_2$— |
| H | H | H | CF$_3$ | —CH$_2$— | —CH$_2$— | —CH$_2$— |
| H | CH$_3$ | H | H | —CH$_2$— | —CH$_2$— | —CH$_2$— |
| H | H | CH$_3$ | H | —CH$_2$— | —CH$_2$— | —CH$_2$— |
| H | H | H | CH$_3$ | —CH$_2$— | —CH$_2$— | —CH$_2$— |
| H | OCH$_3$ | H | H | —CH$_2$— | —CH$_2$— | —CH$_2$— |
| H | H | OCH$_3$ | H | —CH$_2$— | —CH$_2$— | —CH$_2$— |
| H | H | H | OCH$_3$ | —CH$_2$— | —CH$_2$— | —CH$_2$— |
| F | H | H | H | —CH$_2$— | —CH$_2$— | —CH$_2$— |
| H | F | H | H | —CH$_2$— | —CH$_2$— | —CH$_2$— |
| H | H | F | H | —CH$_2$— | —CH$_2$— | —CH$_2$— |
| H | H | H | F | —CH$_2$— | —CH$_2$— | —CH$_2$— |
| H | Cl | H | H | —CO— | —CH$_2$— | —CH$_2$— |
| H | H | Cl | H | —CO— | —CH$_2$— | —CH$_2$— |
| H | H | H | Cl | —CO— | —CH$_2$— | —CH$_2$— |
| H | CF$_3$ | H | H | —CO— | —CH$_2$— | —CH$_2$— |
| H | H | CF$_3$ | H | —CO— | —CH$_2$— | —CH$_2$— |
| H | H | H | CF$_3$ | —CO— | —CH$_2$— | —CH$_2$— |
| H | CH$_3$ | H | H | —CO— | —CH$_2$— | —CH$_2$— |
| H | H | CH$_3$ | H | —CO— | —CH$_2$— | —CH$_2$— |
| H | H | H | CH$_3$ | —CO— | —CH$_2$— | —CH$_2$— |
| H | OCH$_3$ | H | H | —CO— | —CH$_2$— | —CH$_2$— |
| H | H | OCH$_3$ | H | —CO— | —CH$_2$— | —CH$_2$— |
| H | H | H | OCH$_3$ | —CO— | —CH$_2$— | —CH$_2$— |
| F | H | H | H | —CO— | —CH$_2$— | —CH$_2$— |
| H | F | H | H | —CO— | —CH$_2$— | —CH$_2$— |
| H | H | F | H | —CO— | —CH$_2$— | —CH$_2$— |
| H | H | H | F | —CO— | —CH$_2$— | —CH$_2$— |
| H | Cl | H | H | —CHOH— | —CH$_2$— | —CH$_2$— |
| H | H | Cl | H | —CHOH— | —CH$_2$— | —CH$_2$— |
| H | H | H | Cl | —CHOH— | —CH$_2$— | —CH$_2$— |
| H | CF$_3$ | H | H | —CHOH— | —CH$_2$— | —CH$_2$— |
| H | H | CF$_3$ | H | —CHOH— | —CH$_2$— | —CH$_2$— |
| H | H | H | CF$_3$ | —CHOH— | —CH$_2$— | —CH$_2$— |
| H | CH$_3$ | H | H | —CHOH— | —CH$_2$— | —CH$_2$— |
| H | H | CH$_3$ | H | —CHOH— | —CH$_2$— | —CH$_2$— |
| H | H | H | CH$_3$ | —CHOH— | —CH$_2$— | —CH$_2$— |
| F | H | H | H | —CHOH— | —CH$_2$— | —CH$_2$— |
| H | F | H | H | —CHOH— | —CH$_2$— | —CH$_2$— |
| H | H | F | H | —CHOH— | —CH$_2$— | —CH$_2$— |
| H | H | H | F | —CHOH— | —CH$_2$— | —CH$_2$— |
| H | Cl | H | H | —CH(OCH$_3$)— | —CH$_2$— | —CH$_2$— |
| H | H | Cl | H | —CH(OCH$_3$)— | —CH$_2$— | —CH$_2$— |
| H | H | H | Cl | —CH(OCH$_3$)— | —CH$_2$— | —CH$_2$— |
| H | CF$_3$ | H | H | —CH(OCH$_3$)— | —CH$_2$— | —CH$_2$— |
| H | H | CF$_3$ | H | —CH(OCH$_3$)— | —CH$_2$— | —CH$_2$— |
| H | H | H | CF$_3$ | —CH(OCH$_3$)— | —CH$_2$— | —CH$_2$— |
| H | CH$_3$ | H | H | —CH(OCH$_3$)— | —CH$_2$— | —CH$_2$— |
| H | H | CH$_3$ | H | —CH(OCH$_3$)— | —CH$_2$— | —CH$_2$— |
| H | H | H | CH$_3$ | —CH(OCH$_3$)— | —CH$_2$— | —CH$_2$— |
| F | H | H | H | —CH(OCH$_3$)— | —CH$_2$— | —CH$_2$— |
| H | F | H | H | —CH(OCH$_3$)— | —CH$_2$— | —CH$_2$— |

TABLE 1-continued

| R₁ | R₂ | R₃ | R₄ | -v- | -w- | -x- |
|---|---|---|---|---|---|---|
| H | H | F | H | —CH(OCH₃)— | —CH₂— | —CH₂— |
| H | H | H | F | —CH(OCH₃)— | —CH₂— | —CH₂— |
| H | Cl | H | H | —CO— | —CH(CH₃)— | —CH₂— |
| H | H | Cl | H | —CO— | —CH(CH₃)— | —CH₂— |
| H | H | H | Cl | —CO— | —CH(CH₃)— | —CH₂— |
| H | CF₃ | H | H | —CO— | —CH(CH₃)— | —CH₂— |
| H | H | CF₃ | H | —CO— | —CH(CH₃)— | —CH₂— |
| H | H | H | CF₃ | —CO— | —CH(CH₃)— | —CH₂— |
| H | CH₃ | H | H | —CO— | —CH(CH₃)— | —CH₂— |
| H | H | CH₃ | H | —CO— | —CH(CH₃)— | —CH₂— |
| H | H | H | CH₃ | —CO— | —CH(CH₃)— | —CH₂— |
| F | H | H | H | —CO— | —CH(CH₃)— | —CH₂— |
| H | F | H | H | —CO— | —CH(CH₃)— | —CH₂— |
| H | H | F | H | —CO— | —CH(CH₃)— | —CH₂— |
| H | H | H | F | —CO— | —CH(CH₃)— | —CH₂— |
| H | Cl | H | H | —NH— | —CH₂— | —CH₂— |
| H | H | Cl | H | —NH— | —CH₂— | —CH₂— |
| H | H | H | Cl | —NH— | —CH₂— | —CH₂— |
| H | CF₃ | H | H | —NH— | —CH₂— | —CH₂— |
| H | H | CF₃ | H | —NH— | —CH₂— | —CH₂— |
| H | H | H | CF₃ | —NH— | —CH₂— | —CH₂— |
| H | CH₃ | H | H | —NH— | —CH₂— | —CH₂— |
| H | H | CH₃ | H | —NH— | —CH₂— | —CH₂— |
| H | H | H | CH₃ | —NH— | —CH₂— | —CH₂— |
| F | H | H | H | —NH— | —CH₂— | —CH₂— |
| H | F | H | H | —NH— | —CH₂— | —CH₂— |
| H | H | F | H | —NH— | —CH₂— | —CH₂— |
| H | H | H | F | —NH— | —CH₂— | —CH₂— |
| H | Cl | H | H | —N(CH₃)— | —CH₂— | —CH₂— |
| H | H | Cl | H | —N(CH₃)— | —CH₂— | —CH₂— |
| H | H | H | Cl | —N(CH₃)— | —CH₂— | —CH₂— |
| H | CH₃ | H | H | —N(CH₃)— | —CH₂— | —CH₂— |
| H | H | CH₃ | H | —N(CH₃)— | —CH₂— | —CH₂— |
| H | H | H | CH₃ | —N(CH₃)— | —CH₂— | —CH₂— |
| F | H | H | H | —N(CH₃)— | —CH₂— | —CH₂— |
| H | F | H | H | —N(CH₃)— | —CH₂— | —CH₂— |
| H | H | F | H | —N(CH₃)— | —CH₂— | —CH₂— |
| H | H | H | F | —N(CH₃)— | —CH₂— | —CH₂— |
| H | Cl | H | H | —O— | —CH₂— | —CH₂— |
| H | H | Cl | H | —O— | —CH₂— | —CH₂— |
| H | H | H | Cl | —O— | —CH₂— | —CH₂— |
| H | CF₃ | H | H | —O— | —CH₂— | —CH₂— |
| H | H | CF₃ | H | —O— | —CH₂— | —CH₂— |
| H | H | H | CF₃ | —O— | —CH₂— | —CH₂— |
| H | CH₃ | H | H | —O— | —CH₂— | —CH₂— |
| H | H | CH₃ | H | —O— | —CH₂— | —CH₂— |
| H | H | H | CH₃ | —O— | —CH₂— | —CH₂— |
| F | H | H | H | —O— | —CH₂— | —CH₂— |
| H | F | H | H | —O— | —CH₂ | —CH₂— |
| H | H | F | H | —O— | —CH₂— | —CH₂— |
| H | H | H | F | —O— | —CH₂— | —CH₂— |
| H | Cl | H | H | —S— | —CH₂— | —CH₂— |
| H | CF₃ | H | H | —S— | —CH₂— | —CH₂— |
| H | CH₃ | H | H | —S— | —CH₂— | —CH₂— |
| H | F | H | H | —S— | —CH₂— | —CH₂— |
| H | Cl | H | H | —C(=CH₂)— | —CH₂— | —CH₂— |
| H | H | Cl | H | —C(=CH₂)— | —CH₂— | —CH₂— |
| H | H | H | Cl | —C(=CH₂)— | —CH₂— | —CH₂— |
| H | CF₃ | H | H | —C(=CH₂)— | —CH₂— | —CH₂— |
| H | H | CF₃ | H | —C(=CH₂)— | —CH₂— | —CH₂— |
| H | H | H | CF₃ | —C(=CH₂)— | —CH₂— | —CH₂— |
| H | CH₃ | H | H | —C(=CH₂)— | —CH₂— | —CH₂— |
| H | H | CH₃ | H | —C(=CH₂)— | —CH₂— | —CH₂— |
| H | H | H | CH₃ | —C(=CH₂)— | —CH₂— | —CH₂— |
| F | H | H | H | —C(=CH₂)— | —CH₂— | —CH₂— |

TABLE 1-continued

| R₁ | R₂ | R₃ | R₄ | -v- | -w- | -x- |
|---|---|---|---|---|---|---|
| H | F | H | H | —C(=CH₂)— | —CH₂— | —CH₂— |
| H | H | F | H | —C(=CH₂)— | —CH₂— | —CH₂— |
| H | H | H | F | —C(=CH₂)— | —CH₂— | —CH₂— |
| H | Cl | H | H | —CH=CH— | | —CH₂— |
| H | H | Cl | H | —CH=CH— | | —CH₂— |
| H | H | H | Cl | —CH=CH— | | —CH₂— |
| H | CF₃ | H | H | —CH=CH— | | —CH₂— |
| H | H | CF₃ | H | —CH=CH— | | —CH₂— |
| H | H | H | CF₃ | —CH=CH— | | —CH₂— |
| H | CH₃ | H | H | —CH=CH— | | —CH₂— |
| H | H | CH₃ | H | —CH=CH— | | —CH₂— |
| H | H | H | CH₃ | —CH=CH— | | —CH₂— |
| F | H | H | H | —CH=CH— | | —CH₂— |
| H | F | H | H | —CH=CH— | | —CH₂— |
| H | H | F | H | —CH=CH— | | —CH₂— |
| H | H | H | F | —CH=CH— | | —CH₂— |
| H | Cl | H | H | —C(CH₃)=CH— | | —CH₂— |
| H | H | Cl | H | —C(CH₃)=CH— | | —CH₂— |
| H | H | H | Cl | —C(CH₃)=CH— | | —CH₂— |
| H | CF₃ | H | H | —C(CH₃)=CH— | | —CH₂— |
| H | H | CF₃ | H | —C(CH₃)=CH— | | —CH₂— |
| H | H | H | CF₃ | —C(CH₃)=CH— | | —CH₂— |
| H | CH₃ | H | H | —C(CH₃)=CH— | | —CH₂— |
| H | H | CH₃ | H | —C(CH₃)=CH— | | —CH₂— |
| H | H | H | CH₃ | —C(CH₃)=CH— | | —CH₂— |
| F | H | H | H | —C(CH₃)=CH— | | —CH₂— |
| H | F | H | H | —C(CH₃)=CH— | | —CH₂— |
| H | H | F | H | —C(CH₃)=CH— | | —CH₂— |
| H | H | H | F | —C(CH₃)=CH— | | —CH₂— |

TABLE 2

| R₁ | R₂ | R₃ | R₄ | -y- | -γ- |
|---|---|---|---|---|---|
| H | H | H | H | —CH₂— | —CH₂— |
| H | Cl | H | H | —CH₂— | —CH₂— |
| H | H | Cl | H | —CH₂— | —CH₂— |
| H | H | H | Cl | —CH₂— | —CH₂— |
| H | CF₃ | H | H | —CH₂— | —CH₂— |
| H | H | CF₃ | H | —CH₂— | —CH₂— |
| H | CH₃ | H | H | —CH₂— | —CH₂— |
| H | H | CH₃ | H | —CH₂— | —CH₂— |
| H | H | H | CH₃ | —CH₂— | —CH₂— |
| F | H | H | H | —CH₂— | —CH₂— |
| H | F | H | H | —CH₂— | —CH₂— |
| H | H | F | H | —CH₂— | —CH₂— |
| H | H | H | F | —CH₂— | —CH₂— |
| H | Cl | H | H | —CO— | —CH₂— |
| H | H | Cl | H | —CO— | —CH₂— |
| H | H | H | Cl | —CO— | —CH₂— |
| H | CF₃ | H | H | —CO— | —CH₂— |
| H | H | CF₃ | H | —CO— | —CH₂— |
| H | H | H | CF | —CO— | —CH₂— |
| H | CH₃ | H | H | —CO— | —CH₂— |
| H | H | CH₃ | H | —CO— | —CH₂— |
| H | H | H | CH₃ | —CO— | —CH₂— |
| F | H | H | H | —CO— | —CH₂— |
| H | F | H | H | —CO— | —CH₂— |
| H | H | F | H | —CO— | —CH₂— |
| H | H | H | F | —CO— | —CH₂— |
| H | Cl | H | H | —CHOH— | —CH₂— |
| H | H | Cl | H | —CHOH— | —CH₂— |
| H | H | H | Cl | —CHOH— | —CH₂— |
| H | CF₃ | H | H | —CHOH— | —CH₂— |
| H | H | CF₃ | H | —CHOH— | —CH₂— |
| H | H | H | CF₃ | —CHOH— | —CH₂— |
| H | CH₃ | H | H | —CHOH— | —CH₂— |

TABLE 2-continued

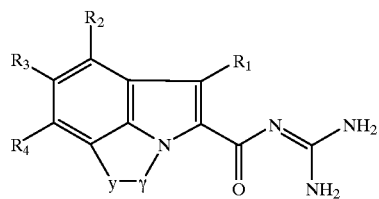

| R₁ | R₂ | R₃ | R₄ | -y- | -γ- |
|---|---|---|---|---|---|
| H | H | CH₃ | H | —CHOH— | —CH₂— |
| H | H | H | CH₃ | —CHOH— | —CH₂— |
| F | H | H | H | —CHOH— | —CH₂— |
| H | F | H | H | —CHOH— | —CH₂— |
| H | H | F | H | —CHOH— | —CH₂— |
| H | H | H | F | —CHOH— | —CH₂— |
| H | Cl | H | H | —CH(OCH₃)— | —CH₂— |
| H | H | Cl | H | —CH(OCH₃)— | —CH₂— |
| H | H | H | Cl | —CH(OCH₃)— | —CH₂— |
| H | CF₃ | H | H | —CH(OCH₃)— | —CH₂— |
| H | H | CF₃ | H | —CH(OCH₃)— | —CH₂— |
| H | H | H | CF₃ | —CH(OCH₃)— | —CH₂— |
| H | CH₃ | H | H | —CH(OCH₃)— | —CH₂— |
| H | H | CH₃ | H | —CH(OCH₃)— | —CH₂— |
| H | H | H | CH₃ | —CH(OCH₃)— | —CH₂— |
| F | H | H | H | —CH(OCH₃)— | —CH₂— |

TABLE 2-continued

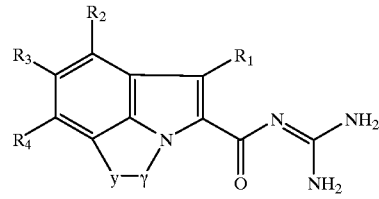

| R₁ | R₂ | R₃ | R₄ | -y- | -γ- |
|---|---|---|---|---|---|
| H | F | H | H | —CH(OCH₃)— | —CH₂— |
| H | H | F | H | —CH(OCH₃)— | —CH₂— |
| H | H | H | F | —CH(OCH₃)— | —CH₂— |
| H | Cl | H | H | —C(=CH₂)— | —CH₂— |
| H | H | Cl | H | —C(=CH₂)— | —CH₂— |
| H | H | H | Cl | —C(=CH₂)— | —CH₂— |
| H | CF₃ | H | H | —C(=CH₂)— | —CH₂— |
| H | H | CF₃ | H | —C(=CH₂)— | —CH₂— |
| H | H | H | CF₃ | —C(=CH₂)— | —CH₂— |
| H | CH₃ | H | H | —C(=CH₂)— | —CH₂— |
| H | H | CH₃ | H | —C(=CH₂)— | —CH₂— |
| H | H | H | CH₃ | —C(=CH₂)— | —CH₂— |
| F | H | H | H | —C(=CH₂)— | —CH₂— |
| H | F | H | H | —C(=CH₂)— | —CH₂— |
| H | H | F | H | —C(=CH₂)— | —CH₂— |
| H | H | H | F | —C(=CH₂)— | —CH₂— |

TABLE 3

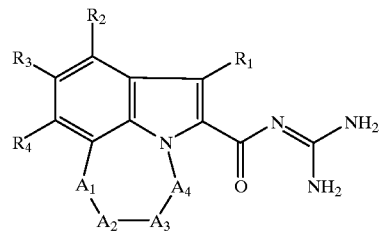

| R₁ | R₂ | R₃ | R₄ | —A₁— | —A₂— | —A₃— | —A₄— |
|---|---|---|---|---|---|---|---|
| H | H | H | H | —CH₂— | —CH₂— | —CH₂— | —CH₂— |
| H | CH₃ | H | H | —CH₂— | —CH₂— | —CH₂— | —CH₂— |
| H | F | H | H | —CH₂— | —CH₂— | —CH₂— | —CH₂— |
| H | Cl | H | H | —CH₂— | —CH₂— | —CH₂— | —CH₂— |
| H | CF₃ | H | H | —CH₂— | —CH₂— | —CH₂— | —CH₂— |
| H | OCH₃ | H | H | —CH₂— | —CH₂— | —CH₂— | —CH₂— |
| H | H | H | H | —CO— | —CH₂— | —CH₂— | —CH₂— |
| H | CH₃ | H | H | —CO— | —CH₂— | —CH₂— | —CH₂— |
| H | F | H | H | —CO— | —CH₂— | —CH₂— | —CH₂— |
| H | Cl | H | H | —CO— | —CH₂— | —CH₂— | —CH₂— |
| H | CF₃ | H | H | —CO— | —CH₂— | —CH₂— | —CH₂— |
| H | OCH₃ | H | H | —CO— | —CH₂— | —CH₂— | —CH₂— |
| H | H | H | H | —CH(OCH₃)— | —CH₂— | —CH₂— | —CH₂— |
| H | CH₃ | H | H | —CH(OCH₃)— | —CH₂— | —CH₂— | —CH₂— |
| H | F | H | H | —CH(OCH₃)— | —CH₂— | —CH₂— | —CH₂— |
| H | Cl | H | H | —CH(OCH₃)— | —CH₂— | —CH₂— | —CH₂— |
| H | CF₃ | H | H | —CH(OCH₃)— | —CH₂— | —CH₂— | —CH₂— |

TABLE 3-continued

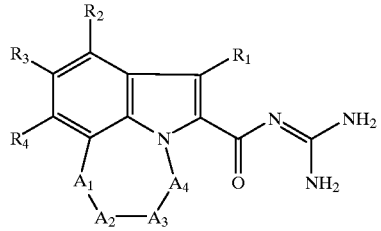

| R₁ | R₂ | R₃ | R₄ | —A₁— | —A₂— | —A₃— | —A₄— |
|---|---|---|---|---|---|---|---|
| H | OCH₃ | H | H | —CH(OCH₃)— | —CH₂— | —CH₂— | —CH₂— |
| H | H | H | H | —CO— | —CH(CH₃)— | —CH₂— | —CH₂— |
| H | CH₃ | H | H | —CO— | —CH(CH₃)— | —CH₂— | —CH₂— |
| H | F | H | H | —CO— | —CH(CH₃)— | —CH₂— | —CH₂— |
| H | Cl | H | H | —CO— | —CH(CH₃)— | —CH₂— | —CH₂— |
| H | CF₃ | H | H | —CO— | —CH(CH₃)— | —CH₂— | —CH₂— |
| H | OCH₃ | H | H | —CO— | —CH(CH₃)— | —CH₂— | —CH₂— |
| H | H | H | H | —NH— | —CH₂— | —CH₂— | —CH₂— |
| H | CH₃ | H | H | —NH— | —CH₂— | —CH₂— | —CH₂— |
| H | F | H | H | —NH— | —CH₂— | —CH₂— | —CH₂— |
| H | Cl | H | H | —NH— | —CH₂— | —CH₂— | —CH₂— |
| H | CF₃ | H | H | —NH— | —CH₂— | —CH₂— | —CH₂— |
| H | OCH₃ | H | H | —NH— | —CH₂— | —CH₂— | —CH₂— |
| H | H | H | H | —N(CH₃)— | —CH₂— | —CH₂— | —CH₂— |
| H | CH₃ | H | H | —N(CH₃)— | —CH₂— | —CH₂— | —CH₂— |
| H | F | H | H | —N(CH₃)— | —CH₂— | —CH₂— | —CH₂— |
| H | Cl | H | H | —N(CH₃)— | —CH₂— | —CH₂— | —CH₂— |
| H | CF₃ | H | H | —N(CH₃)— | —CH₂— | —CH₂— | —CH₂— |
| H | OCH₃ | H | H | —N(CH₃)— | —CH₂— | —CH₂— | —CH₂— |
| H | H | H | H | —O— | —CH₂— | —CH₂— | —CH₂— |
| H | CH₃ | H | H | —O— | —CH₂— | —CH₂— | —CH₂— |
| H | F | H | H | —O— | —CH₂— | —CH₂— | —CH₂— |
| H | Cl | H | H | —O— | —CH₂— | —CH₂— | —CH₂— |
| H | CF₃ | H | H | —O— | —CH₂— | —CH₂— | —CH₂— |
| H | OCH₃ | H | H | —O— | —CH₂— | —CH₂— | —CH₂— |
| H | H | H | H | —C(=CH₂)— | —CH₂— | —CH₂— | —CH₂— |
| H | CH₃ | H | H | —C(=CH₂)— | —CH₂— | —CH₂— | —CH₂— |
| H | F | H | H | —C(=CH₂)— | —CH₂— | —CH₂— | —CH₂— |
| H | Cl | H | H | —C(=CH₂)— | —CH₂— | —CH₂— | —CH₂— |
| H | CF₃ | H | H | —C(=CH₂)— | —CH₂— | —CH₂— | —CH₂— |
| H | OCH₃ | H | H | —C(=CH₂)— | —CH₂— | —CH₂— | —CH₂— |
| H | H | H | H | —CH=CH— | | —CH₂— | —CH₂— |
| H | CH₃ | H | H | —CH=CH— | | —CH₂— | —CH₂— |
| H | F | H | H | —CH=CH— | | —CH₂— | —CH₂— |
| H | Cl | H | H | —CH=CH— | | —CH₂— | —CH₂— |
| H | CF₃ | H | H | —CH=CH— | | —CH₂— | —CH₂— |
| H | OCH₃ | H | H | —CH=CH— | | —CH₂— | —CH₂— |

TABLE 4

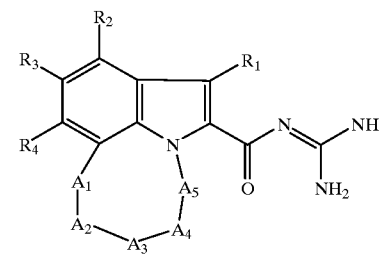

| R₁ | R₂ | R₃ | R₄ | —A₁—A₂—A₃—A₄—A₅— |
|---|---|---|---|---|
| H | H | H | H | —CH₂—CH₂—CH₂—CH₂—CH₂— |
| H | CH₃ | H | H | —CH₂—CH₂—CH₂—CH₂—CH₂— |
| H | F | H | H | —CH₂—CH₂—CH₂—CH₂—CH₂— |
| H | Cl | H | H | —CH₂—CH₂—CH₂—CH₂—CH₂— |
| H | CF₃ | H | H | —CH₂—CH₂—CH₂—CH₂—CH₂— |
| H | OCH₃ | H | H | —CH₂—CH₂—CH₂—CH₂—CH₂— |
| H | H | H | H | —CO—CH₂—CH₂—CH₂—CH₂— |

TABLE 4-continued

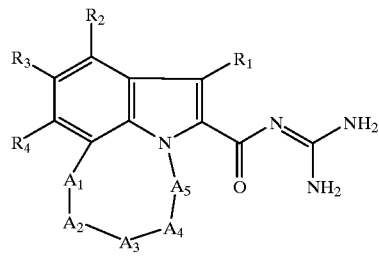

| $R_1$ | $R_2$ | $R_3$ | $R_4$ | —$A_1$—$A_2$—$A_3$—$A_4$—$A_5$— |
|---|---|---|---|---|
| H | CH₃ | H | H | —CO—CH₂—CH₂—CH₂—CH₂— |
| H | F | H | H | —CO—CH₂—CH₂—CH₂—CH₂— |
| H | Cl | H | H | —CO—CH₂—CH₂—CH₂—CH₂— |
| H | CF₃ | H | H | —CO—CH₂—CH₂—CH₂—CH₂— |
| H | OCH₃ | H | H | —CO—CH₂—CH₂—CH₂—CH₂— |
| H | H | H | H | —CH(OCH₃)—CH₂—CH₂—CH₂—CH₂— |
| H | CH₃ | H | H | —CH(OCH₃)—CH₂—CH₂—CH₂—CH₂— |
| H | F | H | H | —CH(OCH₃)—CH₂—CH₂—CH₂—CH₂— |
| H | Cl | H | H | —CH(OCH₃)—CH₂—CH₂—CH₂—CH₂— |
| H | CF₃ | H | H | —CH(OCH₃)—CH₂—CH₂—CH₂—CH₂— |
| H | OCH₃ | H | H | —CH(OCH₃)—CH₂—CH₂—CH₂—CH₂— |
| H | H | H | H | —CO—CH(CH₃)—CH₂—CH₂—CH₂— |
| H | CH₃ | H | H | —CO—CH(CH₃)—CH₂—CH₂—CH₂— |
| H | F | H | H | —CO—CH(CH₃)—CH₂—CH₂—CH₂— |
| H | Cl | H | H | —CO—CH(CH₃)—CH₂—CH₂—CH₂— |
| H | CF₃ | H | H | —CO—CH(CH₃)—CH₂—CH₂—CH₂— |
| H | OCH₃ | H | H | —CO—CH(CH₃)—CH₂—CH₂—CH₂— |
| H | H | H | H | —NH—CH₂—CH₂—CH₂—CH₂— |
| H | CH₃ | H | H | —NH—CH₂—CH₂—CH₂—CH₂— |
| H | F | H | H | —NH—CH₂—CH₂—CH₂—CH₂— |
| H | Cl | H | H | —NH—CH₂—CH₂—CH₂—CH₂— |
| H | CF₃ | H | H | —NH—CH₂—CH₂—CH₂—CH₂— |
| H | OCH₃ | H | H | —NH—CH₂—CH₂—CH₂—CH₂— |
| H | H | H | H | —N(CH₃)—CH₂—CH₂—CH₂—CH₂— |
| H | CH₃ | H | H | —N(CH₃)—CH₂—CH₂—CH₂—CH₂— |
| H | F | H | H | —N(CH₃)—CH₂—CH₂—CH₂—CH₂— |
| H | Cl | H | H | —N(CH₃)—CH₂—CH₂—CH₂—CH₂— |
| H | CF₃ | H | H | —N(CH₃)—CH₂—CH₂—CH₂—CH₂— |
| H | OCH₃ | H | H | —N(CH₃)—CH₂—CH₂—CH₂—CH₂— |
| H | H | H | H | —O—CH₂—CH₂—CH₂—CH₂— |
| H | CH₃ | H | H | —O—CH₂—CH₂—CH₂—CH₂— |
| H | F | H | H | —O—CH₂—CH₂—CH₂—CH₂— |
| H | Cl | H | H | —O—CH₂—CH₂—CH₂—CH₂— |
| H | CF₃ | H | H | —O—CH₂—CH₂—CH₂—CH₂— |
| H | OCH₃ | H | H | —O—CH₂—CH₂—CH₂—CH₂— |
| H | H | H | H | —C(=CH₂)—CH₂—CH₂—CH₂—CH₂— |
| H | CH₃ | H | H | —C(=CH₂)—CH₂—CH₂—CH₂—CH₂— |
| H | F | H | H | —C(=CH₂)—CH₂—CH₂—CH₂—CH₂— |
| H | Cl | H | H | —C(=CH₂)—CH₂—CH₂—CH₂—CH₂— |
| H | CF₃ | H | H | —C(=CH₂)—CH₂—CH₂—CH₂—CH₂— |
| H | OCH₃ | H | H | —C(=CH₂)—CH₂—CH₂—CH₂—CH₂— |
| H | H | H | H | —CH=CH—CH₂—CH₂—CH₂— |
| H | CH₃ | H | H | —CH=CH—CH₂—CH₂—CH₂— |
| H | F | H | H | —CH=CH—CH₂—CH₂—CH₂— |
| H | Cl | H | H | —CH=CH—CH₂—CH₂—CH₂— |
| H | CF₃ | H | H | —CH=CH—CH₂—CH₂—CH₂— |
| H | OCH₃ | H | H | —CH=CH—CH₂—CH₂—CH₂— |
| H | H | H | H | —CH(CH₂OH)—CH₂—CH₂—CH₂—CH₂— |
| H | CH₃ | H | H | —CH(CH₂OH)—CH₂—CH₂—CH₂—CH₂— |
| H | F | H | H | —CH(CH₂OH)—CH₂—CH₂—CH₂—CH₂— |
| H | Cl | H | H | —CH(CH₂OH)—CH₂—CH₂—CH₂—CH₂— |
| H | CF₃ | H | H | —CH(CH₂OH)—CH₂—CH₂—CH₂—CH₂— |
| H | OCH₃ | H | H | —CH(CH₂OH)—CH₂—CH₂—CH₂—CH₂— |
| H | H | H | H | —CH(CH₂OCH₃)—CH₂—CH₂—CH₂—CH₂— |
| H | CH₃ | H | H | —CH(CH₂OCH₃)—CH₂—CH₂—CH₂—CH₂— |
| H | F | H | H | —CH(CH₂OCH₃)—CH₂—CH₂—CH₂—CH₂— |
| H | Cl | H | H | —CH(CH₂OCH₃)—CH₂—CH₂—CH₂—CH₂— |
| H | CF₃ | H | H | —CH(CH₂OCH₃)—CH₂—CH₂—CH₂—CH₂— |
| H | OCH₃ | H | H | —CH(CH₂OCH₃)—CH₂—CH₂—CH₂—CH₂— |
| H | H | H | H | —CH(CH₂NH₂)—CH₂—CH₂—CH₂—CH₂— |
| H | CH₃ | H | H | —CH(CH₂NH₂)—CH₂—CH₂—CH₂—CH₂— |
| H | F | H | H | —CH(CH₂NH₂)—CH₂—CH₂—CH₂—CH₂— |
| H | Cl | H | H | —CH(CH₂NH₂)—CH₂—CH₂—CH₂—CH₂— |

TABLE 4-continued

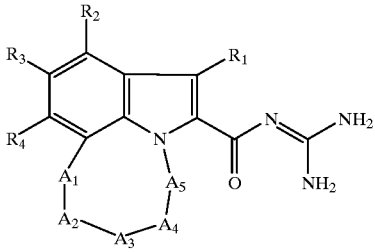

| $R_1$ | $R_2$ | $R_3$ | $R_4$ | $-A_1-A_2-A_3-A_4-A_5-$ |
|---|---|---|---|---|
| H | CF₃ | H | H | —CH(CH₂NH₂)—CH₂—CH₂—CH₂—CH₂— |
| H | OCH₃ | H | H | —CH(CH₂NH₂)—CH₂—CH₂—CH₂—CH₂— |
| H | H | H | H | —CH(CH₂OH)—CH₂—CH₂—CH₂—CH₂— |
| H | CH₃ | H | H | —CH(CH₂OH)—CH₂—CH₂—CH₂—CH₂— |
| H | F | H | H | —CH(CH₂OH)—CH₂—CH₂—CH₂—CH₂— |
| H | Cl | H | H | —CH(CH₂OH)—CH₂—CH₂—CH₂—CH₂— |
| H | CF₃ | H | H | —CH(CH₂OH)—CH₂—CH₂—CH₂—CH₂— |
| H | OCH₃ | H | H | —CH(CH₂OH)—CH₂—CH₂—CH₂—CH₂— |
| H | H | H | H | —CH(CH₂OCH₃)—CH₂—CH₂—CH₂—CH₂— |
| H | CH₃ | H | H | —CH(CH₂OCH₃)—CH₂—CH₂—CH₂—CH₂— |
| H | F | H | H | —CH(CH₂OCH₃)—CH₂—CH₂—CH₂—CH₂— |
| H | Cl | H | H | —CH(CH₂OCH₃)—CH₂—CH₂—CH₂—CH₂— |
| H | CF₃ | H | H | —CH(CH₂OCH₃)—CH₂—CH₂—CH₂—CH₂— |
| H | OCH₃ | H | H | —CH(CH₂OCH₃)—CH₂—CH₂—CH₂—CH₂— |
| H | H | H | H | —CH(CH₂NH₂)—CH₂—CH₂—CH₂—CH₂— |
| H | CH₃ | H | H | —CH(CH₂NH₂)—CH₂—CH₂—CH₂—CH₂— |
| H | F | H | H | —CH(CH₂NH₂)—CH₂—CH₂—CH₂—CH₂— |
| H | Cl | H | H | —CH(CH₂NH₂)—CH₂—CH₂—CH₂—CH₂— |
| H | CF₃ | H | H | —CH(CH₂NH₂)—CH₂—CH₂—CH₂—CH₂— |
| H | OCH₃ | H | H | —CH(CH₂NH₂)—CH₂—CH₂—CH₂—CH₂— |
| H | H | H | H | —CH(CH₂N(CH₃)₂)—CH₂—CH₂—CH₂—CH₂— |
| H | CH₃ | H | H | —CH(CH₂N(CH₃)₂)—CH₂—CH₂—CH₂—CH₂— |
| H | F | H | H | —CH(CH₂N(CH₃)₂)—CH₂—CH₂—CH₂—CH₂— |
| H | Cl | H | H | —CH(CH₂N(CH₃)₂)—CH₂—CH₂—CH₂—CH₂— |
| H | CF₃ | H | H | —CH(CH₂N(CH₃)₂)—CH₂—CH₂—CH₂—CH₂— |
| H | OCH₃ | H | H | —CH(CH₂N(CH₃)₂)—CH₂—CH₂—CH₂—CH₂— |
| H | H | H | H | —CO—CH₂—O—CH₂—CH₂— |
| H | CH₃ | H | H | —CO—CH₂—O—CH₂—CH₂— |
| H | F | H | H | —CO—CH₂—O—CH₂—CH₂— |
| H | Cl | H | H | —CO—CH₂—O—CH₂—CH₂— |
| H | CF₃ | H | H | —CO—CH₂—O—CH₂—CH₂— |
| H | OCH₃ | H | H | —CO—CH₂—O—CH₂—CH₂— |
| H | H | H | H | —CO—CH₂—NH—CH₂—CH₂— |
| H | CH₃ | H | H | —CO—CH₂—NH—CH₂—CH₂— |
| H | F | H | H | —CO—CH₂—NH—CH₂—CH₂— |
| H | Cl | H | H | —CO—CH₂—NH—CH₂—CH₂— |
| H | CF₃ | H | H | —CO—CH₂—NH—CH₂—CH₂— |
| H | OCH₃ | H | H | —CO—CH₂—NH—CH₂—CH₂— |
| H | H | H | H | —CO—CH₂—N(CH₃)—CH₂—CH₂— |
| H | CH₃ | H | H | —CO—CH₂—N(CH₃)—CH₂—CH₂— |
| H | F | H | H | —CO—CH₂—N(CH₃)—CH₂—CH₂— |
| H | Cl | H | H | —CO—CH₂—N(CH₃)—CH₂—CH₂— |
| H | CF₃ | H | H | —CO—CH₂—N(CH₃)—CH₂—CH₂— |
| H | OCH₃ | H | H | —CO—CH₂—N(CH₃)—CH₂—CH₂— |
| H | CH₂OH | H | H | —CO—CH₂—CH₂—CH₂—CH₂— |
| H | CH₃ | OH | H | —CO—CH₂—CH₂—CH₂—CH₂— |
| H | CH₃ | H | OH | —CO—CH₂—CH₂—CH₂—CH₂— |
| H | Cl | OH | H | —CO—CH₂—CH₂—CH₂—CH₂— |
| H | Cl | H | OH | —CO—CH₂—CH₂—CH₂—CH₂— |
| H | F | OH | H | —CO—CH₂—CH₂—CH₂—CH₂— |
| H | F | H | OH | —CO—CH₂—CH₂—CH₂—CH₂— |
| H | H | H | H | —S—CH₂—CH₂—CH₂—CH₂— |
| H | CH₃ | H | H | —S—CH₂—CH₂—CH₂—CH₂— |
| H | F | H | H | —S—CH₂—CH₂—CH₂—CH₂— |
| H | Cl | H | H | —S—CH₂—CH₂—CH₂—CH₂— |
| H | CF₃ | H | H | —S—CH₂—CH₂—CH₂—CH₂— |
| H | OCH₃ | H | H | —S—CH₂—CH₂—CH₂—CH₂— |
| H | CH₂OH | H | H | —S—CH₂—CH₂—CH₂—CH₂— |
| H | CH₃ | OH | H | —S—CH₂—CH₂—CH₂—CH₂— |
| H | CH₃ | H | OH | —S—CH₂—CH₂—CH₂—CH₂— |
| H | Cl | OH | H | —S—CH₂—CH₂—CH₂—CH₂— |
| H | Cl | H | OH | —S—CH₂—CH₂—CH₂—CH₂— |
| H | F | OH | H | —S—CH₂—CH₂—CH₂—CH₂— |

TABLE 4-continued

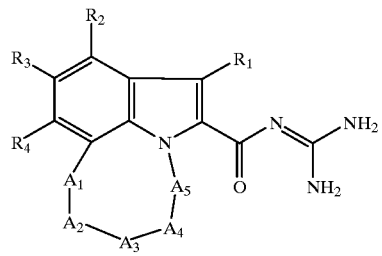

| $R_1$ | $R_2$ | $R_3$ | $R_4$ | $-A_1-A_2-A_3-A_4-A_5-$ |
|---|---|---|---|---|
| H | F | H | OH | $-S-CH_2-CH_2-CH_2-CH_2-$ |
| H | H | H | H | $-SO_2-CH_2-CH_2-CH_2-CH_2-$ |
| H | $CH_3$ | H | H | $-SO_2-CH_2-CH_2-CH_2-CH_2-$ |
| H | F | H | H | $-SO_2-CH_2-CH_2-CH_2-CH_2-$ |
| H | Cl | H | H | $-SO_2-CH_2-CH_2-CH_2-CH_2-$ |
| H | $CF_3$ | H | H | $-SO_2-CH_2-CH_2-CH_2-CH_2-$ |
| H | $OCH_3$ | H | H | $-SO_2-CH_2-CH_2-CH_2-CH_2-$ |
| H | $CH_2OH$ | H | H | $-SO_2-CH_2-CH_2-CH_2-CH_2-$ |
| H | $CH_3$ | OH | H | $-SO_2-CH_2-CH_2-CH_2-CH_2-$ |
| H | $CH_3$ | H | OH | $-SO_2-CH_2-CH_2-CH_2-CH_2-$ |
| H | Cl | OH | H | $-SO_2-CH_2-CH_2-CH_2-CH_2-$ |
| H | Cl | H | OH | $-SO_2-CH_2-CH_2-CH_2-CH_2-$ |
| H | F | OH | H | $-SO_2-CH_2-CH_2-CH_2-CH_2-$ |
| H | F | H | OH | $-SO_2-CH_2-CH_2-CH_2-CH_2-$ |

The substituted guanidine derivative of the present invention has the guanidino moiety shown in the above formula (1) and has tautomers. In detail, there are a tautomer [Ind-C(O)N=C(NH$_2$)$_2$] whose guanidino moiety is diaminomethyleneamino, and another tautomer [Ind-C(O)NH—C(=NH)NH$_2$] whose guanidino moiety is aminoiminomethylamino (in the above formulas, Ind is an indole moiety). These tautomers are different only in state and are the same compound. Therefore, the present invention includes both of the tautomers.

The compound of the general formula (1) includes those having an optical center of asymmetry. The compound having an optical center of asymmetry may be obtained as a racemic modification, or it may be obtained as an optically active substance when an optically active starting material is used. If necessary, the racemic modification obtained may be physically or chemically resolved into optical antipodes by a conventional method. Preferably, diastereomers are formed from the racemic modification by a reaction using a reagent for optical resolution. The diastereomers different in form may be resolved by a conventional method such as fractional crystallization.

If necessary, the compound of the general formula (1) may be made into a pharmaceutically acceptable addition salt with an inorganic acid or an organic acid. As such an acid addition salt, there may be exemplified salts with mineral acids such as hydrochloric acid, hydrobromic acid, sulfuric acid, phosphoric acid, etc.; salts with organic carboxylic acids such as formic acid, acetic acid, fumaric acid, maleic acid, oxalic acid, citric acid, malic acid, tartaric acid, aspartic acid, glutamic acid, etc.; and salts with sulfonic acids such as methanesulfonic acid, benzenesulfonic acid, p-toluenesulfonic acid, hydroxybenzenesulfonic acid, dihydroxybenzenesulfonic acid, etc.

The compound of the general formula (1) and the acid addition salt thereof may be their anhydrides, hydrates or solvates.

The compounds of the present invention have inhibitory effect on the sodium/proton (Na$^+$/H$^+$) exchange transport system and hence are useful as a therapeutic or prophylactic agent for diseases caused by a disorder of the sodium/proton (Na$^+$/H$^+$) exchange transport system, for example, hyperpiesia, organopathies due to ischemia or ischemia re-perfusion, arrhythmia, angina pectoris, diabetes, hypercardia, troubles due to cerebral ischemia, diseases caused by cell over-proliferations, and diseases caused by trouble with endothelial cells.

When used as a therapeutic or prophylactic agent, the compound of the present invention may be orally or parenterally administered. That is, the compound may be orally administered in a usual dosage form such as powder, granules, tablets, capsules, syrup, suspension or the like, or it may be parenterally administered by injection of a solution, emulsion or suspension prepared from the compound. The compound may be administered into rectum in the form of a suppository. The above-exemplified suitable dosage forms may be prepared by blending the active compound with, for example, a carrier, excipient, binder, stabilizer and diluent which are acceptable and ordinary. When the compound is used in the form of an injection, there may be added, for example, a buffer, solubilizer and tonicity agent which are acceptable. Although the dose and the number of repetitions of administration are varied depending on, for example, a disease to be cured, the condition of the disease, age, body weight and administration route, the compound may be administered to an adult in a dose of usually 0.1 to 2,000 mg, preferably 1 to 200 mg per day in 1 to several portions.

The present invention is more concretely illustrated with the following reference examples, examples and test example, which should not be construed as limiting the scope of the invention.

The nomenclature of compounds shown in Reference Examples and Working Examples mentioned below is not always based on IUPAC.

Reference Example 1

Synthesis of ethyl 2,3-dihydro-2-oxo-1H-pyrrolo[1,2,3-de]guinoxaline-5-carboxylate (a) Synthesis of ethyl 1-ethoxycarbonylmethyl-7-nitro-1H-indole-2-carboxylate To a solution of ethyl 7-nitro-1H-indole-2-carboxylate (2.00 g, 8.45 mmol) in N,N-dimethylformamide (50 ml) was added 60% sodium hydride (0.34 g, 8.54 mmol), and the reaction mixture was stirred at room temperature until it became transparent. Then, ethyl bromoacetate (1.43 g, 8.54 mmol) was added and the resulting mixture was stirred at 50–60° C. for 4 hours. The reaction mixture was cooled to room temperature and poured into ice water, followed by extraction with ethyl acetate (three times). The organic layer was washed with water and dried over anhydrous magnesium sulfate. The solvent was distilled off under reduced pressure and the resulting residue was purified by a silica gel column chromatography (eluent: ethyl acetate/n-hexane=5/95) to obtain ethyl 1-ethoxycarbonylmethyl-7-nitro-1H-indole-2-carboxylate (2.11 g).

$^1$Hnmr (CDCl$_3$) δ: 1.29(3H, t, J=7.26 Hz), 1.38–1.43(3H, m), 4.23(2H, dd, J=6.93, 14.19 Hz), 4.38(2H, dd, J=7.26, 14.19 Hz), 5.48(2H, br-s), 7.20–7.26(1H, m), 7.53(1H, s), 7.93–7.98(2H, m).

(b) Synthesis of ethyl 2,3-dihydro-2-oxo-1H-pyrrolo[1,2,3-de]quinoxaline-5-carboxylate Ethyl 1-ethoxycarbonylmethyl-7-nitro-1H-indole-2-carboxylate (2.11 g, 6.59 mmol) was subjected to catalytic reduction in the presence of 10% palladium-carbon (0.20 g) in tetrahydrofuran (70 ml) at ordinary temperature and atmospheric pressure. After completion of the reaction, the catalyst was filtered off and the filtrate was concentrated under reduced pressure. Toluene (100 ml) and sodium methoxide (0.35 g, 6.48 mmol) were added to the residue, and the resulting mixture was heated under reflux for 2 hours. Then, the solvent was distilled off under reduced pressure and the resulting residue was purified by a silica gel column chromatography (eluent: ethyl acetate/n-hexane=2/8) to obtain ethyl 2,3-dihydro-2-oxo-1H-pyrrolo[1,2,3-de]quinoxaline-5-carboxylate (1.38 g).

$^1$Hnmr (CDCl$_3$) δ: 1.39–1.45(3H, m), 4.39(2H, dd, J=7.26, 14.19 Hz), 5.24(2H, s), 6.71(1H, d, J=7.26 Hz), 6.98(1H, dd, J=7.26, 8.25 Hz), 7.23(1H, s), 7.24(1H, dd, J=0.66, 8.24 Hz).

Reference Example 2

Synthesis of ethyl 5,6-dihydro-9-methyl-6-oxo-4H-pyrrolo[3,2,1-ij]quinoline-2-carboxylate (a) Synthesis of ethyl 1-(2-tert-butoxycarbonylethyl)-4-methyl-1H-indole-2-carboxylate A mixture of ethyl 4-methyl-1H-indole-2-carboxylate (70.0 g, 344 mmol), tert-butyl acrylate (53.0 g, 413 mmol), benzyltrimethylammonium hydroxide (5.76 g, 34.4 mmol) and 1,4-dioxane (1,000 ml) was stirred at 60–62° C. for 8.5 hours. The solvent was distilled off under reduced pressure and water (1,000 ml) and acetic acid (30 ml) were added to the residue, followed by extraction with ethyl acetate (twice). The extract solution was washed with a 5% aqueous sodium hydrogencarbonate solution and dried over anhydrous magnesium sulfate. The solvent was distilled off under reduced pressure and the resulting residue was crystallized from isopropanol (230 ml) to obtain ethyl 1-(2-tert-butoxycarbonylethyl)-4-methyl-1H-indole-2-carboxylate (99.2 g). M.p. 78–79° C.

(b) Synthesis of ethyl 1-(2-carboxyethyl)-4-methyl-1H-indole-2-carboxylate

A mixture of ethyl 1-(2-tert-butoxycarbonylethyl)-4-methyl-1H-indole-2-carboxylate (3.76 g, 11.4 mmol), trifluoroacetic acid (14.8 g, 130 mmol) and dichloromethane (50 ml) was stirred at room temperature for 5 hours. The reaction mixture was concentrated under reduced pressure and water was added to the residue, followed by extraction with diethyl ether (three times). The extract solution was washed with a 5% aqueous sodium chloride solution and dried over anhydrous magnesium sulfate. The solvent was distilled off under reduced pressure to obtain ethyl 1-(2-carboxyethyl)-4-methyl-1H-indole-2-carboxylate (3.12 g).

M.p. 133–134° C. (after recrystallization from diisopropyl ether).

(c) Synthesis of ethyl 5,6-dihydro-9-methyl-6-oxo-4H-pyrrolo[3,2,1-ij]quinoline-2-carboxylate A mixture of ethyl 1-(2-carboxyethyl)-4-methyl-1H-indole-2-carboxylate (1.00 g, 3.63 mmol), thionyl chloride (1.35 g, 11.4 mmol) and chloroform (16 ml) was heated under reflux for 5 hours. The reaction mixture was concentrated under reduced pressure and dichloromethane (80 ml) was added to the residue, followed by stirring at room temperature. Subsequently, aluminum chloride (2.02 g, 15.1 mmol) was added and the resulting mixture was stirred at room temperature for 1.5 hours and then heated under reflux for 0.5 hour. The reaction mixture was added to a mixture of water (300 ml) and 35% hydrochloric acid (1.5 ml), followed by extraction with chloroform (three times). The extract solution was washed with water and dried over anhydrous magnesium sulfate. The solvent was distilled off under reduced pressure and the resulting residue was purified by a silica gel column chromatography graphy (eluent: ethyl acetate/n-hexane=3/97) to obtain ethyl 5,6-dihydro-9-methyl-6-oxo-4H-pyrrolo-[3,2,1-ij]quinoline-2-carboxylate (0.53 g).

M.p. 103–104° C. (after recrystallization from isopropanol).

The following compounds were synthesized according to the process described in Reference Example 2.

(1) Ethyl 9-chloro-5,6-dihydro-6-oxo-4H-pyrrolo[3,2,1-ij]quinoline-2-carboxylate
  m.p. 124–125° C. (after recrystallization from isopropanol).

(2) Ethyl 5,6-dihydro-6-oxo-4H-pyrrolo[3,2,1-ij]quinoline-2-carboxylate
  m.p. 131–132° C. (after recrystallization from isopropanol).

(3) Ethyl 5,6-dihydro-7-methyl-6-oxo-4H-pyrrolo[3,2,1-ij]quinoline-2-carboxylate
  m.p. 122–123° C. (after recrystallization from isopropanol).

(4) Ethyl 5,6-dihydro-8-methyl-6-oxo-4H-pyrrolo[3,2,1-ij]quinoline-2-carboxylate
  m.p. 106–107° C. (after recrystallization from isopropanol).

(5) Ethyl 5,6-dihydro-1-methyl-6-oxo-4H-pyrrolo[3,2,1-ij]quinoline-2-carboxylate
  m.p. 106–107° C. (after recrystallization from isopropanol).

Reference Example 3

Synthesis of ethyl 2,3-dihydro-7-methyl-pyrrolo[1,2,3-de]-1,4-benzoxazine-5-carboxylate

(a) Synthesis of ethyl 7-hydroxy-4-methyl-1H-indole-2-carboxylate

A mixture of ethyl 7-benzyloxy-4-methyl-1H-indole-2-carboxylate (15.0 g, 485 mmol), ammonium formate (30.6 g, 485 mmol), 10% palladium-carbon (2.00 g) and ethanol (450 ml) was heated under reflux for 0.5 hour. The reaction mixture was cooled to room temperature, after which the insoluble material was filtered off and the filtrate was concentrated under reduced pressure. The resulting residue was crystallized from ethyl acetate/toluene to obtain ethyl 7-hydroxy-4-methyl-1H-indole-2-carboxylate (6.96 g). M.p. 211–212° C.

(b) Synthesis of ethyl 4-methyl-7-[2-(2-tetrahydro-2H-pyranyl)oxyethoxy]-1H-indole-2-carboxylate A mixture of ethyl 7-hydroxy-4-methyl-1H-indole-2-carboxylate (2.80 g, 12.8 mmol), tetrahydro-2-(2-iodoethoxy)-2H-pyran (4.92 g, 19.2 mmol), potassium carbonate (7.88 g, 57.0 mmol) and acetone (90 ml) was heated under reflux for 16.5 hours. The insoluble material was filtered off, after which the filtrate was concentrated under reduced pressure and the resulting residue was purified by a silica gel column chromatography (eluent: ethyl acetate/n-hexane=3/97) to obtain colorless and oily ethyl 4-methyl-7-[2-(2-tetrahydro-2H-pyranyl)oxyethoxy]-1H-indole-2-carboxylate (3.00 g).

(c) Synthesis of ethyl 7-(2-hydroxyethoxy)-4-methyl-1H-indole-2-carboxylate

Ethyl 4-methyl-7-[2-(2-tetrahydro-2H-pyranyl)oxyethoxy]-1H-indole-2-carboxylate (3.20 g, 9.21 mmol) was dissolved in tetrahydrofuran (70 ml), followed by adding thereto 2N hydrochloric acid (30 ml) at room temperature. The mixture was stirred at room temperature for 3 hours, after which water (200 ml) and then 28% aqueous ammonia were added thereto to neutralize (pH=7 to 8) the reaction mixture. Subsequently, the reaction mixture was extracted twice with ethyl acetate and the extract solution was washed with a 5% aqueous sodium chloride solution and dried over anhydrous magnesium sulfate. The solvent was distilled off under reduced pressure and the resulting residue was crystallized from ethyl acetate to obtain ethyl 7-(2-hydroxyethoxy)-4-methyl-1H-indole-2-carboxylate (1.93 g).

M.p. 166–167° C.

(d) Synthesis of ethyl 7-(2-methanesulfonyloxyethoxy)-4-methyl-1H-indole-2-carboxylate A mixture of ethyl 7-(2-hydroxyethoxy)-4-methyl-1H-indole-2-carboxylate (1.10 g, 4.18 mmol), triethylamine (0.93 g, 9.19 mmol) and dichloromethane (30 ml) was cooled to −10° C., after which methanesulfonyl chloride (0.57 g, 5.01 mmol) was added dropwise with stirring at −10° C. After completion of the dropwise addition, the resulting mixture was stirred at −10° C. for another 2 hours and the reaction mixture was poured into ice water, followed by extraction with chloroform (three times). The extract solution was washed successively with a saturated aqueous ammonium chloride solution, a saturated aqueous sodium hydrogen-carbonate solution and a 5% aqueous sodium chloride solution and dried over anhydrous magnesium sulfate. The solvent was distilled off under reduced pressure to obtain ethyl 7-(2-methanesulfonyloxyethoxy)-4-methyl-1H-indole-2-carboxylate. This compound was used in the subsequent reaction without further purification.

(e) Synthesis of ethyl 2,3-dihydro-7-methyl-pyrrolo[1,2,3-de]-1,4-benzoxazine-5-carboxylate A mixture of ethyl 7-(2-methanesulfonyloxy-ethoxy)-4-methyl-1H-indole-2-carboxylate (1.30 g, 3.81 mmol), 60% sodium hydride (0.15 g, 3.81 mmol) and N,N-dimethylformamide (65 ml) was stirred at room temperature for 8 hours. The reaction mixture was poured into ice water and extracted three times with ethyl acetate, and the extract solution was washed with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=2/98) to obtain ethyl 2,3-dihydro-7-methyl-pyrrolo[1,2,3-de]-1,4-benzoxazine-5-carboxylate (0.87 g).

M.p. 101–102° C. (after recrystallization from isopropanol).

Reference Example 4

Synthesis of ethyl 2,3-dihydro-1-methyl-7-trifluoromethyl-1H-pyrrolo[1,2,3-de]quinoxaline-5-carboxylate

(a) Synthesis of 4-[N-methyl-N-(2-hydroxyethyl)amino]-3-nitrobenzotrifluoride 2-(Methylamino)ethanol (17.3 g, 231 mmol) was added dropwise to a solution of 4-chloro-3-nitrobenzotrifluoride (26.0 g, 115 mmol) in N,N-dimethylformamide (100 ml) at 0° C. After the reaction temperature was raised to room temperature, the reaction mixture was stirred at room temperature for 1 hour, poured into a saturated aqueous ammonium chloride solution, and then extracted twice with ethyl acetate. The organic layer was washed with a 5% aqueous sodium chloride solution and dried over anhydrous magnesium sulfate. The solvent was distilled off under reduced pressure and the resulting residue was purified by a silica gel column chromatography (eluent: chloroform/methanol=97/3) to obtain an oil of 4-[N-methyl-N-(2-hydroxyethyl)amino]-3-nitrobenzotrifluoride.

$^1$Hnmr (CDCl$_3$) δ: 2.04(1H, t, J=5.93 Hz), 2.91(3H, s), 3.53(2H, t, J=5.28 Hz), 3.84(2H, dd, J=5.61, 10.89 Hz), 7.26(1H, d, J=8.91 Hz), 7.60(1H, dd, J=2.31, 8.91 Hz), 8.02(1H, d, J=1.32 Hz).

(b) Synthesis of 4-[N-methyl-N-[2-(2-tetrahydro-2H-pyranyl)oxyethyl]amino]-3-nitrobenzotrifluoride A mixture of 4-[N-methyl-N-(2-hydroxyethyl)amino]-3-nitrobenzotrifluoride (29.0 g, 110 mmol), p-toluenesulfonic acid monohydrate (2.09 g, 11.0 mmol), 3,4-dihydro-2H-pyran (18.5 g, 220 mmol) and tetrahydrofuran (600 ml) was stirred at room temperature for 4.5 hours. Sodium hydrogencarbonate (10 g) was added to the reaction mixture and the resulting mixture was stirred at room temperature for 30 minutes, after which the insoluble materials were filtered off. The filtrate was concentrated under reduced pressure and the resulting residue was purified by a silica gel column chromatography (eluent: ethyl acetate/n-hexane=5/95) to obtain an oil of 4-[N-methyl-N-[2-(2-tetrahydro-2H-pyranyl)oxyethyl]amino]-3-nitrobenzotrifluoride.

¹Hnmr (CDCl₃) δ: 1.47–1.72(6H, m), 2.95(3H, s), 3.45–3.79 (5H, m), 3.92–4.00(1H, m), 4.56–4.58(1H, m), 7.24(1H, d, J=8.90 Hz), 7.54–7.58(1H, m), 7.99(1H, d, J=1.64 Hz).

(c) Synthesis of 2-methyl-4-[N-methyl-N-[2-(2-tetrahydro-2H-pyranyl)oxyethyl]amino]-3-nitrobenzotrifluoride A solution of potassium tert-butoxide (3.22 g, 28.7 mmol) in tetrahydrofuran (40 ml) was added dropwise to a mixture of 4-[N-methyl-N-[2-(2-tetrahydro-2H-pyranyl)oxyethyl] amino]-3-nitrobenzotrifluoride (5.00 g, 14.4 mmol), trimethylsulfonium iodide (5.86 g, 28.7 mmol) and N,N-dimethylformamide (80 ml) with stirring at 15–20° C. After stirring at 15–16° C. for another 1 hour, the reaction mixture was cooled to 0° C. The reaction mixture was poured into cold water and extracted three times with ethyl acetate. The extract solution was washed twice with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=3/97) to obtain an oil of 2-methyl-4-[N-methyl-N-[2-(2-tetrahydro-2H-pyranyl)oxyethyl]amino]-3-nitrobenzotrifluoride.

¹Hnmr (CDCl₃) δ: 1.48–1.76(6H, m), 2.32(3H, d, J=1.32Hz), 2.91(3H, s), 3.35(2H, t, J=5.61 Hz), 3.46–3.57 (2H, m), 3.74–3.90(2H, m), 4.56–4.57(1H, m), 7.07(1H, d, J=8.90 Hz), 7.57(1H, d, J=8.91 Hz).

(d) Synthesis of ethyl [3-[N-methyl-N-[2-(2-tetrahydro-2H-pyranyl)oxyethyl]amino]-2-nitro-6-trifluoromethylphenyl]pyruvate Diethyl oxalate (1.94 g, 13.2 mmol) and then a solution of 2-methyl-4-[N-methyl-N-[2-(2-tetrahydro-2H-pyranyl) oxyethyl]amino]-3-nitrobenzotrifluoride (2.40 g, 6.62 mmol) in tetrahydrofuran (40 ml) were added dropwise to a mixture of potassium ethoxide (1.11 g, 13.2 mmol) and tetrahydrofuran (60 ml) at room temperature. The reaction mixture was stirred at room temperature for 6 hours and then cooled to 3° C., and acetic acid (1.59 g, 26.5 mmol) was added dropwise. The reaction mixture thus obtained was poured into cold water and extracted twice with ethyl acetate. The extract solution was washed with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=1/9) to obtain an oil of ethyl [3-[N-methyl-N-[2-(2-tetrahydro-2H-pyranyl)oxyethyl]amino]-2-nitro-6-trifluoromethylphenyl]pyruvate.

¹Hnmr (CDCl₃) δ: 1.41(3H, t, J=7.26 Hz), 1.50–1.76(6H, m), 2.91(3H, s), 3.42–3.60(4H, m), 3.73–3.82(1H, m), 3.86–3.94(1H, m), 4.27(2H, s), 4.34–4.42(2H, m), 4.56–4.58(1H, m), 7.20(1H, d, J=9.24 Hz), 7.62(1H, d, J=9.24 Hz).

(e) Synthesis of ethyl 7-[N-methyl-N-(2-hydroxyethyl)amino]-4-trifluoromethyl-1H-indole-2-carboxylate A mixture of iron powder (2.42 g, 43.3 mmol) and acetic acid (40 ml) was stirred at 70° C. Then, a solution of ethyl [3-[N-methyl-N-[2-(2-tetrahydro-2H-pyranyl)oxyethyl] amino]-2-nitro-6-trifluoromethylphenyl]pyruvate (2.00 g, 4.33 mmol) in toluene (20 ml) was added dropwise to the aforesaid mixture, followed by stirring at 78–83° C. for 2 hours. The reaction mixture was cooled to 30° C., after which 2N hydrochloric acid (20 ml) and tetrahydrofuran (20 ml) were added and the resulting mixture was stirred at room temperature for 2.5 hours. Subsequently, the reaction mixture was poured into an aqueous ammonia solution and ethyl acetate (300 ml) was added and then stirred. After being separated, the aqueous layer was extracted with ethyl acetate (200 ml) and the combined organic layer was washed with a 5% aqueous sodium chloride solution and then a 5% aqueous sodium hydrogencarbonate solution. The washed organic layer was dried over anhydrous magnesium sulfate and distilled under reduced pressure to remove the solvent, and the resulting residue was purified by a silica gel column chromatography (eluent: ethyl acetate/n-hexane=1/9) to obtain ethyl 7-[N-methyl-N-(2-hydroxyethyl)amino]-4-trifluoromethyl-1H-indole-2-carboxylate.

¹Hnmr (CDCl₃) δ: 1.37–1.42(3H, m), 2.88(3H, s), 3.23 (1H, brs), 3.36(2H, t, J=4.62 Hz), 4.00(2H, brs), 4.32–4.40 (2H, m), 6.73(1H, d, J=7.92 Hz), 7.28–7.35(2H, m), 11.73 (1H, brs).

(f) Synthesis of ethyl 7-[N-methyl-N-(2-methanesulfonyloxyethyl)amino]-4-trifluoromethyl-1H-indole-2-carboxylate A mixture of ethyl 7-[N-methyl-N-(2-hydroxyethyl) amino]-4-trifluoromethyl-1H-indole-2-carboxylate (0.37 g, 1.12 mmol)., triethylamine (0.25 g, 2.46 mmol) and tetrahydrofuran (20 ml) was cooled to −19° C., after which methanesulfonyl chloride (0.14 g, 1.23 mmol) was added dropwise with stirring. The reaction mixture was stirred at −18° C. to −13° C. for 1 hour, poured into cold water, and then extracted three times with ethyl acetate. The extract solution was washed with a 5% aqueous sodium hydrogencarbonate solution and a 5% aqueous sodium chloride solution and dried over anhydrous magnesium sulfate. The solvent was distilled off under reduced pressure to obtain an oil of ethyl 7-[N-methyl-N-(2-methanesulfonyloxyethyl)amino]-4-trifluoromethyl-1H-indole-2-carboxylate.

¹Hnmr (CDCl₃) δ: 1.40–1.43(3H, m), 2.97(3H, s), 3.24 (3H, s), 3.49–3.52(2H, m), 4.39–4.46(2H, m), 4.51–4.55 (2H, m), 6.89(1H, d, J=7.92 Hz), 7.33–7.40(2H, m), 9.70 (1H, brs).

g) Synthesis of ethyl 2,3-dihydro-1-methyl-7-trifluoromethyl-1H-pyrrolo[1,2,3-de]quinoxaline-5-carboxylate A mixture of ethyl 7-[N-methyl-N-(2-methanesulfonyloxyethyl)amino]-4-trifluoromethyl-1H-indole-2-carboxylate (3.15 g, 7.71 mmol), 60% sodium hydride (0.31 g, 7.71 mmol) and N,N-dimethylformamide (200 ml) was stirred at room temperature for 1 hour. The reaction mixture was poured into cold water and extracted with ethyl acetate, and the extract solution was washed with a 5% aqueous sodium chloride solution and dried over anhydrous magnesium sulfate. The solvent was distilled off under reduced pressure and the resulting residue was recrystallized from isopropanol to obtain ethyl 2,3-dihydro-1-methyl-7-trifluoromethyl-1H-pyrrolo[1,2,3-de]quinoxaline-5-carboxylate. M.p. 91–92° C.

¹Hnmr (CDCl₃) δ: 1.39–1.44(3H, m), 3.02(3H, s), 3.50 (2H, t, J=5.28 Hz), 4.34–4.42(2H, m), 4.70(2H, t, J=5.28 Hz), 6.35(1H, d, J=7.92 Hz), 7.29–7.32(2H, m).

Reference Example 5

Synthesis of ethyl 5,6-dihydro-9-methyl-4H-Pyrrolo [3,2,1-ij]quinoline-2-carboxylate Triethylsilane (3.07 g, 26.4 mmol) was added dropwise to a mixture of ethyl 5,6-dihydro-9-methyl-6-oxo-4H-pyrrolo

[3,2,1-ij]quinoline-2-carboxylate (1.70 g, 6.61 mmol) and trifluoroacetic acid (20 ml) at room temperature. Then, the reaction mixture was stirred at room temperature for 3 hours and distilled under reduced pressure to remove the solvent. Ice water was added to the residue, followed by extraction with ethyl acetate (twice). The extract solution was washed with a 5% aqueous sodium hydrogencarbonate solution and then a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=3/97) to obtain 0.87 g of ethyl 5,6-dihydro-9-methyl-4H-pyrrolo[3,2,1-ij]quinoline-2-carboxylate. M.p. 51–52° C. (after recrystallization from n-hexane).

$^1$Hnmr (CDCl$_3$) δ: 1.39–1.44(3H, m), 2.16–2.26(2H, m), 2.52 (3H, s), 2.92–2.96(2H, m), 4.34–4.41(2H, m), 4.52–4.56(2H, m), 6.82(1H, d, J=7.26 Hz), 6.92(1H, d, J=6.92 Hz), 7.23(1H, s).

The following compounds were synthesized according to the process described in Reference Example 5.

(1) Ethyl 5,6-dihydro-10-methyl-4H-azepino[3,2,1-hi]indole-2-carboxylate $^1$Hnmr (CDCl$_3$) δ: 1.39–1.44(3H, m), 2.03–2.26(4H, m), 2.49 (3H, s), 3.08–3.13(2H, m), 4.36(2H, dd, J=7.26, 14.19 Hz), 4.74–4.78(2H, m), 6.77(1H, dd, J=0.99, 6.92 Hz), 6.91(1H, d, J=7.26 Hz), 7.26(1H, s).

(2) Ethyl 5,6-dihydro-9-chloro-4H-pyrrolo[3,2,1-ij]quinoline-2-carboxylate m.p. 87–88° C. (after recrystallization from n-hexane).

$^1$Hnmr (CDCl$_3$) δ: 1.39–1.44(3H, m), 2.17–2.24(2H, m), 2.29–2.97(2H, m), 4.38(2H, dd, J=7.26, 14.19 Hz), 4.52–4.56(2H, m), 6.90–6.93(1H, m), 7.03(1H, d, J=7.26 Hz), 7.27(1H, s).

(3) Ethyl 5,6-dihydro-10-chloro-4H-azepino[3,2,1-hi]indole-2-carboxylate m.p. 44–45° C. (after recrystallization from isopropanol).

$^1$Hnmr (CDCl$_3$) δ: 1.41(3H, t, J=7.26 Hz), 2.03–2.23(4H, m), 3.08–3.12(2H, m), 4.36(2H, dd, J=6.93, 14.19 Hz), 4.76–4.80(2H, m), 6.90(1H, d, J=7.59 Hz), 6.98(1H, d, J=7.59 Hz), 7.31(1H, s).

(4) Ethyl 5,6-dihydro-4H-azepino[3,2,1-hi]indole-2-carboxylate $^1$Hnmr (CDCl$_3$) δ: 1.40(3H, t, J=7.26 Hz), 2.08–2.23(4H, m), 3.12–3.16(2H, m), 4.35(2H, dd, J=7.26, 14.18 Hz), 4.74–4.78(2H, m), 6.95–7.02(2H, m), 7.24(1H, s), 7.42–7.47(1H, m).

Reference Example 6

Synthesis of ethyl 5,6-dihydro-10-methyl-7-oxo-4H-azepino[3,2,1-hi]indole-2-carboxylate (a) Synthesis of ethyl 1-(3-ethoxycarbonylpropyl)-4-methyl-1H-indole-2-carboxylate A mixture of ethyl 4-methyl-1H-indole-2-carboxylate (8.50 g, 41.8 mmol), 60% sodium hydride (1.67 g, 41.8 mmol) and N,N-dimethylformamide (150 ml) was stirred at room temperature until the reaction mixture became transparent. Subsequently, ethyl 4-bromobutyrate (8.16 g, 41.8 mmol) was added dropwise to the aforesaid mixture and the resulting mixture was stirred at 27–29° C. for another 8 hours. The reaction mixture was poured into ice water and extracted with ethyl acetate, and the extract solution was washed with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=3/97) to obtain ethyl 1-(3-ethoxycarbonylpropyl)-4-methyl-1H-indole-2-carboxylate.

$^1$Hnmr (CDCl$_3$) δ: 1.21–1.27(3H, m), 1.40–1.45(3H, m), 2.04–2.19(2H, m), 2.30–2.35(2H, m), 2.56 (3H, m), 4.12 (2H, dd, J=7.26, 14.19 Hz), 4.33–4.41(2H, m), 4.60–4.65 (2H, m), 6.91–6.94(1H, m), 7.18–7.27(2H, m), 7.34(1H, d, J=0.66 Hz).

(b) Synthesis of ethyl 1-(3-carboxypropyl)-4-methyl-1H-indole-2-carboxylate

A mixture of ethyl 1-(3-ethoxycarboxypropyl)-4-methyl-1H-indole-2-carboxylate (15.4 g, 48.5 mmol), acetic acid (250 ml) and 30% sulfuric acid (125 ml) was stirred at 70–75° C. for 1.5 hours. The reaction mixture was cooled to room temperature and then poured into ice water, followed by extraction with ethyl acetate (twice). Subsequently, the organic layer was extracted with aqueous ammonia (prepared from 130 ml of 28% aqueous ammonia and 100 ml of water), and the aqueous layer thus obtained was adjusted to pH 3 to 4 with 35% hydrochloric acid. The solid precipitated was collected by filtration, washed with water and then dried under reduced pressure to obtain 9.2 g of ethyl 1-(3-carboxypropyl)-4-methyl-1H-indole-2-carboxylate.

M.p. 132–133° C. (after recrystallization from acetonitrile).

$^1$Hnmr (CDCl$_3$) δ: 1.42(3H, t, J=7.26 Hz), 2.10–2.20(2H, m), 2.40(2H, t, J=7.26 Hz), 2.55(3H, d, J=0.66 Hz), 4.37(2H, dd, J=7.26, 14.19 Hz), 4.62–4.67(2H, m), 6.92–6.95(1H, m), 7.21–7.28(2H, m), 7.34(1H, s).

(c) Synthesis of ethyl 5,6-dihydro-10-methyl-7-oxo-4H-azepino[3,2,1,-hi]indole-2-carboxylate A mixture of diphosphorus pentaoxide (100 g) and 85% phosphoric acid (100 g) was stirred at 80° C. Then, ethyl 1-(3-carboxypropyl)-4-methyl-1H-indole-2-carboxylate (8.50 g, 31.3 mmol) was added to the aforesaid mixture and the resulting mixture was stirred at 80–83° C. for 1 hour. The reaction mixture was cooled to 40° C. and ice water was added, followed by extraction with diethyl ether (twice). The extract solution was washed with a 5% aqueous sodium hydrogencarbonate solution and then a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=3/97) to obtain 7.21 g of ethyl 5,6-dihydro-10-methyl-7-oxo-4H-azepino[3,2,1-hi]indole-2-carboxylate.

M.p. 96–97° C. (after recrystallization from isopropanol).

$^1$Hnmr (CDCl$_3$) δ: 1.41–1.46(3H, m), 2.29–2.38(2H, m), 2.61 (3H, s), 3.07–3.11(2H, m), 4.35–4.43(2H, m), 4.81–4.85(2H, m), 7.03(1H, dd, J=0.66, 7.59 Hz), 7.44(1H, s), 8.05(1H, d, J=7.59 Hz).

The following compounds were synthesized according to the process described in Reference Example 6.

(1) Ethyl 5,6-dihydro-7-oxo-4H-azepino[3,2,1-hi]indole-2-carboxylate m.p. 86–88° C. (after recrystallization from isopropanol).

(2) Ethyl 10-chloro-5,6-dihydro-7-oxo-4H-azepino[3,2,1-hi]indole-2-carboxylate m.p. 119–120° C. (after recrystallization from isopropanol).

Reference Example 7

Synthesis of ethyl 5,6-dihydro-6-hydroxy-9-methyl-4H-pyrrolo[3,2,1-ij]quinoline-2-carboxylate Ethyl 5,6-dihydro-9-methyl-6-oxo-4H-pyrrolo[3,2,1-ij] quinoline-2-carboxylate (3.00 g, 11.7 mmol) was added to a mixture of tetrahydrofuran (20 ml) and ethanol (80 ml), and the reaction mixture was cooled to 0° C. Then, sodium borohydride (0.44 g, 11.7 mmol) was added and the resulting mixture was stirred at 0° C. for 1 hour. The reaction mixture was concentrated under reduced pressure, and ethyl acetate and then a 5% aqueous sodium hydroxide solution were added to the residue. After being separated, the aqueous layer was further extracted twice with ethyl acetate, and the combined organic layer was washed with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=1/9) to obtain 2.40 g of ethyl 5,6-dihydro-6-hydroxy-9-methyl-4H-pyrrolo-[3,2,1-ij]-quinoline-2-carboxylate.

$^1$Hnmr (CDCl$_3$) δ: 1.40–1.45(3H, m), 1.74(1H, d, J=4.28 Hz), 2.17–2.39(2H, m), 2.55(3H, s), 4.39(2H, dd, J=7.26, 14.19 Hz), 4.42–4.52(1H, m), 4.77–4.86(1H, m), 5.05–5.08 (1H, m), 6.90–6.93(1H, m), 7.18(1H, d, J=6.93 Hz), 7.28 (1H, s).

Reference Example 8

Synthesis of ethyl 5-fluoro-4-methyl-1H-indole-2-carboxylate (a) Synthesis of ethyl 3-(3-fluoro-2-methylphenyl)-2-azidopropenoate A solution of sodium ethoxide (11.1 g, 163 mmol) in ethanol (100 ml) was cooled to −45° C. and then a solution of 3-fluoro-2-methylbenzaldehyde (9.00 g, 65.2 mmol) and ethyl azidoacetate (21.0 g, 163 mmol) in tetrahydrofuran (30 ml) were slowly added dropwise therein. The reaction temperature of the mixture was raised from −35° C. to −10° C. over 5 hours and the reaction solution was poured in a cooled aqueous ammonium chloride solution. The resulting mixture was extracted with ethyl acetate and the extract was washed with a saturated ammonium chloride solution and then 5% aqueous sodium chloride solution followed by drying over anhydrous magnesium sulfate. The solvent was distilled off under reduced pressure and the resulting residue was treated with silica gel column chromatography (eluated with ethyl acetate/n-hexane=3/97) to give 10.0 g of ethyl 3-(3-fluoro-2-methylphenyl)-2-azidopropenoate.

(b) Synthesis of ethyl 5-fluoro-4-methyl-1H-indole-2-carboxylate

A solution of ethyl 3-(3-fluoro-2-methylphenyl)-2-azidopropenoate (10.0 g, 40.1 mmol) in o-xylene (100 ml) was slowly added dropwise in o-xylene (500 ml) at a temperature of 110° C. under stirring. The mixture was stirred at 120–122° C. for 5 hours and the solvent was distilled off under reduced pressure. The residue obtained was recrystallized from isopropyl-alcohol (60 ml) to give 3.58 g of ethyl 5-fluoro-4-methyl-1H-indole-2-carboxylate.

Melting point: 148–149° C.

$^1$H nmr (CDCl$_3$) δ: 1.43(3H, t, J=7.26 Hz), 2.46(3H, d, J=1.98 Hz), 4.38–4.46(2H, m), 7.01–7.08 (1H, m), 7.16–7.26 (2H, m), 8.99 (1H, br-s).

In accordance with the process shown in Reference Example 8, the following compounds were synthesized:

(1) Ethyl 4,5-difluoro-1H-indole-2-carboxylate
Melting point: 174–175° C. (recrystallized from mixed solvents of diethylether/n-hexane)

(2) Ethyl 5-chloro-4-methyl-1H-indole-2-carboxylate
Melting point: 169–170° C. (recrystallized from isopropyl alcohol)

(3) Ethyl 4,6-dimethyl-1H-indole-2-carboxylate
Melting point: 116–118° C. (recrystallized from diisopropyl ether)

(4) Ethyl 4,5-dichloro-1H-indole-2-carboxylate
Melting point: 75–77° C. (recrystallized from isopropyl alcohol)

(5) Ethyl 4-chloro-5-methoxy-1H-indole-2-carboxylate
Melting point: 176–177° C. (recrystallized from isopropyl alcohol)

(6) Ethyl 6-benzyloxy-4-chloro-1H-indole-2-carboxylate
Melting point: 152–154° C. (recrystallized from isopropyl alcohol)

EXAMPLE 1

Synthesis of N-(aminoiminomethyl)-5,6-dihydro-9-methyl-6-oxo-4H-pyrrolo[3,2,1-ij]quinoline-2-carboxamide methanesulfonate

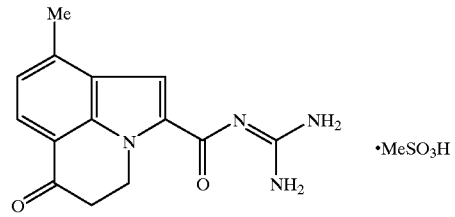

A mixture of ethyl 5,6-dihydro-9-methyl-6-oxo-4H-pyrrolo[3,2,1-ij]quinoline-2-carboxylate (0.65 g, 2.53 mmol), guanidine hydrochloride (1.21 g, 12.6 mmol), sodium methoxide (0.68 g, 12.6 mmol) and N,N-dimethylformamide (35 ml) was stirred at room temperature for 18 hours. The reaction mixture was poured into a 10% aqueous sodium chloride solution and extracted three times with ethyl acetate, and the extract solution was washed with a 5% aqueous sodium chloride solution and dried over anhydrous magnesium sulfate. The solvent was distilled off under reduced pressure to obtain crude N-(aminoiminomethyl)-5,6-dihydro-6-oxo-9-methyl-4H-pyrrolo[3,2,1-ij]quinoline-2-carboxamide. This crude product was added to a mixture of aqueous isopropanol and methanesulfonic acid (0.47 g, 4.89 mmol) and dissolved therein by heating, and the resulting solution was cooled to 0° C. The crystals precipitated were collected by filtration and then recrystallized from water to obtain N-(aminoiminomethyl)-5,6-dihydro-9-methyl-6-oxo-4H-pyrrolo[3,2,1-ij]quinoline-2-carboxamide methanesulfonate (0.57 g).

M.p. 267–268° C. (decomp.).

EXAMPLE 2

Synthesis of N-(aminoiminomethyl)-2,3-dihydro-7-methyl-pyrrolo[1,2,3-de]-1,4-benzoxazine-5-carboxamide methanesulfonate

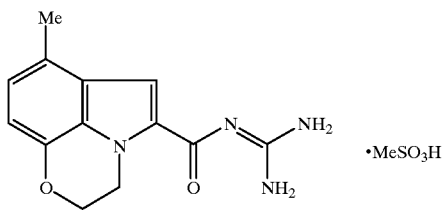

N-(aminoiminomethyl)-2,3-dihydro-7-methyl-pyrrolo[1,2,3-de]-1,4-benzoxazine-5-carboxamide methanesulfonate (0.55 g) was obtained by carrying out reaction according to the method described in Example 1, except for using ethyl 2,3-dihydro-7-methyl-pyrrolo[1,2,3-de]-1,4-benzoxazine-5-carboxylate (0.60 g, 2.45 mmol), guanidine hydrochloride (1.17 g, 12.2 mmol), sodium methoxide (0.66 g, 12.2 mmol) and N,N-dimethylformamide (30 ml).

M.p. 268–269° C. (decomp.).

EXAMPLE 3

Synthesis of N-(aminoiminomethyl)-5,6-dihydro-4H-pyrrolo[3,2,1-ij]quinoline-2-carboxamide methanesulfonate

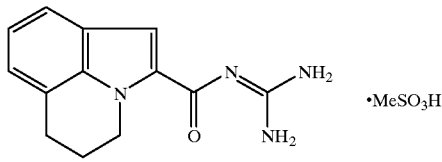

N-(aminoiminomethyl)-5,6-dihydro-4H-pyrrolo[3,2,1-ij]quinoline-2-carboxamide methanesulfonate (0.43 g) was obtained by carrying out reaction according to the method described in Example 1, except for using ethyl 5,6-dihydro-4H-pyrrolo[3,2,1-ij]-quinoline-2-carboxylate (1.00 g, 4.36 mmol), guanidine hydrochloride (2.08 g, 21.8 mmol), sodium methoxide (1.18 g, 21.8 mmol) and N,N-dimethylformamide (30 ml).

M.p. 233–234° C. (decomp.).

EXAMPLE 4

Synthesis of N-(aminoiminomethyl)-2,3-dihydro-2-oxo-1H-pyrrolo[1,2,3-de]quinoxaline-5-carboxamide hydrochloride

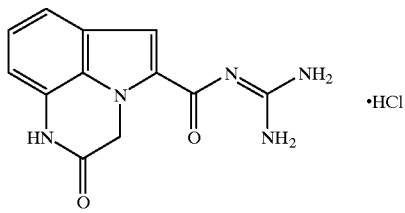

Guanidine hydrochloride (5.39 g, 56.5 mmol) was added to a solution of sodium methoxide (3.05 g, 56.5 mmol) in methanol (60 ml), and the resulting mixture was stirred at room temperature for 30 minutes. The sodium chloride precipitated was filtered off and to the thus obtained solution was added ethyl 2,3-dihydro-2-oxo-1H-pyrrolo[1,2,3-de]quinoxaline-5-carboxylate (1.38 g, 5.65 mmol), after which a large portion of the methanol was distilled off under reduced pressure. The resulting residue was stirred with heating at 130° C. for 5 minutes and allowed to stand at room temperature for 1 hour. Water was added to the reaction mixture, followed by extraction with ethyl acetate (three times). The extract solution was washed with water and dried over anhydrous magnesium sulfate. The solvent was distilled off under reduced pressure and the resulting residue was purified by a silica gel column chromatography (eluent: chloroform/methanol=95/5) to obtain N-(aminoiminomethyl)-2,3-dihydro-2-oxo-1H-pyrrolo[1,2,3-de]-quinoxaline-5-carboxamide. Subsequently, this compound was hydrochlorinated into N-(aminoiminomethyl)-2,3-dihydro-2-oxo-1H-pyrrolo[1,2,3-de]quinoxaline-5-carboxamide hydrochloride (1.19 g) with hydrochloric acid/methanol.

M.p. 328–329° C. (decomp.).

The following compounds of Examples 5 to 16 were synthesized by carrying out reaction according to the method described in Example 1.

EXAMPLE 5

N-(aminoiminomethyl)-2,3-dihydro-1-methyl-7-trifluoromethyl-1H-pyrrolo[1,2,3-de]quinoxaline-5-carboxamide methanesulfonate

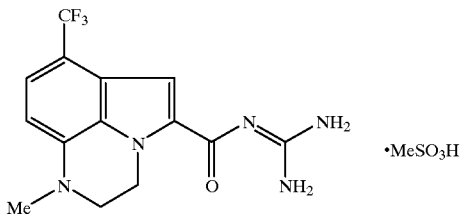

m.p. 211–212° C. (decomp.).

EXAMPLE 6

N-(aminoiminomethyl)-4,5-dihydropyrrolo[3,2,1-hi]indole-2-caboxamide methanesulfonate

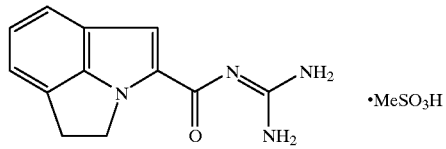

m.p. 257–258° C. (decomp.).

EXAMPLE 7

N-(aminoiminomethyl)-5,6-dihydro-8-methyl-6-oxo-4H-pyrrolo[3,2,1-ij]quinoline-2-carboxamide methanesulfoante

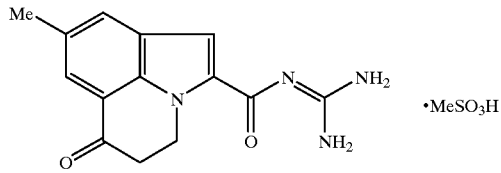

m.p. 257–258° C. (decomp.).

EXAMPLE 8

N-(aminoiminomethyl)-5,6-dihydro-7-methyl-6-oxo-4H-pyrrolo[3,2,1-ij]quinoline-2-carboxamide methanesulfoante

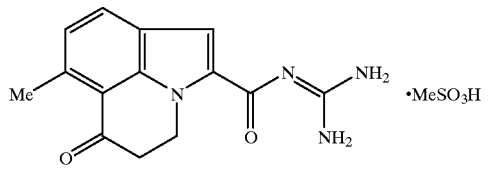

m.p. 284–285° C. (decomp.).

EXAMPLE 9

N-(aminoiminomethyl)-5,6-dihydro-1-methyl-6-oxo-4H-pyrrolo[3,2,1-ij]quinoline-2-carboxamide methanesulfonate

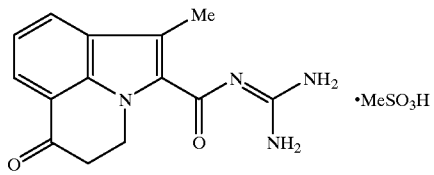

m.p. 251–252° C. (decomp.).

EXAMPLE 10

N-(aminoiminomethyl)-5,6-dihydro-9-methyl-4H-pyrrolo[3,2,1-ij]quinoline-2-carboxamide methanesulfoante

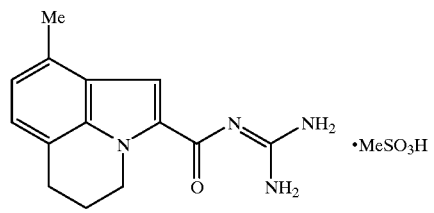

m.p. 247–248° C. (decomp.).

EXAMPLE 11

N-(aminoiminomethyl)-5,6-dihydro-10-methyl-7-oxo-4H-azepino[3,2,1-hi]indole-2-carboxamide methanesulfonate

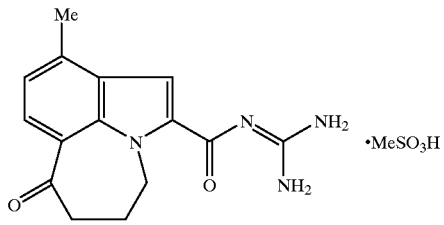

m.p. 261–262° C. (decomp.).

EXAMPLE 12

N-(aminoiminomethyl)-5,6-dihydro-10-methyl-4H-azepino[3,2,1-hi]indole-2-carboxamide methanesulfonate

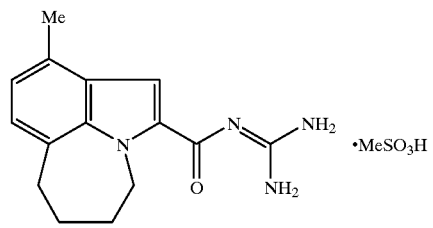

m.p. 244–245° C. (decomp.).

EXAMPLE 13

N-(aminoiminomethyl)-5,6-dihydro-6-oxo-4H-pyrrolo[3,2,1-ij]quinoline-2-carboxamide methanesulfonate

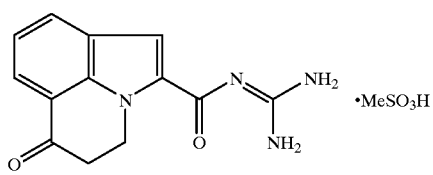

m.p. 273–274° C. (decomp.).

EXAMPLE 14

N-(aminoiminomethyl)-10-chloro-5,6-dihydro-7-oxo-4H-azepino[3,2,1-hi]indole-2-carboxamide methanesulfonate

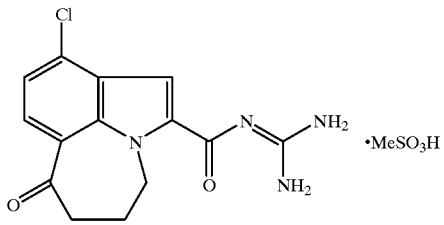

m.p. 276–277° C. (decomp.).

EXAMPLE 15

N-(aminoiminomethyl)-5,6-dihydro-7-oxo-4H-zepino[3,2,1-hi]indole-2-carboxamide methanesulfonate

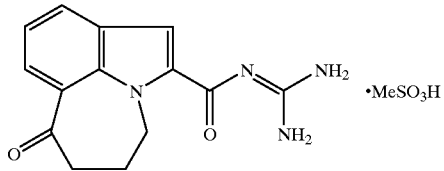

m.p. 266–267° C. (decomp.).

EXAMPLE 16

N-(aminoiminomethyl)-9-chloro-5,6-dihydro-6-oxo-4H-pyrrolo[3,2,1-ij]quinoline-2-carboxamide methanesulfonate

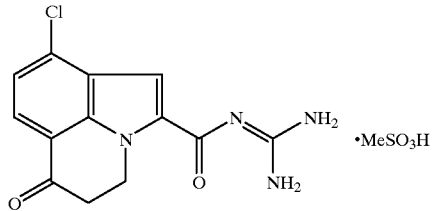

m.p. 278–279° C. (decomp.).

EXAMPLE 17

Synthesis of N-(aminoiminomethyl)-5,6-dihydro-9-methyl-6-methoxy-4H-pyrrolo[3,2,1-ij]quinoline-2-carboxamide methanesulfonate

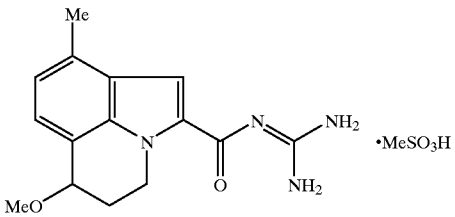

(a) Synthesis of ethyl 5,6-dihydro-9-methyl-6-methoxy-4H-pyrrolo[3,2,1-ij]quinoline-2-carboxylate Methyl iodide (0.55 g, 3.86 mmol) was added dropwise to a mixture of ethyl 5,6-dihydro-6-hydroxy-9-methyl-4H-pyrrolo[3,2,1-ij]quinoline-2-carboxylate (0.50 g, 1.93 mmol), 60% sodium hydride (0.08 g, 1.93 mmol) and tetrahydrofuran (20 ml) with stirring at room temperature, and the resulting mixture was stirred at room temperature for another 2 hours. The reaction mixture was poured into ice water and extracted three times with ethyl acetate, and the extract solution was washed with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=5/95) to obtain 0.31 g of ethyl 5,6-dihydro-9-methyl-6-methoxy-4H-pyrrolo[3,2,1-ij]quinoline-2-carboxylate.

$^1$Hnmr (CDCl$_3$) δ: 1.42(3H, t, J=7.26 Hz), 2.09–2.21(1H, m), 2.40–2.49(1H, m), 2.55(3H, s), 3.39(3H, s), 4.31–4.42 (3H, m), 4.50–4.52(1H, m), 4.82–4.90(1H, m), 6.87–6.90 (1H, m), 7.11(1H, d, J=6.93 Hz), 7.27(1H, s).

(b) Synthesis of N-(aminoiminomethyl)-5,6-dihydro-9-methyl-6-methoxy-4H-pyrrolo[3,2,1-ij] quinoline-2-carboxamide methanesulfonate N-(aminoiminomethyl)-5,6-dihydro-9-methyl-6-methoxy-4H-pyrrolo[3,2,1-ij]quinoline-2-carboxamide methanesulfonate was obtained by carrying out reaction according to the method described in Example 1, except for using ethyl 5,6-dihydro-9-methyl-6-methoxy-4H-pyrrolo[3,2,1-ij]quinoline-2-carboxylate (1.20 g, 4.39 mmol), guanidine hydrochloride (4.19 g, 43.9 mmol), sodium methoxide (2.37 g, 43.9 mmol) and N,N-dimethylformamide (60 ml). In the present example, the desired compound was crystallized from a mixed solvent of tetrahydrofuran and diethyl ether.

$^1$Hnmr (DMSO-d6) δ: 2.06–2.15(1H, m), 2.24–2.41(4H, m), 3.31(3H, s), 4.18–4.28(1H, m), 4.53–4.56(1H, m), 4.69–4.75(1H, m), 6.95(1H, dd, J=0.99, 6.93 Hz), 7.20(1H, d, J=7.26 Hz), 7.50(1H, s), 8.31(4H, brs), 11.18(1H, brs).

| Elementary analysis (for $C_{15}H_{18}N_4O_2 \cdot CH_4SO_3$): | | | |
|---|---|---|---|
| | C | H | N |
| Calcd. (%) | 50.25 | 5.80 | 14.65 |
| Found (%) | 50.01 | 5.88 | 14.34 |

EXAMPLE 18

Synthesis of N-(aminoiminomethyl)-5,6-dihydro-6-isopropoxy-9-methyl-4H-pyrrolo[3,2,1-ij]quinoline-2-carboxamide methanesulfonate

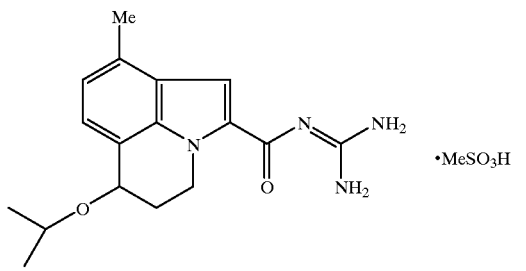

Crude N-(aminoiminomethyl)-5,6-dihydro-6-hydroxy-9-methyl-4H-pyrrolo[3,2,1-ij]quinoline-2-carboxamide was obtained by carrying out reaction according to the method described in Example 1, except for using ethyl 5,6-dihydro-6-hydroxy-9-methyl-4H-pyrrolo[3,2,1-ij]quinoline-2-carboxylate (0.70 g, 2.70 mmol), guanidine hydrochloride (2.58 g, 27.0 mmol), sodium methoxide (1.46 g, 27.0 mmol) and N,N-dimethylformamide (40 ml). This compound was dissolved in a solution of methanesulfonic acid (1.0 g) in isopropanol (50 ml) and the resulting solution was stirred at 60° C. for 30 minutes. Subsequently, the reaction solution was poured into ice water, made basic with 28% aqueous ammonia and then extracted three times with ethyl acetate. The extract solution was washed with a 5% aqueous sodium chloride solution and dried over anhydrous magnesium sulfate. The solvent was distilled off under reduced pressure and the resulting residue was purified by a silica gel column chromatography (eluent: chloroform/methanol=97/3) to obtain 0.37 g of N-(aminoiminomethyl)-5,6-dihydro-6-isopropoxy-9-methyl-4H-pyrrolo[3,2,1-ij]quinoline-2-carboxamide. This compound was treated with methanesulfonic acid (0.29 g) in a mixed solvent of tetrahydrofuran and diethyl ether to obtain N-(aminoiminomethyl)-5,6-dihydro-6-isopropoxy-9-methyl-4H-pyrrolo[3,2,1-ij]quinoline-2-carboxamide methanesulfonate.

m.p. 162–163° C. (decomp.).

| Elementary analysis (for $C_{17}H_{22}N_4O_2 \cdot CH_4SO_3$): | | | |
|---|---|---|---|
| | C | H | N |
| Calcd. (%) | 52.67 | 6.38 | 13.65 |
| Found (%) | 52.33 | 6.42 | 13.36 |

The following compounds of Examples 19 to 21 were synthesized by carrying out reaction according to the method described in Example 1.

EXAMPLE 19

N-(aminoiminomethyl)-5,6-dihydro-9-chloro-4H-pyrrolo[3,2,1-ij]quinoline-2-carboxamide methanesulfonate

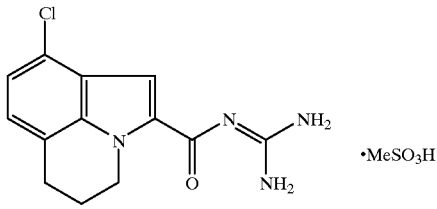

m.p. 267–268° C. (after recrystallization from a mixed solvent of water and isopropanol).

EXAMPLE 20

N-(aminoiminomethyl)-5,6-dihydro-10-chloro-4H-azepino[3,2,1-hi]indole-2-carboxamide methanesulfonate

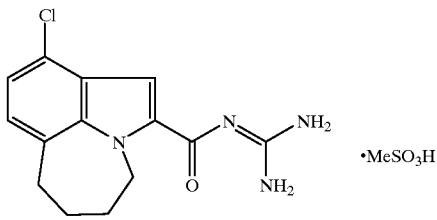

m.p. 244–245° C. (after recrystallization from a mixed solvent of water and isopropanol).

EXAMPLE 21

N-(aminoiminomethyl-5,6-dihydro-4H-azepino[3,2,1-hi]indole-2-carboxamide methanesulfonate

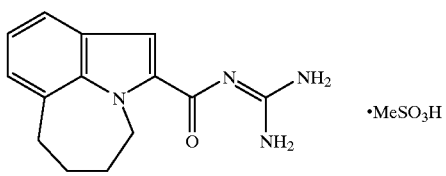

m.p. 240–241° C.

EXAMPLE 22

Synthesis of N-(aminoiminomethyl)-5,6,7,8-tetrahydro-11-chloro-8-oxo-4H-azocino[3,2,1-hi]indole-2-carboxamide methanesulfonate monohydrate

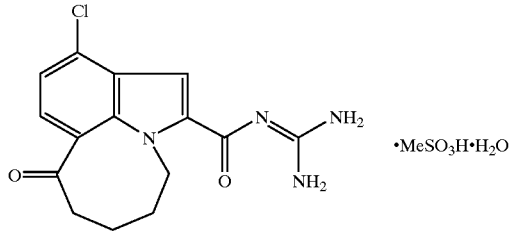

(a) Synthesis of ethyl 1-(4-ethoxycarbonylbutyl)-4-chloro-1H-indole-2-carboxylate 13.2 Grams of ethyl 1-(4-ethoxycarbonylbutyl)-4-chloro-1H-indole-2-carboxylate was obtained by carrying out reaction according to the method described in Reference Example 6, (a), except for using ethyl 4-chloro-1H-indole-2-carboxylate (8.85 g, 39.6 mmol), 60% sodium hydride (1.58 g, 39.6 mmol), ethyl 5-bromovalerate (9.10 g, 43.5 mmol) and N,N-dimethylformamide (100 ml).

$^1$Hnmr (CDCl$_3$) δ: 1.20–1.25(3H, m), 1.39-1.45(3H, m), 1.62–1.89(4H, m), 2.32(2H, t, J=7.26 Hz), 4.10(2H, dd, J=7.26, 14.19 Hz), 4.34–4.42(2H, m), 4.54–4.59(2H, m), 7.13(1H, dd, J=1.32, 6.93 Hz), 7.20–7.30(2H, m), 7.38(1H, s).

(b) Synthesis of ethyl 1-(4-carboxybutyl)-4-chloro-1H-indole-2-carboxylate 9.10 Grams of ethyl 1-(4-carboxybutyl)-4-chloro-1H-indole-2-carboxylate was obtained by carrying out reaction according to the method described in Reference Example 6, (b), except for using ethyl 1-(4-ethoxycarbonylbutyl)-4-chloro-1H-indole-2-carboxylate (12.50 g, 35.5 mmol), acetic acid (250 ml) and 30% sulfuric acid (125 ml).

M.p. 93–94° C. (after recrystallization from acetonitrile).

$^1$Hnmr (CDCl$_3$) δ: 1.39–1.45(3H, m), 1.63–1.92(4H, m), 2.39(2H, t, J=7.26 Hz), 4.34–4.42(2H, m), 4.58(2H, t, J=7.26 Hz), 7.14(1H, dd, J=1.32, 6.93 Hz), 7.21–7.30(2H, m), 7.39(1H, d, J=0.66 Hz).

(c) Synthesis of ethyl 5,6,7,8-tetrahydro-11-chloro-8-oxo-4H-azocino[3,2,1-hi]indole-2-carboxylate 6.50 Grams of ethyl 5,6,7,8-tetrahydro-11-chloro-8-oxo-4H-azocino[3,2,1-hi]indole-2-carboxylate was obtained by carrying out reaction according to the method described in Reference Example 6, (c), except for using ethyl 1-(4-carboxybutyl)-4-chloro-1H-indole-2-carboxylate (9.00 g, 27.8 mmol), diphosphorus pentaoxide (100 g) and 85% phosphoric acid (100 g).

M.p. 95–96° C. (after recrystallization from isopropanol).

$^1$Hnmr (CDCl$_3$) δ: 1.41–1.46(3H, m), 1.76–1.84(2H, m), 2.04–2.13(2H, m), 2.80–2.84(2H, m), 4.40(2H, dd, J=7.26, 14.19 Hz), 4.55(2H, brs), 7.18(1H, d, J=7.92 Hz), 7.25(1H, d, J=7.59 Hz), 7.45(1H, s).

(d) Synthesis of N-(aminoiminomethyl)-5,6,7,8-tetrahydro-11-chloro-8-oxo-4H-azocino[3,2,1-hi]indole-2-carboxamide methanesulfonate monohydrate 0.76 Gram of N-(aminoiminomethyl)-5,6,7,8-tetrahydro-11-chloro-8-oxo-4H-azocino[3,2,1-hi]indole-2-carboxamide methanesulfonate monohydrate was obtained by carrying out reaction according to the method described in Example 1, except for using ethyl 5,6,7,8-tetrahydro-11-chloro-8-oxo-4H-azocino[3,2,1-hi]indole-2-carboxylate (1.00 g, 3.27 mmol), sodium methoxide (3.53 g, 65.4 mmol), guanidine hydrochloride (6.25 g, 65.4 mmol) and N,N-dimethylformamide (80 ml). M.p. 144–146° C.

Elementary analysis (for C$_{15}$H$_{15}$Cl N$_4$O$_2$.CH$_4$SO$_3$.H$_2$O):

|  | C | H | N |
|---|---|---|---|
| Calcd. (%) | 44.40 | 4.89 | 12.94 |
| Found. (%) | 44.45 | 4.84 | 12.87 |

EXAMPLE 23

Synthesis of N-(aminoiminomethyl)-5,6,7,8-tetrahydro-11-chloro-4H-azocino[3,2,1-hi]indole-2-carboxamide methanesulfonate

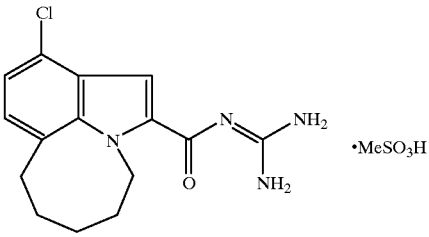

(a) Synthesis of ethyl 5,6,7,8-tetrahydro-11-chloro-8-hydroxy-4H-azocino[3,2,1-hi]indole-2-carboxylate 0.77 Gram of ethyl 5,6,7,8-tetrahydro-11-chloro-8-hydroxy-4H-azocino[3,2,1-hi]indole-2-carboxylate was obtained by carrying out reaction according to the method described in Reference Example 7, except for using ethyl 5,6,7,8-tetrahydro-11-chloro-8-oxo-4H-azocino[3,2,1-hi]indole-2-carboxylate (1.20 g, 3.92 mmol), sodium borohydride (0.15 g, 3.92 mmol), ethanol (15 ml) and tetrahydrofuran (10 ml).

$^1$Hnmr (CDCl$_3$) δ: 1.42(3H, t, J=7.26 Hz), 1.54–1.89(3H, m), 2.09–2.38(3H, m), 4.32–4.40(3H, m), 5.35–5.44(1H, m), 5.90(1H, brs), 7.09(1H, d, J=7.91 Hz), 7.34–7.38(2H, m).

(b) Synthesis of ethyl 5,6,7,8-tetrahydro-11-chloro-4H-azocino[3,2,1-hi]indole-2-carboxylate 0.84 Gram of ethyl 5,6,7,8-tetrahydro-11-chloro-4H-azocino[3,2,1-hi]indole-2-carboxylate was obtained by carrying out reaction according to the method described in Reference Example 5, except for using ethyl 5,6,7,8-tetrahydro-11-chloro-8-hydroxy-4H-azocino[3,2,1-hi]indole-2-carboxylate (1.23 g, 4.00 mmol), triethylsilane (1.02 g, 8.79 mmol) and trifluoro-acetic acid (25 ml).

$^1$Hnmr (CDCl$_3$) δ: 1.23–1.45(5H, m), 1.86–2.05(4H, m), 3.27(2H, brs), 4.33–4.41(2H, m), 5.01(2H, brs), 6.88(1H, d, J=7.59 Hz), 7.01(1H, d, J=7.59 Hz), 7.35(1H, s).

(c) Synthesis of N-(aminoiminomethyl)-5,6,7,8-tetrahydro-11-chloro-4H-azocino[3,2,1-hi]indole-2-carboxamide methanesulfonate 1.07 Grams of N-(aminoiminomethyl)-5,6,7,8-tetrahydro-11-chloro-4H-azocino[3,2,1-hi]indole-2- carboxamide methanesulfonate was obtained by carrying out reaction according to the method described in Example 1, except for using ethyl 5,6,7,8-tetrahydro-11-chloro-4H-azocino[3,2,1-hi]indole-2-carboxylate (0.84 g, 2.88 mmol), sodium methoxide (3.11 g, 57.6 mmol), guanidine hydrochloride (5.50 g, 57.6 mmol) and N,N-dimethylformamide (80 ml).

M.p. 263–264° C. (after recrystallization from a mixed solvent of water and isopropanol).

EXAMPLE 24

Synthesis of N-(aminoiminomethyl)-5,6-dihydro-11-chloro-4H-azocino[3,2,1-hi]indole-2-carboxamide methanesulfonate

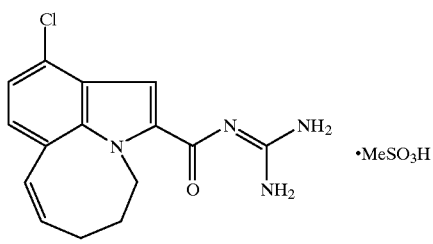

(a) Synthesis of ethyl 5,6-dihydro-11-chloro-4H-azocino[3,2,1-hi]indole-2-carboxylate A mixture of ethyl 5,6,7,8-tetrahydro-11-chloro-8-hydroxy-4H-azocino[3,2,1-hi]indole-2-carboxylate (0.70 g, 2.27 mmol), triethylamine (0.61 g, 6.00 mmol) and tetrahydrofuran (30 ml) was cooled to −20° C. with stirring, and methanesulfonyl chloride (0.31 g, 2.73 mmol) was added dropwise. After completion of the dropwise addition, the reaction temperature was raised to room temperature and the reaction mixture was allowed to stand overnight at room temperature. The reaction mixture was poured into an aqueous ammonium chloride solution and extracted twice with ethyl acetate, and the extract solution was washed with an aqueous sodium hydrogencarbonate solution and dried over anhydrous magnesium sulfate. The solvent was distilled off under reduced pressure and the resulting residue was purified by a silica gel column chromatography (eluent: ethyl acetate/n-hexane=2/98) to obtain 0.63 g of ethyl 5,6-dihydro-11-chloro-4H-azocino[3,2,1-hi]indole-2-carboxylate.

M.p. 89–90° C. (after recrystallization from isopropanol).
$^1$Hnmr (CDCl$_3$) δ: 1.3–1.6(4H, m), 2.0–2.4(3H, m), 4.38 (2H, dd, J=7.26, 14.19 Hz), 4.6–5.0(2H, m), 5.68–5.78(1H, m), 6.77(1H, d, J=11.21 Hz), 6.93(1H, d, J=7.91 Hz), 7.07(1H, d, J=7.91 Hz), 7.35(1H, s).

(b) Synthesis of N-(aminoiminomethyl)-5,6-dihydro-11-chloro-4H-azocino[3,2,1-hi]indole-2-carboxamide methanesulfonate 0.72 Gram of N-(aminoiminomethyl)-5,6-dihydro-11-chloro-4H-azocino[3,2,1-hi]indole-2-carboxamide methanesulfonate was obtained by carrying out reaction according to the method described in Example 1, except for using ethyl 5,6-dihydro-11-chloro-4H-azocino[3,2,1-hi]indole-2-carboxylate (0.60 g, 2.07 mmol), sodium methoxide (2.24 g, 41.4 mmol), guanidine hydrochloride (3.96 g, 41.4 mmol) and N,N-dimethylformamide (70 ml).

M.p. 231–232° C. (after recrystallization from a mixed solvent of water and isopropanol).

The following compounds of Examples 25 to 32 were synthesized by carrying out reaction according to the method described in Example 22.

EXAMPLE 25

N-(aminoiminomethyl)-5,6,7,8-tetrahydro-10-fluoro-11-methyl-8-oxo-4H-azocino[3,2,1-hi]indole-2-carboxamide methanesulfonate

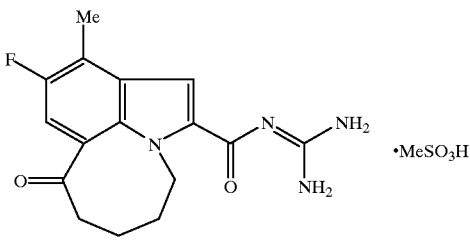

m.p. 277–278° C. (decomp.) (after recrystallization from a mixed solvent of water and isopropanol).

EXAMPLE 26

N-(aminoiminomethyl!-5,6,7,8-tetrahydro-11-methyl-8-oxo-4H-azocino[3,2,1-hi]indole-2-carboxamide methanesulfonate

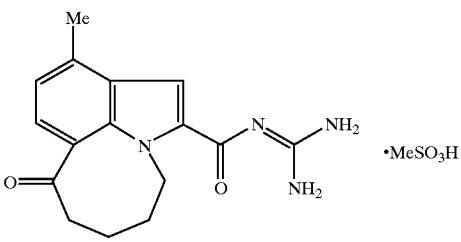

m.p. 283–284° C. (decomp.) (after recrystallization from a mixed solvent of water and isopropanol).

EXAMPLE 27

N-(aminoiminomethyl)-5,6,7,8-tetrahydro-10,11-difluoro-8-oxo-4H-azocino[3,2,1-hi]indole-2-carboxamide methanesulfonate

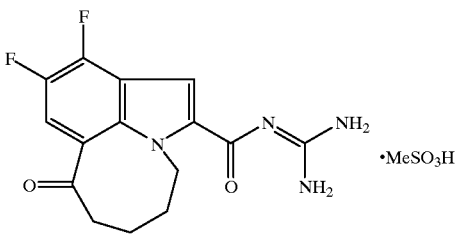

m.p. 278° C. (decomp.) (after recrystallization from a mixed solvent of water and isopropanol).

EXAMPLE 28

N-(aminoiminomethyl)-5,6,7,8-tetrahydro-11-fluoro-8-oxo-4H-azocino[3,2,1-hi]indole-2-carboxamide methanesulfonate

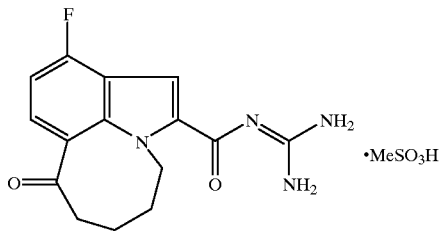

m.p. 244–246° C. (decomp.) (after recrystallization from water).

EXAMPLE 29

N-(aminoiminomethyl)-5,6,7,8-tetrahydro-10-chloro-11-methyl-8-oxo-4H-azocino[3,2,1-hi]indole-2-carboxamide methanesulfonate

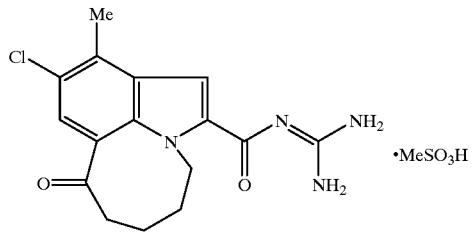

m.p. 301° C. (decomp.) (after recrystallization from a mixed solvent of water and isopropanol).

EXAMPLE 30

N-(aminoiminomethy)-5,6,7,8-tetrahydro-9,11-dimethyl-8-oxo-4H-azocino[3,2,1-hi]indole-2-carboxamide methanesulfonate

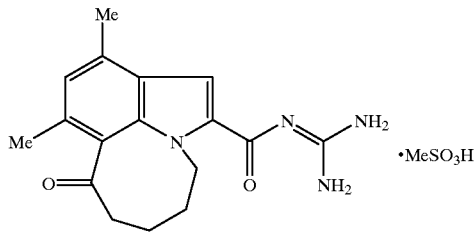

m.p. 234–236° C. (decomp.) (after recrystallization from a mixed solvent of water and isopropanol).

EXAMPLE 31

N-(aminoiminomethyl)-5,6,7,8-tetrahydro-10,11-dichloro-8-oxo-4H-azocino[3,2,1-hi]indole-2-carboxamide methanesulfonate

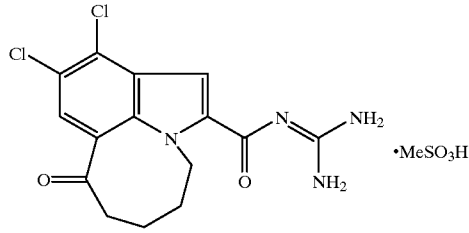

m.p. 297° C. (decomp.) (after recrystallization from a mixed solvent of water and isopropanol).

Example 32

N-(aminoiminomethyl)-5,6,7,8-tetrahydro-11-chloro-10-methoxy-8-oxo-4H-azocino[3,2,1-hi]indole-2-carboxamide methanesulfonate

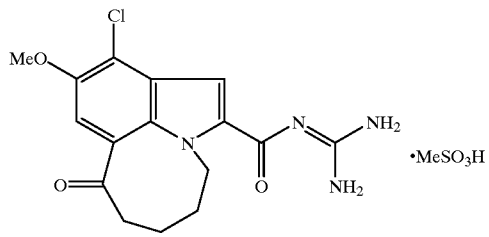

m.p. 275–276° C. (decomp.) (after recrystallization from a mixed solvent of water and isopropanol).

EXAMPLE 33

Synthesis of N-(aminoiminomethyl)-5,6,7,8-tetrahydro-11-chloro-8-hydroxy-4H-azocino[3,2,1-hi]indole-2-carboxamide methanesulfonate

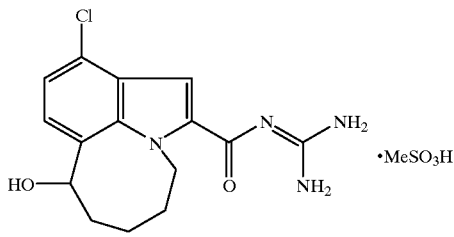

N-(aminoiminomethyl)-5,6,7,8-tetrahydro-11-chloro-8-hydroxy-4H-azocino[3,2,1-hi]indole-2-carboxamide methanesulfonate was obtained by carrying out reaction according to the method described in Example 1, except for using the ethyl 5,6,7,8-tetrahydro-11-chloro-8-hydroxy-4H-azocino[3,2,1-hi]indole-2-carboxylate obtained in Example 23, (a).

M.p. 238–239° C. (after recrystallization from a mixed solvent of water and isopropanol).

EXAMPLE 34

Synthesis of N-(aminoiminomethyl)-4,5,7,8-tetrahydro-11-methyl-8-oxo-pyrrolo[3,2,1-kl]benzo[e][1,4]oxazocine-2-carboxamide methanesulfonate

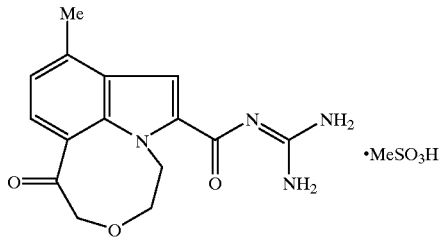

a) Synthesis of ethyl (2-benzyloxyethoxy)acetate

A mixture of ethylene glycol monobenzyl ether (36 ml, 252 mmol), 60% sodium hydride (11.0 g, 275 mmol) and N,N-dimethylformamide (300 ml) was stirred at room temperature for 1.5 hours. To the resulting suspension was added dropwise a solution of ethyl bromoacetate (34 ml, 302 mmol) in N,N-dimethylformamide (50 ml), followed by stirring at room temperature for another 3 hours. The reaction mixture was poured into a 10% aqueous sodium chloride solution and extracted with ethylacetate, and the extract solution.was washed with a 5% aqueous sodium chloride solution and dried over anhydrous magnesium sulfate. The solvent was distilled off under reduced pressure and the resulting residue was purified by a silica gel column chromatography (eluent: ethyl acetate:n-hexane=9:95) to obtain 18.5 g of ethyl (2-benzyloxyethoxy)acetate as a colorless oil.

$^1$Hnmr (CDCl$_3$) δ: 1.20(3H, t, J=6.9 Hz), 1.96(2H, s), 3.62(2H, t, J=4.0 Hz), 3.69(2H, t, J=4.0 Hz), 4.13(2H, q, J=6.9 Hz), 4.50(2H, s), 7.19–7.28(5H, m).

b) Synthesis of ethyl (2-hydroxyethoxy)acetate

A mixture of ethyl (2-benzyloxyethoxy)acetate (0.50 g, 1.88 mmol), 10% palladium-carbon (0.05 g) and methanol (10 ml) was stirred under a hydrogen atmosphere at room temperature for 5 hours. The catalyst was filtered off and the filtrate was concentrated under reduced pressure to obtain 0.29 g of ethyl (2-hydroxyethoxy)acetate as a colorless oil.

$^1$Hnmr (CDCl$_3$) δ: 1.30(3H, t, J=7.3 Hz), 2.79(1H, br-s), 3.67–3.90 (4H, m), 4.12–4.28(4H, m).

c) Synthesis of ethyl [2-(toluene-4-sulfonyloxy)ethoxy]acetate

A mixture of ethyl (2-hydroxyethoxy)acetate (0.50 g, 3.37 mmol), triethylamine (1.4 ml) and methylene chloride (8 ml) was stirred under ice-cooling. Then, p-toluenesulfonyl chloride (0.96 g, 5.06 mmol) was added in small portions and the resulting mixture was stirred under ice-cooling for another 3 hours. The reaction mixture was poured into water and extracted with ethyl acetate, and the extract solution was washed with a saturated aqueous sodium chloride solution and dried over anhydrous magnesium sulfate. The solvent was distilled off under reduced pressure and the resulting residue was purified by a silica gel column chromatography (eluent: ethyl acetate:n-hexane=1:5) to obtain 0.56 g of ethyl [2-(toluene-4-sulfonyloxy)ethoxy]acetate as a colorless oil.

$^1$Hnmr (CDCl$_3$) δ:
1.27(3H, t, J=7.3 Hz), 2.45(3H, s), 3.78(2H, t, J=4.6 Hz), 4.06 (2H, s), 4.16–4.24(5H, m), 7.35(2H, t, J=8.6 Hz), 7.81(2H, d, J=8.6 Hz).

d) Synthesis of ethyl 1-[(2-ethoxycarbonylmethoxy)ethyl]-4-methyl-1H-indole-2-carboxylate A solution of ethyl [2-(toluene-4-sulfonyloxy)ethoxy] acetate (3.90 g, 12.9 mmol) in N,N-dimethylformamide (10 ml) was added dropwise to a mixture of ethyl 4-methyl-1H-indole-2-carboxylate (2.50 g, 12.3 mmol), 60% sodium hydride (0.50 g, 12.5 mmol) and N,N-dimethylformamide (45 ml) at room temperature, and the resulting mixture was stirred at room temperature for 7 hours. The reaction mixture was poured into a 10% aqueous sodium chloride solution and extracted with ethyl acetate, and the extract solution was washed with a 5% aqueous sodium chloride solution and dried over anhydrous magnesium sulfate. The solvent was distilled off under reduced pressure and the resulting residue was purified by a silica gel column chromatography (eluent: ethyl acetate:n-hexane=2:98) to obtain 1.86 g of ethyl 1-[(2-ethoxycarbonylmethoxy)ethyl]-4-methyl-1H-indole-2-carboxylate as a colorless oil.

$^1$Hnmr (CDCl$_3$) δ: 1.23(3H, t, J=7.3 Hz), 1.42(3H, t, J=7.3 Hz), 2.55(3H, s), 3.91(2H, t, J=5.9 Hz), 3.98 (2H, s), 4.16(2H, q, J=7.3 Hz), 4.37(2H, q, J=7.3 Hz), 4.78(2H, t, J=5.9 Hz), 6.94(1H, d, J=6.9 Hz), 7.24(1H, dd, J=6.9, 6.9 Hz), 7.35(1H, s), 7.36(1H, d, J=6.9 Hz).

e) Synthesis of ethyl 4-methyl-1-[(2-carboxymethoxy)ethyl]-1H-indole-2-carboxylate Ethyl 1-[(2-ethoxycarbonylmethoxy)ethyl]-4-methyl-1H-indole-2-carboxylate (1.49 g, 4.47 mmol) was dissolved in acetic acid (15 ml), followed by adding thereto 30% sulfuric acid (7.5 ml), and the resulting mixture was stirred at 70° C. for 4 hours. The reaction mixture was poured into ice water and extracted with diethyl ether, and the extract solution was washed with a saturated aqueous sodium chloride solution and dried over anhydrous magnesium sulfate. The solvent was distilled off under reduced pressure to obtain 1.37 g of ethyl 4-methyl-1-[(2-carboxymethoxy)ethyl]-1H-indole-2-carboxylate.

$^1$Hnmr (CDCl$_3$) δ: 1.42(3H, t, J=7.3 Hz), 2.56(3H, s), 3.95(1H, t, J=5.6 Hz), 4.00 (2H, s), 4.38(2H, q, J=7.3 Hz), 4.82(2H, t, J=5.6 Hz), 6.94–6.97(1H, m), 7.25(1H, d, J=8.6 Hz), 7.28(1H, dd, J=8.6, 8.6 Hz), 7.38(1H, s).

f) Synthesis of ethyl 4,5,7,8-tetrahydro-11-methyl-8-oxo-pyrrolo[3,2,1-kl]benzo[e][1,4]oxazocine-2-carboxylate Ethyl 4-methyl-1-[(2-carboxymethoxy)ethyl]-1H-indole-2-carboxylate (0.10 g, 0.33 mmol) was added to 1 ml of PPE (polyphosphate ester; prepared from diphosphorus pentaoxide and diethyl ether), and the resulting mixture was stirred at 60° C. for 30 minutes. Ice water was poured into the reaction mixture, followed by extraction with diethyl ether. The extract solution was washed with a saturated aqueous sodium chloride solution and dried over anhydrous magnesium sulfate. The solvent was distilled off under reduced pressure and the resulting residue was purified by a silica gel column chromatography (eluent: ethyl acetate:n-hexane= 1:5) to obtain 0.007 g of ethyl 4,5,7,8-tetrahydro-11-methyl-8-oxo-pyrrolo[3,2,1-kl]benzo[e][1,4]oxazocine-2-carboxylate.

$^1$Hnmr (CDCl$_3$) δ: 1.3(3H, t, J=6.9 Hz), 2.60(3H, s), 4.14(2H, br-s), 4.35–4.43(4H, m), 4.72(2H, br-s), 7.02(1H, dd, J=0.7, 7.3 Hz), 7.43(1H, s), 7.49(1H, d, J=7.3 Hz).

g) Synthesis of N-(aminoiminomethyl)-4,5,7,8-tetrahydro-11-methyl-8-oxo-pyrrolo[3,2,1-kl]benzo[e][1,4]oxazocine-2-carboxamide methanesulfonate 0.016 Gram of N-(aminoiminomethyl)-4,5,7,8-tetrahydro-11-methyl-8-oxo-pyrrolo[3,2,1-kl]benzo[e][1,4]

oxazocine-2-carboxamide methanesulfonate was obtained by carrying out reaction according to the method described in Example 1, except for using ethyl 4,5,7,8-tetrahydro-11-methyl-8-oxo-pyrrolo[3,2,1-kl]benzo[e][1,4]oxazocine-2-carboxylate (0.036 g, 0.125 mmol), sodium methoxide (0.068 g, 1.25 mmol), guanidine hydrochloride (0.119 g, 1.25 mmol) and N,N-dimethylformamide (5 ml).

M.p. 308–310° C. (decomp.) (after recrystallization from a mixed solvent of water and isopropanol).

EXAMPLE 35

Synthesis of N-(aminoiminomethyl)-5,6,7,8-tetrahydro-11-chloro-8-methoxy-4H-azocino[3,2,1-hi]indole-2-carboxamide methanesulfonate

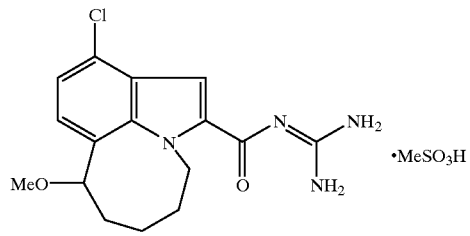

(a) Synthesis of ethyl 5,6,7,8-tetrahydro-11-chloro-8-methoxy-4H-azocino[3,2,1-hi]indole-2-carboxylate The ethyl 5,6,7,8-tetrahydro-11-chloro-8-hydroxy-4H-azocino[3,2,1-hi]indole-2-carboxylate (1.90 g, 6.17 mmol) obtained in Example 23, (a) was added to a mixture of methanol (19 ml) and concentrated sulfuric acid (1.89 g) which had been cooled to 0° C. The reaction mixture was heated to 40° C. and stirred for 1 hour. The reaction mixture was poured into ice water and extracted twice with ethyl acetate, and the extract solution was washed twice with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=1/99) to obtain 1.96 g of ethyl 5,6,7,8-tetrahydro-11-chloro-8-methoxy-4H-azocino[3,2,1-hi]indole-2-carboxylate as a colorless oil.

$^1$Hnmr (CDCl$_3$) δ: 1.1–1.7(2H, m), 1.42(3H, t, J=7.26 Hz), 1.7–2.4(4H, m), 3.38(3H, br-s), 4.37(2H, dd, J=7.26, 14.19 Hz), 4.65 (0.3H, br-s), 5.35–5.50(1H, m), 7.10(1H, d, J=7.59 Hz), 7.20(1H, br-s), 7.39(1H, s).

(b) Synthesis of N-(aminoiminomethyl)-5,6,7,8-tetrahydro-11-chloro-8-methoxy-4H-azocino[3,2,1-hi]indole-2-carboxamide methanesulfonate 1.99 Grams of N-(aminoiminomethyl)-5,6,7,8-tetrahydro-11-chloro-8-methoxy-4H-azocino[3,2,1-hi]indole-2-carboxamide methanesulfonate was obtained by carrying out reaction according to the method described in Example 1, except for using ethyl 5,6,7,8-tetrahydro-11-chloro-8-methoxy-4H-azocino[3,2,1-hi]indole-2-carboxylate (1.96 g, 6.10 mmol), sodium methoxide (3.30 g, 61.0 mmol), guanidine hydrochloride (5.83 g, 61.0 mmol) and N,N-dimethylformamide (39 ml).

M.p. 133–134° C. (after recrystallization from a mixed solvent of water and isopropanol).

The following compound of Example 36 was synthesized by carrying out reaction according to the method described in Example 35.

EXAMPLE 36

N-(aminoiminomethyl)-5,6,7,8-tetrahydro-11-chloro-8-ethoxy-4H-azocino[3,2,1-hi]indole-2-carboxamide methanesulfonate

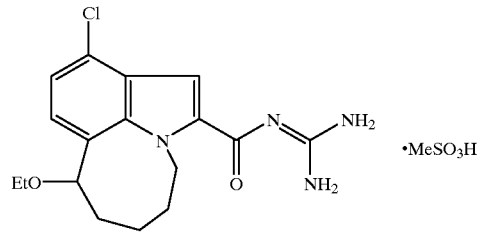

m.p. 190–191° C. (this compound was crystallized from tetrahydrofuran).

EXAMPLE 37

Synthesis of N-(aminoiminomethyl)-5,6,7,8-tetrahydro-11-chloro-10-hydroxy-8-oxo-4H-azocino[3,2,1-hi]indole-2-carboxamide methanesulfonate

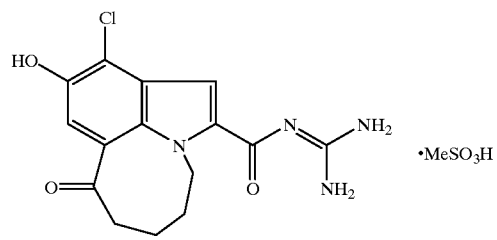

a) Synthesis of ethyl 1-(4-ethoxycarbonylbutyl)-4-chloro-5-methoxy-1H-indole-2-carboxylate 13.98 Grams of ethyl 1-(4-ethoxycarbonylbutyl)-4-chloro-5-methoxy-1H-indole-2-carboxylate was obtained by carrying out reaction according to the method described in Reference Example 6, (a), except for using ethyl 4-chloro-5-methoxy-1H-indole-2-carboxylate (10.13 g, 39.9 mmol), 60% sodium hydride (1.60 g, 39.9 mmol), ethyl 5-bromovalerate (12.52 g, 59.9 mmol) and N,N-dimethylformamide (200 ml).

M.p. 61–62° C. (after recrystallization from isopropanol).

b) Synthesis of ethyl 1-(4-carboxybutyl)-4-chloro-5-methoxy-1H-indole-2-carboxylate 12.7 Grams of ethyl 1-(4-carboxybutyl)-4-chloro-5-methoxy-1H-indole-2-carboxylate was obtained by carrying out reaction according to the method described in Reference Example 6, (b), except for using ethyl 1-(4-ethoxycarbonylbutyl)-4-chloro-5-methoxy-1H-indole-2-carboxylate (13.50 g, 35.4 mmol), 30% sulfuric acid (150 ml) and acetic acid (300 ml).

M.p. 124–125° C. (after recrystallization from acetonitrile).

c) Synthesis of ethyl 5,6,7,8-tetrahydro-11-chloro-10-methoxy-8-oxo-4H-azocino[3,2,1-hi]indole-2-carboxylate 9.68 Grams of ethyl 5,6,7,8-tetrahydro-11-chloro-10-methoxy-8-oxo-4H-azocino[3,2,1-hi]indole-2-carboxylate was obtained by carrying out reaction according to the method described in Reference Example 6, (c), except for using ethyl 1-(4-carboxybutyl)-4-chloro-5-methoxy-1H-indole-2-carboxylate (12.70 g, 35.7 mol), diphosphorus pentaoxide (200 g) and 85% phosphoric acid (160 g).

M.p. 101–102° C. (after recrystallization from isopropanol).

d) Synthesis of ethyl 5,6,7,8-tetrahydro-11-chloro-10-hydroxy-8-oxo-4H-azocino[3,2,1-hi]indole-2-carboxylate A solution of ethyl 5,6,7,8-tetrahydro-11-chloro-10-methoxy-8-oxo-4H-azocino[3,2,1-hi]indole-2-carboxylate (4.00 g, 11.8 mmol) in dichloromethane (80 ml) was cooled to −78° C., and boron tribromide (3.26 g, 13.0 mmol) was added dropwise. The reaction temperature was raised to −20° C. and the reaction mixture was stirred at −20° C. for 8 hours. The reaction mixture was poured into ice water and extracted three times with ethylacetate, and the extract solution was washed with a saturated aqueous ammonium chloride solution and dried over anhydrous magnesium sulfate. The solvent was distilled off under reduced pressure and the resulting residue was purified by a silica gel column chromatography (eluent: ethyl acetate/n-hexane=1/9) to obtain 0.99 g of ethyl 5,6,7,8-tetrahydro-11-chloro-10-hydroxy-8-oxo-4H-azocino[3,2,1-hi]indole-2-carboxylate.

$^1$Hnmr (CDCl$_3$) δ: 1.40–1.45(3H, m), 1.76–1.85(2H, m), 2.05–2.08(2H, m), 2.79–2.84(2H, m), 4.39(2H, dd, J=7.26, 14.19 Hz), 4.51(2H, br-s), 5.58(1H, br-s), 7.07(1H, s), 7.30(1H, s).

e) Synthesis of ethyl 5,6,7,8-tetrahydro-11-chloro-10-methoxymethyloxy-8-oxo-4H-azocino[3,2,1-hi]indole-2-carboxylate A mixture of ethyl 5,6,7,8-tetrahydro-11-chloro-10-hydroxy-8-oxo-4H-azocino[3,2,1-hi]indole-2-carboxylate (0.95 g, 2.93 mmol), chloromethyl methyl ether (0.35 g, 4.40 mmol), potassium carbonate (1.22 g, 8.80 mmol) and N,N-dimethylformamide (25 ml) was stirred at room temperature for 1 hour. The insoluble material was filtered off and the filtrate was poured into ice water and extracted twice with ethyl acetate. The extract solution was washed with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=2/98) to obtain 0.51 g of ethyl 5,6,7,8-tetrahydro-11-chloro-10-methoxymethyloxy-8-oxo-4H-azocino[3,2,1-hi]indole-2-carboxylate.

$^1$Hnmr (CDCl$_3$) δ: 1.40–1.45(3H, m), 1.7–1.8(2H, m), 1.9–2.1(2H, m), 2.80–2.85(2H, m), 3.57(3H, s), 4.35–4.43 (2H, m), 5.23(2H, s), 7.24(1H, s), 7.39(1H, s).

f) Synthesis of N-(aminoiminomethyl)-5,6,7,8-tetrahydro-11-chloro-10-hydroxy-8-oxo-4H-azocino[3,2,1-hi]indole-2-carboxamide methanesulfonate Crude N-(aminoiminomethyl)-5,6,7,8-tetrahydro-11-chloro-10-methoxymethyloxy-8-oxo-4H-azocino[3,2,1-hi]indole-2-carboxamide was obtained by carrying out reaction according to the method described in Example 1, except for using ethyl 5,6,7,8-tetrahydro-11-chloro-10-methoxymethyloxy-8-oxo-4H-azocino[3,2,1-hi]indole-2-carboxylate (0.50 g, 1.36 mmol), guanidine hydrochloride (2.60 g, 27.2 mmol), sodium methoxide (1.47 g, 27.2 mmol) and N,N-dimethylformamide (50 ml). Subsequently, the crude product was added to a mixture of isopropanol (70 ml), water (20 ml) and methanesulfonic acid (0.50 g), and the resulting mixture was stirred at 65–70° C. for 6 hours. The reaction mixture was neutralized with 28% aqueous ammonia and extracted three times with ethyl acetate, and the extract solution was washed with a saturated aqueous sodium chloride solution and dried over anhydrous magnesium sulfate. The solvent was distilled off under reduced pressure and the resulting residue was dissolved in tetrahydrofuran (70 ml), after which methanesulfonic acid (0.26 g) was added and the solid precipitated was collected by filtration. The solid collected was recrystallized from a mixture of isopropanol (1 ml) and water (20 ml) to obtain 0.25 g of N-(aminoiminomethyl)-5,6,7,8-tetrahydro-11-chloro-10-hydroxy-8-oxo-4H-azocino[3,2,1-hi]indole-2-carboxamide methanesulfonate.

M.p. 263–264° C. (decomp.).

EXAMPLE 38

Synthesis of N-(aminoiminomethyl)-5,6,7,8-tetrahydro-6,11-dimethyl-8-oxo-4H-pyrrolo[3,2,1-kl]benzo[e][1,4]diazocine-2-carboxamide dimethanesulfonate

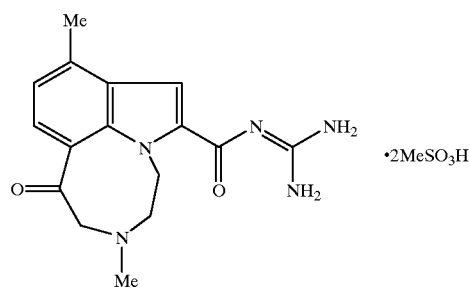

a) Synthesis of 2-tert-butoxycarbonylaminoethanol

Di-tert-butyl dicarbonate (20.0 g, 91.6 mmol) was added to a solution of 2-aminoethanol (6.72 g, 110 mmol) in dichloromethane (100 ml), and the resulting mixture was stirred at room temperature for 1 hour and then allowed to stand at room temperature for 12 hours. The reaction mixture was diluted with diethyl ether (200 ml) and washed with a saturated aqueous sodium hydrogencarbonate solution and then a saturated aqueous sodium chloride solution. The organic layer was dried over anhydrous magnesium sulfate and the solvent was distilled off under reduced pressure to obtain 11.0 g of 2-tert-butoxycarbonylaminoethanol.

$^1$Hnmr (CDCl$_3$) δ: 1.45(9H, s), 2.99(1H, br-s), 3.28(2H, dt, J=5.3 Hz, 5.3 Hz), 3.68(2H, dt, J=4.6 Hz, 5.0 Hz), 5.10(1H, br-s).

b) Synthesis of 2-tert-butoxycarbonylaminoethyl 4-toluenesulfonate

A mixture of 2-tert-butoxycarbonylaminoethanol (32.7 g, 203 mmol), triethylamine (34 ml), p-toluenesulfonyl chloride (38.7 g, 203 mmol), 4-dimethylaminopyridine (0.10 g) and dichloromethane (500 ml) was stirred at 0° C. for 4 hours. The reaction mixture was washed successively with water, 1N hydrochloric acid, a saturated aqueous sodium hydrogencarbonate solution and a saturated aqueous sodium chloride solution. The organic layer was dried over anhydrous magnesium sulfate and the solvent was distilled off under reduced pressure. The resulting residue was purified by a silica gel column chromatography (eluent: ethyl acetate/n-hexane=1/5) to obtain 48.2 g of 2-tert-butoxycarbonylaminoethyl 4-toluenesulfonate.

$^1$Hnmr (CDCl$_3$) δ: 1.41(9H, s), 2.44(3H, s), 3.38(2H, dt, J=5.6 Hz, 5.6 Hz), 4.07(2H, t, J=5.3 Hz), 4.87(1H, br-s), 7.35(2H, dd, J=0.7 Hz, 8.6 Hz), 7.78(2H, ddd, J=2.0 Hz, 2.0 Hz, 8.3 Hz).

c) Synthesis of ethyl 1-(2-tert-butoxycarbonylaminoethyl)-4-methyl-1H-indole-2-carboxylate A mixture of ethyl 4-methyl-1H-indole-2-carboxylate (42.9 g, 211 mmol), 60% sodium hydride (9.29 g, 232 mmol) and N,N-dimethylformamide (300 ml) was stirred at room temperature for 1 hour. A solution of 2-tert-butoxycarbonylaminoethyl 4-toluenesulfonate (86.6 g, 275 mmol) in N,N-dimethylformamide (200 ml) was added dropwise and the resulting mixture was stirred at room temperature for 9 hours. The reaction mixture was poured into ice water and extracted twice with ethyl acetate, and the extract solution was washed with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=3/97) to obtain 24.4 g of ethyl 1-(2-tert-butoxycarbonylaminoethyl)-4-methyl-1H-indole-2-carboxylate.

M.p. 93–94° C. (after recrystallization from isopropanol).

d) Synthesis of ethyl 1-[2-(4-methylphenylsulfonyl)aminoethyl]-4-methyl-1H-indole-2-carboxylate A mixture of ethyl 1-(2-tert-butoxycarbonylaminoethyl)-4-methyl-1H-indole-2-carboxylate (27.2 g, 78.5 mmol), trifluoroacetic acid (75 ml) and dichloromethane (250 ml) was stirred at 0° C. for 3 hours, slow poured into cold aqueous ammonia, and then extracted twice with ethyl acetate. The extract solution was washed with a 5% aqueous sodium chloride solution and dried over anhydrous magnesium sulfate. The solvent was distilled off under reduced pressure, after which the residue was dissolved in pyridine (150 ml) and the resulting solution was cooled to 5° C. p-Toluenesulfonyl chloride (22.4 g, 118 mmol) was added to the cooled solution in small portions and the resulting mixture was stirred at 5° C. for 3 hours and then allowed to stand overnight at room temperature. The reaction mixture was poured into ice water and extracted twice with ethyl acetate, and the extract solution was washed successively with 1N hydrochloric acid, a saturated aqueous sodium hydrogencarbonate solution and a 5% aqueous sodium chloride solution. The organic layer was dried over anhydrous magnesium sulfate and the solvent was distilled off under reduced pressure. The resulting residue was purified by a silica gel column chromatography (eluent: ethyl acetate/n-hexane=1/9) to obtain 27.6 g of ethyl 1-[2-(4-methylphenylsulfonyl)aminoethyl]-4-methyl-1H-indole-2-carboxylate.

M.p. 92–93° C. (after recrystallization from isopropanol).

e) Synthesis of ethyl 1-[2-[N-ethoxycarbonylmethyl-N-(4-methylphenylsulfonyl)]aminoethyl]-4-methyl-1H-indole-2-carboxylate A mixture of ethyl 1-[2-(4-methylphenylsulfonyl)aminoethyl]-4-methyl-1H-indole-2-carboxylate (27.6 g, 69.0 mmol), 60% sodium hydride (2.76 g, 69.0 mmol) and N,N-dimethylformamide (500 ml) was stirred at room temperature for 2 hours, followed by adding thereto ethyl bromoacetate (13.8 g, 82.8 mmol), and the resulting mixture was stirred at room temperature for another 2 hours. The reaction mixture was poured into ice water and extracted twice with ethyl acetate, and the extract solution was washed with a 5% aqueous sodium chloride solution and dried over anhydrous sodium sulfate. The solvent was distilled off under reduced pressure and the resulting residue was purified by a silica gel column chromatography (eluent: ethyl acetate/n-hexane=5/95) to obtain 27.5 g of ethyl 1-[2-[N-ethoxycarbonylmethyl-N-(4-methylphenylsulfonyl)]-aminoethyl]-4-methyl-1H-indole-2-carboxylate.

M.p. 102–103° C. (after recrystallization from isopropanol).

f) Synthesis of ethyl 1-[2-[N-carboxymethyl-N-(4-methylphenylsulfonyl)]aminoethyl]-4-methyl-1H-indole-2-carboxylate 0.55 Gram of ethyl 1-[2-[N-carboxymethyl-N-(4-methylphenylsulfonyl)]aminoethyl]-4-methyl-1H-indole-2-carboxylate was obtained by carrying out reaction according to the method described in Reference Example 6, (b), except for using ethyl 1-[2-[N-ethoxycarbonyl-methyl-N-(4-methylphenylsulfonyl)]aminoethyl]-4-methyl-1H-indole-2-carboxylate (0.65 g, 1.34 mmol), 30% sulfuric acid (7 ml) and acetic acid (15 ml).

M.p. 121–122° C. (after recrystallization from acetonitrile).

g) Synthesis of ethyl 5,6,7,8-tetrahydro-11-methyl-6-(4-methylphenylsulfonyl)-8-oxo-4H-pyrrolo[3,2,1-kl]benzo[e][1,4]diazocine-2-carboxylate 1.55 Grams of ethyl 5,6,7,8-tetrahydro-11-methyl-6-(4-methylphenylsulfonyl)-8-oxo-4H-pyrrolo[3,2,1-kl]benzo[e][1,4]diazocine-2-carboxylate was obtained by carrying out reaction according to the method described in Reference Example 6, (c), except for using ethyl 1-[2-[N-carboxymethyl-N-(4-methylphenylsulfonyl)]aminoethyl]-4-methyl-1H-indole-2-carboxylate (2.60 g, 5.67 mmol), diphosphorus pentaoxide (150 g) and 85% phosphoric acid (125 g).

M.p. 177–178° C. (after recrystallization from isopropanol).

h) Synthesis of ethyl 5,6,7,8-tetrahydro-11-methyl-8-oxo-4H-pyrrolo[3,2,1-kl]benzo[e][1,4]diazocine-2-carboxylate A mixture of ethyl 5,6,7,8-tetrahydro-11-methyl-6-(4-methylphenylsulfonyl)-8-oxo-4H-pyrrolo[3,2,1-kl]benzo[e][1,4]diazocine-2-carboxylate (0.50 g, 1.14 mmol), trifluoroacetic acid (18 ml), thioanisole (2 ml) and methanesulfonic acid (0.60 g) was stirred at room temperature for 3 hours. The reaction mixture was poured into cold aqueous ammonia and extracted twice with ethyl acetate, and the extract solution was washed with a 5% aqueous sodium chloride solution and dried over anhydrous magnesium sulfate. The solvent was distilled off under reduced pressure and the resulting residue was separated by a silica gel column chromatography (eluent: ethyl acetate/n-hexane=3/7) to obtain ethyl 5,6,7,8-tetrahydro-11-methyl-8-oxo-4H-pyrrolo[3,2,1-kl]benzo[e][1,4]diazocine-2-carboxylate.

M.p. 139–140° C. (after recrystallization from isopropanol).

i) Synthesis of ethyl 5,6,7,8-tetrahydro-6,11-dimethyl-8-oxo-4H-pyrrolo[3,2,1-kl]benzo[e][1,4]diazocine-2-carboxylate A mixture of ethyl 5,6,7,8-tetrahydro-11-methyl-8-oxo-4H-pyrrolo[3,2,1-kl]benzo[e][1,4]diazocine-2-carboxylate (1.37 g, 4.78 mmol), methyl iodide (1.02 g, 7.17 mmol), potassium carbonate (1.98 g, 14.4 mmol) and N,N-dimethylformamide (40 ml) was stirred at room temperature for 2 hours. The reaction mixture was poured into cold water and extracted with ethyl acetate, and the extract solution was washed with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=1/9) to obtain 1.22 g of ethyl 5,6,7,8-tetrahydro-6,11-dimethyl-8-oxo-4H-pyrrolo[3,2,1-kl]benzo[e][1,4]diazocine-2-carboxylate.

M.p. 107–108° C. (after recrystallization from isopropanol).

j) Synthesis of N-(aminoiminomethyl)-5,6,7,8-tetrahydro-6,11-dimethyl-8-oxo-4H-pyrrolo[3,2,1-kl]benzo[e][1,4]diazocine-2-carboxamide dimethanesulfonate 1.36 Grams of N-(aminoiminomethyl)-5,6,7,8-tetrahydro-6,11-dimethyl-8-oxo-4H-pyrrolo[3,2,1-kl]benzo[e][1,4]diazocine-2-carboxamide dimethanesulfonate was obtained by carrying out reaction according to the method described in Example 1, except for using ethyl 5,6,7,8-tetrahydro-6,11-dimethyl-8-oxo-4H-pyrrolo[3,2,1-kl]benzo[e][1,4]diazocine-2-carboxylate (1.10 g, 3.66 mmol), guanidine hydrochloride (6.99 g, 73.3 mmol), sodium methoxide (3.96 g, 73.3 mmol) and N,N-dimethylformamide (80 ml).

M.p. 281–282° C. (decomp.) (after recrystallization from a mixed solvent of water and isopropanol).

EXAMPLE 39

Synthesis of N-(aminoiminomethyl)-5,6,7,8-tetrahydro-11-methyl-8-oxo-4H-pyrrolo[3,2,1-k]benzo-[e][1,4]diazocine-2-carboxamide dimethanesufonate

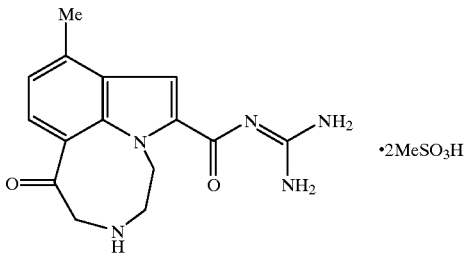

N-(aminoiminomethyl)-5,6,7,8-tetrahydro-11-methyl-6-(4-methylphenylsulfonyl)-8-oxo-4H-pyrrolo[3,2,1-kl]benzo[e][1,4]diazocine-2-carboxamide was obtained by carrying out reaction according to the method described in Example 1, except for using the ethyl 5,6,7,8-tetrahydro-11-methyl-6-(4-methylphenylsulfonyl)-8-oxo-4H-pyrrolo[3,2,1-kl]benzo[e][1,4]diazocine-2-carboxylate (0.80 g, 1.82 mmol), guanidine hydrochloride (3.47 g, 36.3 mmol), sodium methoxide (1.96 g, 36.3 mmol) and N,N-dimethylformamide (50 ml). Subsequently, the obtained compound was added to a mixture of trifluoroacetic acid (20 ml), thioanisole (3 ml) and methanesulfonic acid (0.7 g), and the resulting mixture was stirred at room temperature for 8 hours and then allowed to stand overnight. The reaction mixture was poured into cold aqueous ammonia and extracted twice with ethyl acetate, and the extract solution was washed with a saturated aqueous sodium chloride solution and dried over anhydrous magnesium sulfate. The solvent was distilled off under reduced pressure and the resulting residue was purified by a silica gel column chromatography (eluent:chloroform/methanol=95/5) to obtain 0.49 g of N-(aminoiminomethyl)-5,6,7,8-tetrahydro-11-methyl-8-oxo-4H-pyrrolo[3,2,1-kl]benzo[e][1,4]diazocine-2-carboxamide. Then, this free base was treated with a mixture of methanesulfonic acid (0.63 g), isopropanol (50 ml) and water (15 ml) to obtain 0.54 g of N-(aminoiminomethyl)-5,6,7,8-tetrahydro-11-methyl-8-oxo-4H-pyrrolo[3,2,1-kl]benzo[e][1,4]diazocine-2-carboxamide dimethanesulfonate.

M.p. 298–300° C. (decomp.).

EXAMPLE 40

Synthesis of N-(aminoiminomethyl)-5,6,7,8-tetrahydro-11-chloro-9-mthoxy-8-oxo-4H-azocino[3,2,1-hi]indole-2-carboxamide mthanesulfonate

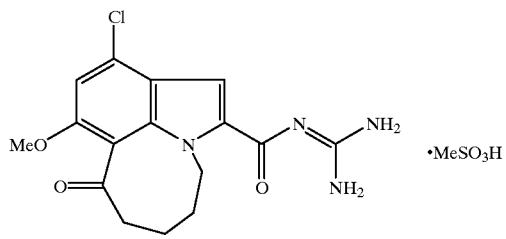

a) Synthesis of ethyl 6-benzyloxy-4-chloro-1-(4-ethoxycarbonylbutyl)-1H-indolecarboxylate 19.9 Grams of ethyl 6-benzyloxy-4-chloro-1-(4-ethoxycarbonylbutyl)-1H-indolecarboxylate was obtained as an oil by carrying out reaction according to the method described in Reference Example 6, (a), except for using ethyl 6-benzyloxy-4-chloro-1H-indolecarboxylate (15.0 g, 45.5 mmol), ethyl 5-bromovalerate (9.98 g, 47.8 mmol), 60% sodium hydride (1.82 g, 45.5 mmol) and N,N-dimethylformamide (105 ml).

$^1$Hnmr (CDCl$_3$) δ: 1.20–1.26(3H, m), 1.40(3H, t, J=7.26Hz), 1.60–1.69(2H, m), 1.72–1.83(2H, m), 2.28–2.33 (2H, m), 4.10(2H, dd, J=7.26, 14.19 Hz), 4.35(2H, dd, J=7.26, 14.18 Hz), 4.45–4.50(2H, m), 5.13(2H, s), 6.75(1H, t, J=0.99 Hz), 6.94(1H, d, J=1.98 Hz), 7.31(1H, d, J=0.66 Hz), 7.32–7.48(5H, m).

b) Synthesis of ethyl 4-chloro-1-(4-ethoxycarbonylbutyl)-6-hydroxy-1H-indolecarboxylate A mixture of ethyl 6-benzyloxy-4-chloro-1-(4-ethoxycarbonylbutyl)-1H-indolecarboxylate (15.0 g, 32.8 mmol), 35% hydrochloric acid (3.3 ml), acetic acid (240 ml), 10% palladium-carbon (1.5 g) and N,N-dimethylformamide (60 ml) was stirred under a hydrogen atmosphere at room temperature for about 1 hour. The catalyst was filtered off and the filtrate was poured into a cooled 5% aqueous sodium chloride solution and extracted twice with ethyl acetate. The extract solution was washed three times with a 5% aqueous sodium chloride solution and dried over anhydrous magnesium sulfate. The solvent was distilled off under reduced pressure and the resulting residue was crystallized from toluene to obtain 6.57 g of ethyl 4-chloro-1-(4-ethoxycarbonylbutyl)-6-hydroxy-1H-indolecarboxylate.

M.p. 74–76° C.

c) Synthesis of ethyl 4-chloro-1-(4-ethoxycarbonyl) butyl)-6-methoxy-1H-indolecarboxylate Ethyl 4-chloro-1-(4-ethoxycarbonylbutyl)-6-methoxy-1H-indolecarboxylate was obtained as an oil by carrying out reaction according to the method described in Example 38, (i), except for using ethyl 4-chloro-1-(4-ethoxycarbonylbutyl)-6-hydroxy-1H-indolecarboxylate (11.0 g, 29.9 mmol), methyl iodide (4.67 g, 32.9 mmol), potassium carbonate (8.27 g, 59.8 mmol) and N,N-dimethylformamide (77 ml).

$^1$Hnmr (CDCl$_3$) δ: 1.23(3H, t, J=7.26 Hz), 1.41(3H, t, J=7.26 Hz), 1.62–1.77(2H, m), 1.80–1.88(2H, m), 2.33(2H, t, J=7.26 Hz), 3.88(3H, s), 4.07–4.15(2H, m), 4.35(2H, dd, J=7.26 Hz, 14.18 Hz), 4.51(2H, t, J=7.26 Hz), 6.67–6.68 (1H, m), 6.85(1H, d, J=1.98 Hz), 7.31(1H, d, J=0.99 Hz).

d) Synthesis of ethyl 1-(4-carboxybutyl)-4-chloro-6-methoxy-1H-indolecarboxylate 9.8 Grams of ethyl 1-(4-carboxybutyl)-4-chloro-6-methoxy-1H-indolecarboxylate was obtained by carrying out reaction according to the method described in Reference Example 6, (b), except for using ethyl 4-chloro-1-(4-ethoxycarbonylbutyl)-6-methoxy-1H-indolecarboxylate (11.0g, 28.8 mmol), 30% sulfuric acid (55 ml) and acetic acid (165 ml).

M.p. 79–81° C. (after recrystallization from a mixed solvent of toluene and n-hexane).

e) Synthesis of ethyl 5,6,7,8-tetrahydro-11-chloro-9-methoxy-8-oxo-4H-azocino[3,2,1-hi]indole-2-carboxylate 2.98 Grams of ethyl 5,6,7,8-tetrahydro-11-chloro-9-methoxy-8-oxo-4H-azocino[3,2,1-hi]indole-2-carboxylate was obtained by carrying out reaction according to the method described in Reference Example 2, (c), except for using ethyl 1-(4-carboxybutyl)-4-chloro-6-methoxy-1H-indolecarboxylate (9.50 g, 26.9 mmol), thionyl chloride (24.9 g, 161 mmol), chloroform (190 ml) and aluminum chloride (7.16 g, 53.7 mmol).

M.p. 167–168° C. (after recrystallization from isopropanol).

f) Synthesis of N-(aminoiminomethyl)-5,6,7,8-tetrahydro-11-chloro-9-methoxy-8-oxo-4H-azocino[3,2,1-hi]indole-2-carboxamide methanesulfonate 0.36 Gram of N-(aminoiminomethyl)-5,6,7,8-tetrahydro-11-chloro-9-methoxy-8-oxo-4H-azocino[3,2,1-hi]indole-2-carboxamide methanesulfonate was obtained by carrying out reaction according to the method described in Example 1, except for using ethyl 5,6,7,8-tetrahydro-11-chloro-9-methoxy-8-oxo-4H-azocino [3,2,1-hi]indole-2-carboxylate (0.50 g, 1.49 mmol), sodium ethoxide (0.80 g, 14.9 mmol), guanidine hydrochloride (1.42 g, 14.9 mmol) and N,N-dimethylformamide (10 ml).

M.p. 274–275° C. (decomp.) (after recrystallization liza- tion from water).

In accordance with the process described in Example 37, compounds of Examples 41–43 were synthesized:

EXAMPLE 41

N-(aminoiminomethyl)-5,6,7,8-tetrahydro-11-chloro-9-hydroxy-8-oxo-4H-azocino[3.2.1-hi]indol-2-carboxamide methanesulfonate

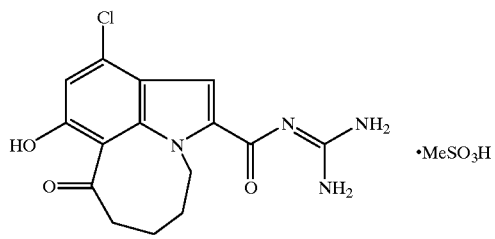

Melting point: 146–147° C. (recrystallized from mixed solvents of water and isopropyl alcohol)

EXAMPLE 42

N-(aminoiminomethyl)-5,6,7,8-tetrahydro-10-hydroxy-11-methyl-8-oxo-4H-azocino[3.2.1-hi]indole-2-carboxamide methanesulfonate

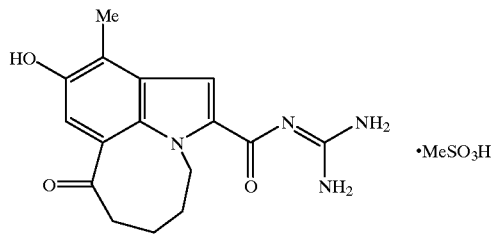

Melting point: 270–271° C. (dec.) (recrystallized from mixed solvents of water and isopropyl alcohol)

EXAMPLE 43

N-(aminoiminomethyl)-5,6,7,8-tetrahydro-9-hydroxy-11-methyl-8-oxo-4H-azocino[3.2.1-hi]indole-2-carboxamide methanesulfonate

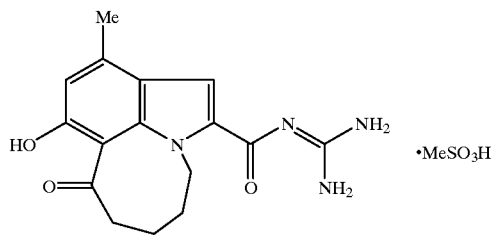

Melting point: 254° C. (dec.) (recrystallized from water)

EXAMPLE 44

Synthesis of N-(aminoiminomethyl)-5,6,7,8-tetrahydro-11-chloro-8-oxo-4H-azocino[3.2.1-hi]indole-2-carboxamide methanesulfonate (anhydride)

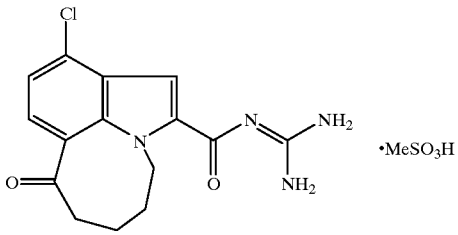

*kel,5q*N-(*aminoiminomethyl*)-5,6,7,8-*tetrahydro*-11-*chloro*-8-*oxo*-4H-*azocino*@3.2.1-*hi*#*indole*-2-*carboxamide methanesulfonate monohydrate*) obtained from Example 22 was recrystallized from methanol to give N-(*aminoiminomethyl*)-5,6,7,8-*tetrahydro*-11-*chloro*-8-*oxo*-4H-*azocino*@3.2.1-*hi*#*indole*-2-*carboxamide methanesulfonate* (*anhydride*).

Melting point: 253° C. (dec.)

Elementary analysis (for $C_{15}H_{15}ClN_4O_2 \cdot CH_4SO_3$):

|  | C | H | N |
|---|---|---|---|
| Calcd. (%) | 46.32 | 4.62 | 13.50 |
| Found (%) | 46.14 | 4.64 | 13.29 |

EXAMPLE 45

Synthesis of N-(aminoiminomethyl)-5,6,7,8-tetrahydro-11-hydroxymethyl-8-oxo-4H-azocino[3.2.1-hi]indole-2-carboxamide methanesulfonate

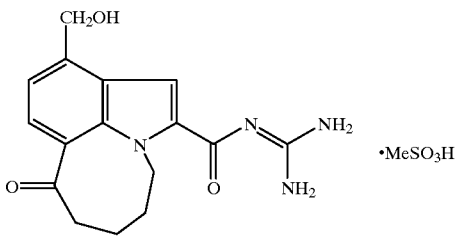

(a) Synthesis of ethyl 5,6,7,8-tetrahydro-11-bromomethyl-8-oxo-4H-azocino[3.2.1-hi]indole-2-carboxylate In accordance with the process described in Example 22(a)–(c) except for using ethyl 4-methyl-1H-indole-2-carboxylate as a starting material, ethyl 5,6,7,8-tetrahydro-11-methyl-8-oxo-4H-azocino[3.2.1-hi]indole-2-carboxylate (m.p. 98° C., recrystallized from isopropyl alcohol) was synthesized. Ethyl 5,6,7,8-tetrahydro-11-methyl-8-oxo-4H-azocino[3.2.1-hi]indole-2-carboxylate (2.50 g, 8.76 mmol) was then dissolved in carbon tetrachloride (80 ml) and N-bromosuccinimide (1.72 g, 9.64 mmol) and 2,2'-azobisisobutyronitrile (43 mg) were added therein under refluxing condition to heat at reflux for 2 hours. The reaction mixture was poured into water and extracted with chloroform. The extract was washed with saturated sodium chloride solution and dried over magnesium sulfate. The solvent was distilled off and the obtained residue was purified with silica gel column chromatography (eluated with ethyl acetate/n-hexane=1/10) to give ethyl 5,6,7,8-tetrahydro-11-bromomethyl-8-oxo-4H-azocino[3.2.1-hi]indole-2-carboxylate (3.12 g).

$^1$Hnmr (CDCl$_3$) δ: 1.44(3H, t, J=7.2 Hz), 1.77–1.85(2J, m), 2.05–2.10(2H, m), 2.80–2.84(2H, m), 4.41(2H, q, J=7.2 Hz), 4.56(2H, br-s), 4.78(2H, s), 7.20(1H, d, J=7.3 Hz), 7.27(1H, d, J=7.3 Hz), 7.50(1H, s).

(b) Synthesis of ethyl 5,6,7,8-tetrahydro-11-acetoxymethyl-8-oxo-4H-azocino[3.2.1-hi]indole-2-carboxylate A mixture of ethyl 5,6,7,8-tetrahydro-11-bromomethyl-8-oxo-4H-azocino[3.2.1-hi]indole-2-carboxylate (2.92 g, 8.02 mmol), potassium acetate (1.18 g, 12.0 mmol) and N,N-dimethylformamide (30 ml) was stirred at room temperature for 2.5 hours. The reaction mixture was poured into 10% aqueous sodium chloride solution and extracted with ethyl acetate. The extract was washed with 5% aqueous sodium chloride solution and dried over anhydrous magnesium sulfate. The solvent was distilled off and the obtained residue was purified with silica gel column chromatography (eluated with ethyl acetate/n-hexane=1/5) to give 2.33 g of ethyl 5,6,7,8-tetrahydro-11-acetoxymethyl-8-oxo-4H-azocino[3.2.1-hi]indole-2-carboxylate.

$^1$Hnmr (CDCl$_3$) δ: 1.44(3H, t, J=7.2 Hz), 1.75–1.84(2H, m), 2.07–2.11(2H, m), 2.14(3H, s), 2.81–2.84 (2H, m), 4.40(2H, q, J=7.2 Hz), 4.56(2H, br-s), 5.41(2H, s), 7.20(1H, d, J=7.3 Hz), 7.32(1H, d, J=7.3 Hz), 7.42(1H, s).

(c) Synthesis of N-(aminoiminomethyl)-5,6,7,8-tetrahydro-11-hydroxymethyl-8-oxo-4H-azocino[3.2.1-hi]indole-2-carboxamide methanesulfonate In accordance with the process described in Example 1 except for using ethyl 5,6,7,8-tetrahydro-11-acetoxymethyl-8-oxo-4H-azocino[3.2.1-hi]indole-2-carboxylate (2.13 g, 6.20 mmol), guanidine hydrochloride (5.92 g, 62 mmol), sodium methoxide (3.35 g, 62 mmol) and N,N-dimethylformamide (50 ml), 1.07 g of N-(aminoiminomethyl)-5,6,7, 8-tetrahydro-11-hydroxymethyl-8-oxo-4H-azcino[3.2.1-hi]indole-2-carboxamide methanesulfonate was obtained.

Melting point: 248–250° C. (dec.) (recrystallized from water)

Test Example

Inhibitry effect on the Na$^+$/H$^+$ exchange transport system (in vitro)

Test Method

A test was carried out according to the method of Iemori et al. (J. Hypertension, 8, 153 (1990)). In detail, inhibitory effect on the Na$^+$/H$^+$ exchange transport system was evaluated by using as an indication a pH change in isolated ventricular myocytes (rat) under an acid load.

Test Results

| Example | Inhibitory effect on Na$^+$/H$^+$ exchange transport system IC$_{50}$ (μM) |
|---|---|
| Example 1 | 0.3 |
| Example 2 | 0.2 |
| Example 3 | 0.3 |

The compounds of the present invention have inhibitory effect on the sodium/proton (Na$^+$/H$^+$) exchange transport system and hence are useful as a therapeutic or prophylactic agent for diseases caused by the acceleration of the sodium/proton ($Na^+/H^+$) exchange transport system, for example, hyperpiesia, arrhythmia, angina pectoris, hypercardia, diabetes, organopathies due to ischemia or ischemia re-perfusion [for instance, troubles caused by myocardial ischemia re-perfusion, acute renal failute, and surgical treatments (e.g. organ transplantation and PTCA (percutaneous transluminal coronary angioplasty))], troubles due to cerebral ischemia (e.g. troubles accompanying cerebral infarction, troubles brought about as after-effects of cerebral apoplexy, and cerebral edema), diseases caused by cell over-proliferations (e.g. fibroblast proliferation, smooth muscle cell proliferation and mesangial cell proliferation) (e.g. atherosclerosis, fibroid lung, fibroid liver, fibroid kidney, renal glomerulosclerosis, organ hypertrophy, prostatomegaly, complications of diabetes, and re-constriction after PTCA), and diseases caused by trouble with endothelial cells.

What we claim are:

1. A compound of formula (1):

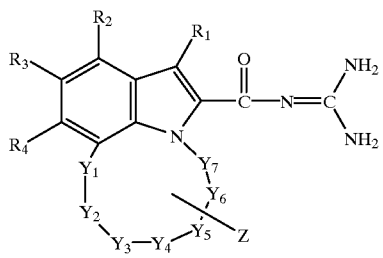

(1)

wherein $R_1$, $R_2$, $R_3$ and R4 are independently a hydrogen atom, an unsubstituted alkyl group, a substituted alkyl group, a cycloalkyl group, a cycloalkenyl group, a saturated heterocyclic group, a halogen atom, a nitro group, a carboxyl group, an alkoxycarbonyl group, an aromatic group, an acyl group, —$OR_5$, —$N(R_6)R_7$, —$CON(R_6)R_7$, —$SO_2N(R_6)R_7$, —$S(O)_nR_8$ wherein $R_8$ is an unsubstituted alkyl group, a substituted alkyl group or an aromatic group, and n is an integer of 0, 1 or 2, —Q—Ra, or

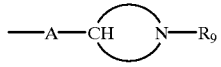

wherein A is an oxygen atom, —$S(O)_n$— wherein n is as defined above or —$N(R_{10})$—, $R_9$ is a hydrogen atom, an unsubstituted alkyl group, a substituted alkyl group, an acyl group or —Q—Ra, and the ring is a 3- to 8-membered saturated heterocyclic group composed of a nitrogen atom and carbon atoms;

$Y_1$, $Y_2$, $Y_3$, $Y_4$, $Y_5$, $Y_6$ and $Y_7$, which may be the same or different, are independently a single bond, —$CH_2$—, [—O—,]O—CO—, —C(=C($R_{11}$)$R_{12}$)—, [—S(O)$_n$—] or —N(R)$_{10}$—, adjacent members of a group consisting of $Y_1$ through $Y_7$ being able to be taken together to represent —CH=CH—, provided that (a) four of $Y_1$ through $Y_7$ are independently a group other than a single bond or —$NR_{10}$—, (b) two of $Y_1$ through $Y_7$ are independently a single bond, and (c) the remaining one is —$N(R_{10})$—;

Z may be absent, or one or more Zs may be present and are, the same or different, independently the following substituent for a hydrogen atom bonded to any of the carbon atoms constituting the ring formed by $Y_1$ through $Y_7$; an unsubstituted alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, an acyl group, —$OR_5$, —$N(R_6)R_7$, —$S(O)_nR_8$, —$C(O)N(R_6)R_7$, or —Q—Ra, provided that when Z is a substituent for the hydrogen atom of —CH=CH—, Z is not —$N(R_6)R_7$ or —$S(O)_nR_8$;

Q is a substituted or unsubstituted lower alkylene group;

Ra is a substituted or unsubstituted vinyl group, or a substituted or unsubstituted ethynyl group;

$R_5$ is a hydrogen atom, an unsubstituted alkyl group, a substituted alkyl group, a cycloalkyl group, a cycloalkenyl group, a saturated heterocyclic group or an aromatic group;

$R_6$ and $R_7$ are independently a hydrogen atom, an unsubstituted alkyl group, a substituted alkyl group, a cycloalkyl group, a cycloalkenyl group, a saturated heterocyclic group, an aromatic group, an acyl group or —Q—Ra, or $R_6$ and $R_7$, when taken together with the nitrogen atom to which they are bonded, form a saturated 5- to 7-membered cyclic amino group which may contain an oxygen atom or a sulfur atom in the ring and may be substituted by one or more unsubstituted alkyl groups, substituted alkyl groups, hydroxyl groups or —$OR_5$ groups;

$R_8$ is an unsubstituted alkyl group, a substituted alkyl group or an aromatic group;

$R_{10}$ is a hydrogen atom, an unsubstituted alkyl group, a substituted alkyl group, a cycloalkyl group, a saturated heterocyclic group, an aromatic group, an acyl group or —Q—Ra; and $R_{11}$ and $R_{12}$ are independently a hydrogen atom, an unsubstituted alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, an acyl group, —$OR_5$, —$N(R_6)R_7$, —$CON(R_6)R_7$, —$S(O)_nR_8$ or —Q—Ra or a pharmaceutically acceptable acid addition salt thereof.

2. A compound of formula (1) or a pharmaceutically acceptable acid addition salt thereof according to claim 1, wherein $R_1$, $R_2$, $R_3$ and $R_4$ are independently a hydrogen atom, an unsubstituted alkyl group, a substituted alkyl group, a halogen atom, a nitro group, an aromatic group, an acyl group, —$OR_5$, —$N(R_6)R_7$, —$CON(R_6)R_7$, —$SO_2N(R_6)R_7$, —$S(O)_nR_8$ or —Q—Ra wherein Ra is a substituted or unsubstituted vinyl group.

3. A compound of formula (1) or a pharmaceutically acceptable acid addition salt thereof according to claim 1, wherein $R_1$ is a hydrogen atom.

4. A compound of formula (1) or a pharmaceutically acceptable acid addition salt thereof according to claim 1, wherein $R_1$, $R_2$, $R_3$ and $R_4$ are independently a hydrogen atom, an unsubstituted alkyl group, a substituted alkyl group, a halogen atom, an acyl group, —$OR_5$, —$N(R_6)R_7$, —$CON(R_6)R_7$, —$SO_2N(R_6)R_7$, or —$S(O)_nR_8$.

5. A compound of formula (1) or a pharmaceutically acceptable acid addition salt thereof according to claim 1, wherein Z may be absent, or one or more Zs may be present and are, the same or different, independently the following substituent for a hydrogen atom bonded to any of the carbon atoms constituting the ring formed by $Y_1$ through $Y_7$: an unsubstituted alkyl group, a substituted alkyl group, an alkenyl group, a cycloalkyl group, a saturated heterocyclic group, a carboxyl group, an aromatic group, an acyl group, —$OR_5$, —$N(R_6)R_7$, —$S(O)_nR_8$, or —$C(O)N(R_6) R_7$, provided that when Z is a substituent for the hydrogen atom of —CH=CH—, Z is not —$N(R_6)R_7$ or —$S(O)_nR_8$.

6. A compound of formula (1) or a pharmaceutically acceptable acid addition salt thereof according to claim 1, 2, 3, 4, or 5, wherein one of $Y_1$ through $Y_7$ is —$N(R_{10})$—, another is —$CH_2$—, and the five others, which may be the same or different, are independently a single bond or —$CH_2$—, and Z is as defined in claim 1.

7. A compound of formula (1) or a pharmaceutically acceptable acid addition salt thereof according to claim 6, wherein $Y_1$ is —$N(R_{10})$—, $Y_2$ is —$CH_2$—, $Y_3$ through $Y_7$, which may be the same or different, are independently a single bond or —$CH_2$—.

8. A compound of formula (1) or a pharmaceutically acceptable acid addition salt thereof according to claim 1 or 2, wherein $Y_1$ is —$N(R_{10})$—, one of $Y_2$ through $Y_7$ is —CO—, the five others, which may be the same or different, are independently a single bond or —$CH_2$—.

9. A compound of formula (1) or a pharmaceutically acceptable acid addition salt thereof according to claim 8, wherein $Y_2$ is —CO—.

10. A process for producing a compound of the formula (1) or a pharmaceutically acceptable acid addition salt thereof according to claim 1, which comprises reacting a compound represented by the formula (2):

(2)

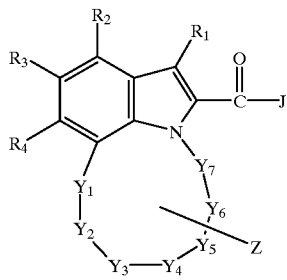

wherein $R_1, R_2, R_3, R_4, Y_1, Y_2, Y_3, Y_4, Y_5, Y_6, Y_7$ and Z are as defined in claim 1, and J is a leaving group replaceable by a nucleophilic reagent, with guanidine.

11. A pharmaceutical composition comprising a compound of formula (1) or a pharmaceutically acceptable acid addition salt thereof according to any one of claims 1–7, 8 or 9 as an active ingredient.

12. A method for treating a disease selected from the group consisting of: hyperpiesia, arrhythmia, angina pectoris, hypercardia, diabetes, organopathies due to ischemia or ischemia re-perfusion, troubles due to cerebral ischemia, diseases caused by cell over-proliferations, and diseases caused by trouble with endothelial cells, which comprises administering an effective amount of a compound of formula (1) or a pharmaceutically acceptable acid addition salt thereof according to any one of claims 1–7, 8 or 9 to a patient in need thereof.

13. A method for treating ischemia which comprises administering an effective amount of a compound of formula (1) or a pharmaceutically acceptable acid addition salt thereof to a patient, wherein formula (1) is:

(1)

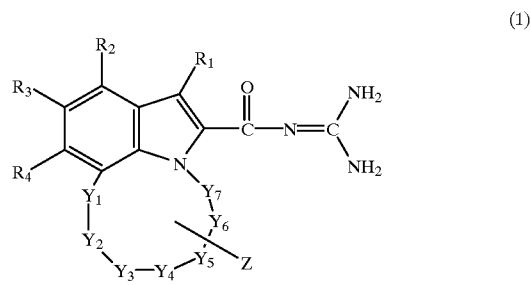

wherein $R_1$, $R_2$, $R_3$ and $R_4$ are independently a hydrogen atom, an unsubstituted alkyl group, a substituted alkyl group, a cycloalkyl group, a cycloalkenyl group, a saturated heterocyclic group, a halogen atom, a nitro group, a carboxyl group, an alkoxycarbonyl group, an aromatic group, an acyl group, —$OR_5$, —$N(R_6)R_7$, —$CON(R_6)R_7$, —$SO_2N(R_6)R_7$, —$S(O)_nR_8$ wherein $R_8$ is an unsubstituted alkyl group, a substituted alkyl group or an aromatic group, and n is an integer of 0, 1 or 2, —Q—Ra, or

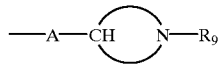

wherein A is an oxygen atom, —$S(O)_n$— wherein n is defined above or —$N(R_{10})$—, $R_9$ is a hydrogen atom, an unsubstituted alkyl group, a substituted alkyl group, an acyl group or —Q—RA, and the ring is a 3- to 8-membered saturated heterocyclic group composed of a nitrogen atom and carbon atoms;

$Y_1, Y_2, Y_3, Y_4, Y_5, Y_6$ and $Y_7$, which may be the same or different, are independently a singe bond, —$CH_2$—, —CO—, —C( . C($R_{11}$)$R_{12}$)—, or —$N(R_{10})$—, adjacent members of a group consisting of $Y_1$ through $Y_7$ being able to be taken together to represent —CH=CH—, provided that (a) four of $Y_1$ through $Y_7$ are independently a group other than a single bond or —$NR_{10}$—, (b) two of $Y_1$ through $Y_7$ are independently a single bond, and (c) the remaining one is —$N(R_{10})$—;

Z may be absent, or one or more Zs may be present and are, the same or different, independently the following substituent for hydrogen atom bonded to any of the carbon atoms constituting the ring formed by $Y_1$ through $Y_7$; an unsubstituted alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, an acyl group, —$OR_5$, —$N(R_6)R_7$, —$S(O)_nR_8$, —$C(O)N(R_6)R_7$, or —Q—Ra, provided that when Z is a substituent for the hydrogen atom of —CH=CH—, Z is not —$N(R_6)R_7$ or —$S(O)_nR_8$;

Q is a substituted or unsubstituted lower alkylene group;

Ra is a substituted or unsubstituted vinyl group, or a substituted or unsubstituted ethynyl group;

$R_5$ is a hydrogen atom, an unsubstituted alkyl group, a substituted alkyl group, a cycloalkyl group, a cycloalkenyl group, a saturated heterocyclic group or an aromatic group;

$R_6$ and $R_7$ are independently a hydrogen atom, an unsubstituted alkyl group, a substituted alkyl group, a cycloalkyl group, a cycloalkenyl group, a saturated heterocyclic group, an aromatic group, an acyl group or —Q—Ra, or $R_6$ and $R_7$, when taken together with the nitrogen atom to which they are bonded, form a saturated 5- to 7-membered cyclic amino group which may contain an oxygen atom or a sulfur atom in the ring and may be substituted by one or more unsubstituted alkyl groups, substituted alkyl groups, hydroxyl groups or —$OR_5$ groups;

$R_8$ is an unsubstituted alkyl group, a substituted alkyl group or an aromatic group;

$R_{10}$ is a hydrogen atom, an unsubstituted alkyl group, a substituted alkyl group, a cycloalkyl group, a saturated heterocyclic group, an aromatic group, an acyl group or —Q—Ra; and $R_{11}$ and $R_{12}$ and independently a hydrogen atom, an unsubstituted alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, an acyl group, —$OR_5$, —$N(R_6)R_7$, —$CON(R_6)R_7$, —$S(O)_nR_8$ or —Q—Ra.

* * * * *